US012721809B2

(12) United States Patent
Zang et al.

(10) Patent No.: US 12,721,809 B2
(45) Date of Patent: Sep. 1, 2026

(54) FORMULATION FOR TREATING OPHTHALMIC CONDITIONS

(71) Applicant: Guangzhou KangRui Biological Pharmaceutical Technology Co., Ltd., Guangzhou (CN)

(72) Inventors: Guangxi Zang, Guangzhou (CN); Rui Hou, Guangzhou (CN)

(73) Assignee: Lan Tech Limited, Tortola (VG)

( * ) Notice: Subject to any disclaimer, the term of this patent is extended or adjusted under 35 U.S.C. 154(b) by 700 days.

(21) Appl. No.: 17/921,055

(22) PCT Filed: Apr. 23, 2021

(86) PCT No.: PCT/CN2021/089415

§ 371 (c)(1),
(2) Date: Oct. 24, 2022

(87) PCT Pub. No.: WO2021/213512

PCT Pub. Date: Oct. 28, 2021

(65) Prior Publication Data

US 2023/0301904 A1 Sep. 28, 2023

(51) Int. Cl.

| | |
|---|---|
| ***A61K 9/00*** | (2006.01) |
| ***A61K 9/10*** | (2006.01) |
| ***A61K 31/506*** | (2006.01) |
| ***A61K 47/02*** | (2006.01) |
| ***A61K 47/34*** | (2017.01) |
| ***A61K 47/38*** | (2006.01) |
| ***A61P 17/00*** | (2006.01) |

(Continued)

(52) U.S. Cl.
CPC .............. *A61K 9/0048* (2013.01); *A61K 9/10* (2013.01); *A61K 31/506* (2013.01); *A61K 47/02* (2013.01); *A61K 47/34* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 4,938,763 | A | 7/1990 | Dunn et al. |
| 5,033,252 | A | 7/1991 | Carter |

(Continued)

FOREIGN PATENT DOCUMENTS

| | | | |
|---|---|---|---|
| CN | 104334543 | A | 2/2015 |
| EP | 2985283 | A1 | 2/2016 |
| JP | 2016-515636 | A | 5/2016 |

OTHER PUBLICATIONS

Taktak, Y.S., et al, "Assay of Pyrogens by Interleukin-6 Release from Monocytic Cell Lines," J. Pharm. Pharmacol., vol. 4 (1990), pp. 578-582.

(Continued)

*Primary Examiner* — Kyung S Chang
(74) *Attorney, Agent, or Firm* — Banner & Witcoff, Ltd.

(57) ABSTRACT

A pharmaceutical composition for ophthalmic dosing or administration is disclosed, comprising (i) a compound of Formula (I) or an isotopic variant, tautomer, pharmaceutically acceptable salt, solvate, or hydrate thereof; and (ii) at least one pharmaceutically acceptable excipient. The pharmaceutical composition is formulated as a suspension. The composition may be used to treat ophthalmic disorders and diseases caused by abnormal proliferation of angiogenesis.

20 Claims, 7 Drawing Sheets

(51) Int. Cl.

| | |
|---|---|
| ***A61P 27/02*** | (2006.01) |
| ***A61P 27/06*** | (2006.01) |
| ***A61P 27/10*** | (2006.01) |
| ***A61P 27/12*** | (2006.01) |
| ***A61P 35/00*** | (2006.01) |

(56) References Cited

U.S. PATENT DOCUMENTS

| | | | |
|---|---|---|---|
| 5,052,558 A | 10/1991 | Carter | |
| 5,323,907 A | 6/1994 | Kalvelage | |
| 5,324,519 A | 6/1994 | Dunn et al. | |
| 5,702,716 A | 12/1997 | Dunn et al. | |
| 5,744,153 A | 4/1998 | Yewey et al. | |
| 5,990,194 A | 11/1999 | Dunn et al. | |
| 2010/0048636 A1* | 2/2010 | Baldwin | A61P 25/22 514/354 |
| 2012/0114637 A1 | 5/2012 | Nivaggioli et al. | |
| 2017/0119768 A1 | 5/2017 | Hou et al. | |
| 2018/0147297 A1* | 5/2018 | Loftsson | A61K 9/50 |

OTHER PUBLICATIONS

Rao, K. Panduranga, "Recent developments of collagen-based materials for medical applications and drug delivery systems", J Biomater. Sci. Polymer Edn, No. 7 (1995), pp. 623-645.

Ostro, Marc J. et al., "Use of liposomes as injectable-drug delivery systems", Am. J. Hosp. Pharm. vol. 46, (Aug. 1989), pp. 1576-1587.

Jeong, Byeongmoon, et al., "Biodegradable block copolymers as injectable drug delivery systems", Letters to Nature vol. 388, Aug. 28, 1997, pp. 860-862.

Jeong, Byeongmoon, et al., "Drug release from biodegradable injectable thermosensitive hydrogel of PEG-PLGA-PEG triblock copolymers", J. Control. Release 63 (2000), pp. 155-163.

Jong, Byeongmoon, et al. "Thermosensitive sol-gel reversible hydrogels", Adv. Drug Delivery Drug Rev. 54 (2002), pp. 37-51.

Aug. 2, 2021—(WO) International Search Report—App PCT/CN2021/089415.

Gao, Zhi-Hui, et al. Controlled Release of a Contraceptive Steroid from Biodegradable and Injectable Gel Formulations: In Vitro Evaluation, Pharm. Res. vol. 12, No. 6, (1995), pp. 857-863.

Eyles, J.E., et al., Oral Delivery of Fate of Poly(lactic acid) Microsphere-encapsulated Interferon in Rats, J. Pharm. Pharmacol., vol. 49, (1997), pp. 669-674.

Chonn, Arcadio et al., "Recent advances in liposomal drug-delivery systems", Current Opinion in Biotechnology, vol. 6, (1995) pp. 698-708.

Berge, Stephen M., et al. "Pharmaceutical Salts", Journal of Pharmaceutical Science, vol. 66, No. 1, (1977), pp. 1-19.

Sun, Li, et al., "Applications of Suspending Agents in Suspension Eye Drops with English translation", NCPC New Drug Research and Development Co., Ltd., Shijiazhuang China, vol. 32, No. 8, (Aug. 2009), 7 pages.

Al-Muhammed, et al., "In-vivo studies on dexamethasone sodium phosphate liposomes", Journal of Microencapsulation vol. 13, No. 3, (1996) pp. 293-306.

Baranowski, Przemyslaw, Karolewicz, Bozena, Gajda, Maciej, and pluta, Janusz, "Ophthalmic Drug Dosage Forms: Characterisation and Research Methods," The Scientific World Journal, vol. 2014, Article ID 861904, 14 pages.

Jun. 30, 2023—(IN) First Office Action—App No. 202247066 162.

Sep. 8, 2023—(CN) First Office Action—App 202180030232.X.

Oct. 31, 2023—(JP) Notice of Reasons for Refusal—App 2022-564239.

Oct. 23, 2023—(AU) Examination Report—App 201260669.

Aug. 25, 2023—(EP) European Search Report—App 21792973.6.

May 15, 2024—(JP) Decision of Refusal—App 2022-564239.

May 24, 2024—(IN) Hearing Notice—App 202247066162.

Feb. 15, 2024—(CA) Examination Report—App 3,173,676.

Apr. 18, 2025—(KR) Office Action—App 10-2022-7041397.

* cited by examiner 8
6
4
2
0
% Volume
Before pulverization
After pulverization
0.001 0.01 0.1 1 10 100 1000 10000
Particle Size (μm)

mAU
Time (min)

FORMULATION FOR TREATING OPHTHALMIC CONDITIONS

CROSS-REFERENCE TO RELATED APPLICATION

The present application is a U.S. National Phase Entry of International PCT Application No. PCT/CN2021/089415 having an international filing date of Apr. 23, 2021, which claims priority to International PCT Application No. PCT/CN2020/086647, both of the applications are incorporated herein by reference in its entirety.

BACKGROUND

Angiogenesis and neovascularization are the formation or growth of new or existing capillaries or blood vessels, which may have importance in disease and health. Pathologic ocular angiogenesis or neovascularization can occur in retina, choroid, and cornea resulting in severe visual impairment. It is related to a broad spectrum of disorders including wet age-related macular degeneration (AMD), diabetic retinopathy, retinal artery or vein occlusion, retinopathy of prematurity (ROP), neovascular glaucoma, and corneal neovascularization secondary to infectious or inflammatory processes.

BRIEF SUMMARY OF THE DISCLOSURE

In an aspect, provided herein is a pharmaceutical composition, comprising:

(i) a compound of Formula (I):

(I)

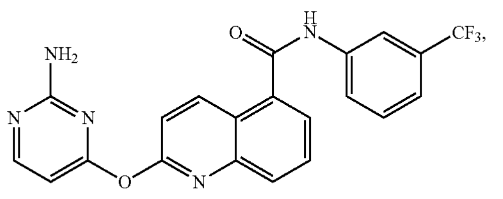

or an isotopic variant, tautomer, pharmaceutically acceptable salt, solvate, or hydrate thereof; and (ii) at least one pharmaceutically acceptable excipient, wherein the pharmaceutical composition is in a dosage form for ophthalmic dosing or administration.

In some embodiments, the dosage form is a suspension comprising fine particles of a compound of Formula (I), or an isotopic variant, tautomer, pharmaceutically acceptable salt, solvate, or hydrate thereof.

In an aspect, provided herein is a pharmaceutical composition, comprising:

(i) fine particles of a compound of Formula (I):

(I)

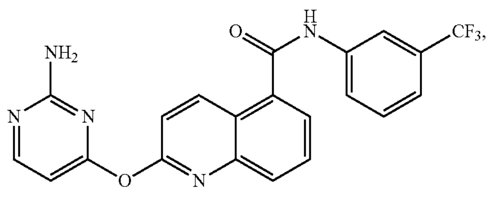

or an isotopic variant, tautomer, pharmaceutically acceptable salt, solvate, or hydrate thereof; and (ii) at least one pharmaceutically acceptable excipient, wherein the pharmaceutical composition is formulated as a suspension, gel, or ointment.

In some embodiments, the particles are micronized.

In some embodiments, the particles of the compound of Formula (I), or an isotopic variant, tautomer, pharmaceutically acceptable salt, solvate, or hydrate thereof have a diameter of from about 0.1 μm to about 40 μm.

In some embodiments, the particles of the compound of Formula (I), or an isotopic variant, tautomer, pharmaceutically acceptable salt, solvate, or hydrate thereof have a diameter of from about 0.1 μm to about 10 μm.

In some embodiments, the particles of the compound of Formula (I), or an isotopic variant, tautomer, pharmaceutically acceptable salt, solvate, or hydrate thereof have a diameter of from about 0.3 μm to about 5 μm.

In some embodiments, at least about 10% of the particles have a diameter of from about 0.1 μm to about 40 μm. In some embodiments, at least about 20% of the particles have a diameter of from about 0.1 μm to about 40 μm. In some embodiments, at least about 30% of the particles have a diameter of from about 0.1 μm to about 40 μm. In some embodiments, at least about 40% of the particles have a diameter of from about 0.1 μm to about 40 μm. In some embodiments, at least about 50% of the particles have a diameter of from about 0.1 μm to about 40 μm. In some embodiments, at least about 60% of the particles have a diameter of from about 0.1 μm to about 40 μm. In some embodiments, at least about 70% of the particles have a diameter of from about 0.1 μm to about 40 μm. In some embodiments, at least about 80% of the particles have a diameter of from about 0.1 μm to about 40 μm. In some embodiments, at least about 90% of the particles have a diameter of from about 0.1 μm to about 40 μm. In some embodiments, at least about 95% of the particles have a diameter of from about 0.1 μm to about 40 μm.

In some embodiments, the particles have a D10 value of less than about 0.5 μm. In some embodiments, the particles have a D10 value of less than about 1 μm. In some embodiments, the particles have a D10 value of less than about 1.5 μm.

In some embodiments, the particles have a D50 value of less than about 2.5 μm.

In some embodiments, the particles have a D50 value of less than about 5 μm. In some embodiments, the particles have a D50 value of less than about 7.5 μm.

In some embodiments, the particles have a D90 value of less than about 5 μm. In some embodiments, the particles have a D90 value of less than about 10 μm. In some embodiments, the particles have a D90 value of less than about 15 μm.

In some embodiments, the compound of Formula (I) or an isotopic variant, tautomer, pharmaceutically acceptable salt, solvate, or hydrate thereof; is crystalline, microcrystalline, amorphous, or lyophilized.

In some embodiments, the dosage form is a modified-release dosage form.

In some embodiments, the modified-release dosage form is a delayed-release dosage form, an extended-release (ER) dosage form, or a targeted-release dosage form.

In some embodiments, the ER dosage form is a sustained-release (SR) dosage form or controlled-release (CR) dosage form.

In some embodiments, the composition comprises from about 0.025% to about 2.0% w/v of a compound of Formula (I), or an isotopic variant, tautomer, pharmaceutically acceptable salt, solvate, or hydrate thereof. In some embodiments, the composition comprises from about 0.05% to about 0.5% w/v of a compound of Formula (I), or an isotopic variant, tautomer, pharmaceutically acceptable salt, solvate, or hydrate thereof. In some embodiments, the composition comprises from about 0.05% to about 0.15% w/v of a compound of Formula (I), or an isotopic variant, tautomer, pharmaceutically acceptable salt, solvate, or hydrate thereof.

In some embodiments, the at least one pharmaceutically acceptable excipient is a diluent, buffering agent, suspending agent, solubilizer, emulsifier, antioxidant, pH adjusting agent, preservative, detackifier, anti-foaming agent, chelating agent, thickening agent, viscomodulator, tonicifier, colorant, opacifier, binder, filler, plasticizer, or any combination thereof.

In some embodiments, the at least one pharmaceutically acceptable excipient is a suspending agent, a wetting agent, a pH adjuster, an anti-oxidant, an osmotic pressure regulator, or any combination thereof.

In some embodiments, the suspending agent is a polymer.

In some embodiments, the suspending agent is a carbomer homopolymer, carbomer copolymer, carbomer interpolymer, polycarbophil, a cellulose derivative, a polyvinyl alcohol, a povidone, a hyaluronic acid or a salt thereof, chondroitin sulfate, a natural gum, or any combination thereof.

In some embodiments, the cellulose derivative is hydroxypropyl methylcellulose, hydroxyethyl cellulose, hydroxypropyl cellulose, or any combination thereof.

In some embodiments, the hydroxypropyl methylcellulose (HPMC) is K100, K4M, K15M, K100M, E4M, E10M, or any combination thereof.

In some embodiments, the suspending agent is hydroxypropyl methylcellulose (HPMC).

In some embodiments, the hypromellose is HPMC E4M.

In some embodiments, the concentration of the suspending agent in the compositions is up to about 1% w/w.

In some embodiments, the concentration of the suspending agent in the formulation is up to about 0.5% w/w.

In some embodiments, the solubilizer is Kolliphor® ELP, Kolliphor® HS 15, or a combination thereof. In some embodiments, the solubilizer is Kolliphor® HS 15.

In some embodiments, the concentration of the solubilizer in the composition is up to about 5% w/w.

In some embodiments, the wetting agent is polyoxyl 15-hydroxystearate.

In some embodiments, the pH adjuster is a buffer. In some embodiments, the buffer is selected from borates, borate-polyol complexes, phosphate buffering agents, citrate buffering agents, acetate buffering agents, carbonate buffering agents, organic buffering agents, amino acid buffering agents, or combinations thereof. In some embodiments, the buffer is a phosphate buffer or a hydrate thereof. In some embodiments, the phosphate buffer is potassium phosphate or a hydrate thereof. In some embodiments, the phosphate buffer is sodium dihydrogen phosphate dihydrate ($NaH_2PO_4 \cdot 2H_2O$), di-sodium hydrogen phosphate dodecahydrate ($Na_2HPO_4 \cdot 12H_2O$), or a combination thereof.

In some embodiments, the osmotic pressure regulator is a salt.

In some embodiments, the salt is sodium chloride.

In some embodiments, the concentration of the osmotic pressure regulator in the composition is up to about 0.5% w/w.

In some embodiments, the anti-oxidant is a thiosulfate.

In some embodiments, the thiosulfate is sodium thiosulfate.

In some embodiments, the concentration of the anti-oxidant in the composition is up to about 0.2% w/w.

In some embodiments, the composition is stable for up to 24 months at a temperature of from about 20° C. to about 25° C.

In some embodiments, the composition is substantially free of impurities.

In some embodiments, the composition is at least about 90% by weight pure. In some embodiments, the composition is at least about 95% by weight pure. In some embodiments, the composition is at least about 96% by weight pure. In some embodiments, the composition is at least about 97% by weight pure. In some embodiments, the composition is at least about 98% by weight pure. In some embodiments, the composition is at least about 99% by weight pure. In some embodiments, the composition is at least about 99.1%, about 99.2%, about 99.3%, about 99.4%, about 99.5%, about 99.6%, about 99.7%, about 99.8%, about 99.9%, or about 100% by weight pure.

In some embodiments, the composition comprises up to about 2% w/w of total impurities.

In some embodiments, the composition comprises less than about 0.9% w/w, about 0.8% w/w, about 0.7% w/w, about 0.6% w/w, about 0.5% w/w, about 0.4% w/w, about 0.3% w/w, about 0.2% w/w, or about 0.1% w/w of total impurities.

In some embodiments, the impurity is a degradant.

In some embodiments, the impurity comprises the compound of Formula (II):

(II)

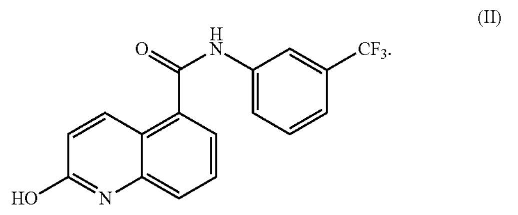 [SMILES: O=C(Nc1cccc(C(F)(F)F)c1)c1cccc2nc(O)ccc12]

In some embodiments, the composition comprises up to about 2.0% w/w of any individual impurity.

In some embodiments, the composition has a pH of from about 4.0 to about 9.0. In some embodiments, the composition has a pH of from about 5.0 to about 8.0. In some embodiments, the composition has a pH of from about 6.5 to about 8.0. In some embodiments, the composition has a pH of from about 7.0 to about 8.0.

In an aspect, provided herein is a method of treating or preventing a disorder or disease, comprising administering to a subject in need thereof a therapeutically effective amount of a pharmaceutical composition comprising:

(i) a compound of Formula (I):

(I)

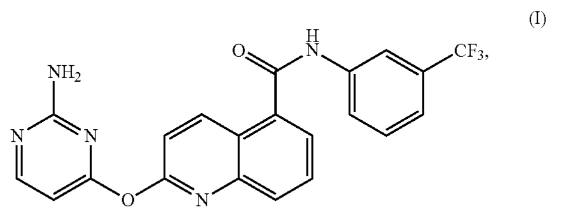 [SMILES: Nc1nccc(Oc2ccc3c(C(=O)Nc4cccc(C(F)(F)F)c4)cccc3n2)n1]

or an isotopic variant, tautomer, pharmaceutically acceptable salt, solvate, or hydrate thereof; and (ii) at least one pharmaceutically acceptable excipient, wherein the pharmaceutical composition is in a dosage form for ophthalmic dosing or administration;

and wherein the disorder or disease is a neovascular disorder or disease, inflammatory disorder or disease, or a cancer.

In an aspect, provided herein is a method of treating or preventing a disorder or disease, comprising administering to a subject in need thereof a therapeutically effective amount of a pharmaceutical composition comprising:

(i) fine particles of a compound of Formula (I):

(I)

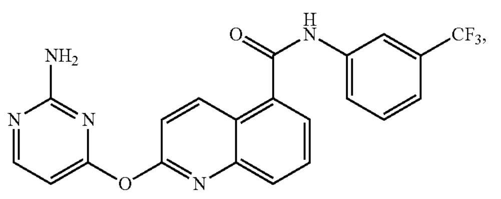

or an isotopic variant, tautomer, pharmaceutically acceptable salt, solvate, or hydrate thereof; and (ii) at least one pharmaceutically acceptable excipient, wherein the pharmaceutical composition is formulated as a suspension;

and wherein the disorder or disease is a neovascular disorder or disease, inflammatory disorder or disease, or a cancer.

In an aspect, provided herein is a method of treating or preventing an ophthalmic disorder or disease, comprising administering to a subject in need thereof a therapeutically effective amount of a pharmaceutical composition comprising:

(i) a compound of Formula (I):

(I)

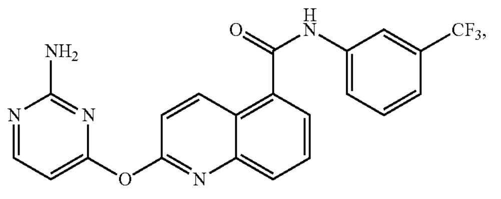

or an isotopic variant, tautomer, pharmaceutically acceptable salt, solvate, or hydrate thereof; and (ii) at least one pharmaceutically acceptable excipient, wherein the pharmaceutical composition is in a dosage form for ophthalmic dosing or administration.

In an aspect, provided herein is a method of treating or preventing an ophthalmic disorder or disease, comprising administering to a subject in need thereof a therapeutically effective amount of a pharmaceutical composition comprising:

(i) fine particles of a compound of Formula (I):

(I)

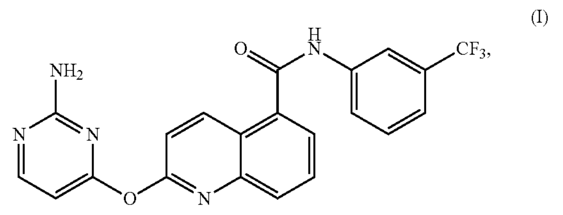 [SMILES: Nc1nccc(Oc2ccc3c(C(=O)Nc4cccc(C(F)(F)F)c4)cccc3n2)n1]

or an isotopic variant, tautomer, pharmaceutically acceptable salt, solvate, or hydrate thereof; and (ii) at least one pharmaceutically acceptable excipient, wherein the pharmaceutical composition is formulated as a suspension.

In some embodiments, the ophthalmic disorder or disease affects function, clarity, and/or structure of the lens of the eye.

In some embodiments, the ophthalmic disorder or disease is wet macular degeneration, cataracts, presbyopia, nuclear sclerosis of the eye lens, Refsum disease, Smith-Lemli-Opitz syndrome (SLOS), Schnyder crystalline corneal dystrophy (SCCD), abetalipoproteinemia, familial hypobetalipoproteinemia, neovascularization, or cancer.

In some embodiments, the neovascularization is corneal neovascularization, iris neovascularization, or choroidal neovascularization.

In some embodiments, the ophthalmic disorder or disease is corneal neovascularization.

In some embodiments, the subject has undergone a surgical procedure for treatment of the ophthalmic disorder or disease.

In some embodiments, about 0.005 mg/mL to about 5.0 mg/mL of a pharmaceutical composition comprising the compound of Formula (I), or an isotopic variant, tautomer, pharmaceutically acceptable salt, solvate, or hydrate thereof is administered to the eye of the subject. In some embodiments, about 0.01 mg/mL to about 4.0 mg/mL of a pharmaceutical composition comprising the compound of Formula (I), or an isotopic variant, tautomer, pharmaceutically acceptable salt, solvate, or hydrate thereof is administered to the eye of the subject.

In some embodiments, the composition is administered the subject once per day, twice per day, three times per day, or four times per day.

In some embodiments, the composition is administered the subject three times per day. In some embodiments, about 60 μL of a pharmaceutical composition comprising the compound of Formula (I), or an isotopic variant, tautomer, pharmaceutically acceptable salt, solvate, or hydrate thereof is administered to the eye of the subject.

In some embodiments, the administration is topical or by ophthalmic injection. In some embodiments, the ophthalmic injection is an intravitreous or subconjunctival injection.

In an aspect, provided herein is a method of preparing a pharmaceutical composition, comprising a compound of Formula (I), or an isotopic variant, tautomer, pharmaceutically acceptable salt, solvate, or hydrate thereof; and at least one pharmaceutically acceptable excipient, wherein the pharmaceutical composition is formulated as a suspension, comprising:

(i) micronizing the compound of Formula (I), or an isotopic variant, tautomer, pharmaceutically acceptable salt, solvate, or hydrate thereof;

(ii) sterilizing the micronized compound of Formula (I), or an isotopic variant, tautomer, pharmaceutically acceptable salt, solvate, or hydrate thereof; and (iii) admixing a therapeutically effective amount of the compound of Formula (I), or an isotopic variant, tautomer, pharmaceutically acceptable salt, solvate, or hydrate thereof with the least one pharmaceutically acceptable excipients.

In an aspect, provided herein is a method of preparing a pharmaceutical composition, comprising fine particles of a compound of Formula (I), or an isotopic variant, tautomer, pharmaceutically acceptable salt, solvate, or hydrate thereof; and at least one pharmaceutically acceptable excipient, wherein the pharmaceutical composition is in a dosage form for ophthalmic dosing or administration, comprising:

(i) micronizing the compound of Formula (I), or an isotopic variant, tautomer, pharmaceutically acceptable salt, solvate, or hydrate thereof;

(ii) sterilizing the micronized compound of Formula (I), or an isotopic variant, tautomer, pharmaceutically acceptable salt, solvate, or hydrate thereof; and (iii) admixing a therapeutically effective amount of the compound of Formula (I), or an isotopic variant, tautomer, pharmaceutically acceptable salt, solvate, or hydrate thereof with the least one pharmaceutically acceptable excipients.

In some embodiments, a suspension comprising particles of the compound of Formula (I), or an isotopic variant, tautomer, pharmaceutically acceptable salt, solvate, or hydrate thereof is formed.

In some embodiments, the sterilization is performed before the admixing. In some embodiments, the sterilization is performed after the admixing.

In some embodiments, the sterilization is performed at a temperature of about 121° C. In some embodiments, the sterilization is performed for a period of from about 20 to about 30 minutes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

Figure 1:
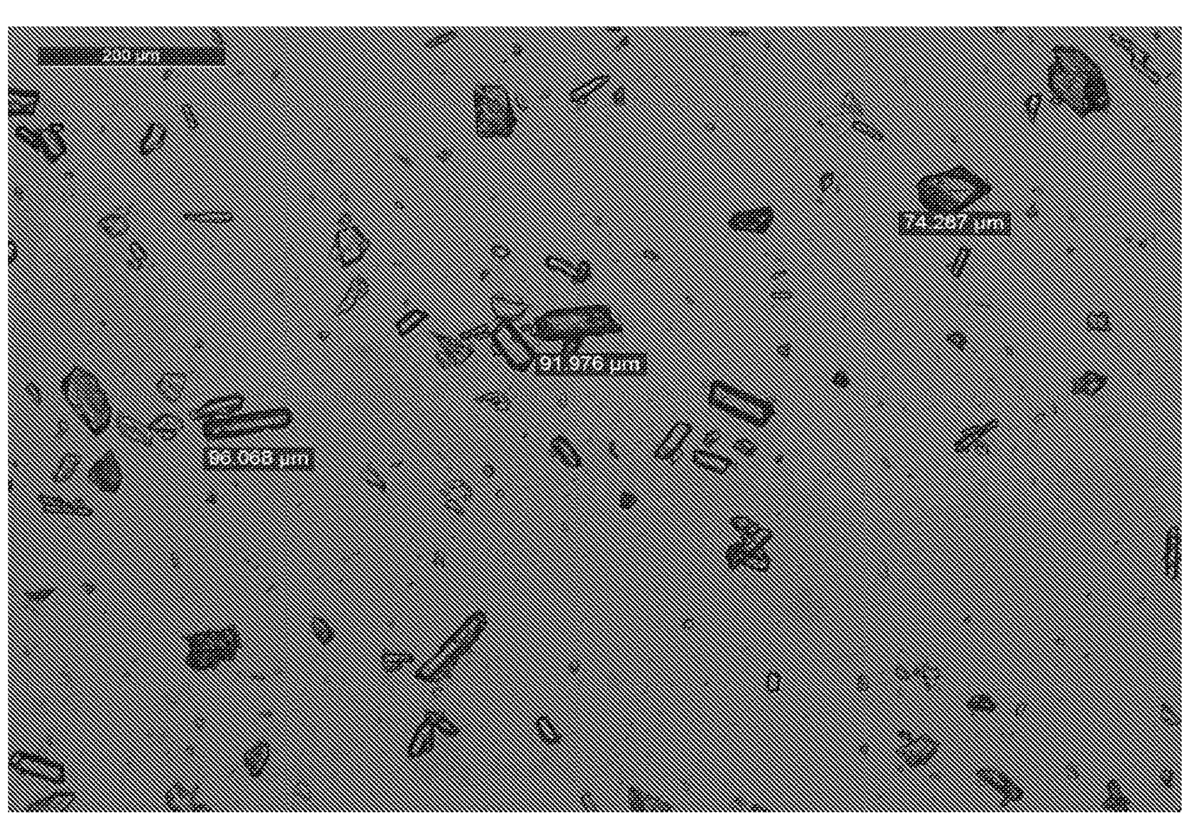
FIG. 1. is a microscopic image of KDR2-2 API (100× magnification), batch #CDK0120554-02-03P-01-32-01.
Figure 2:
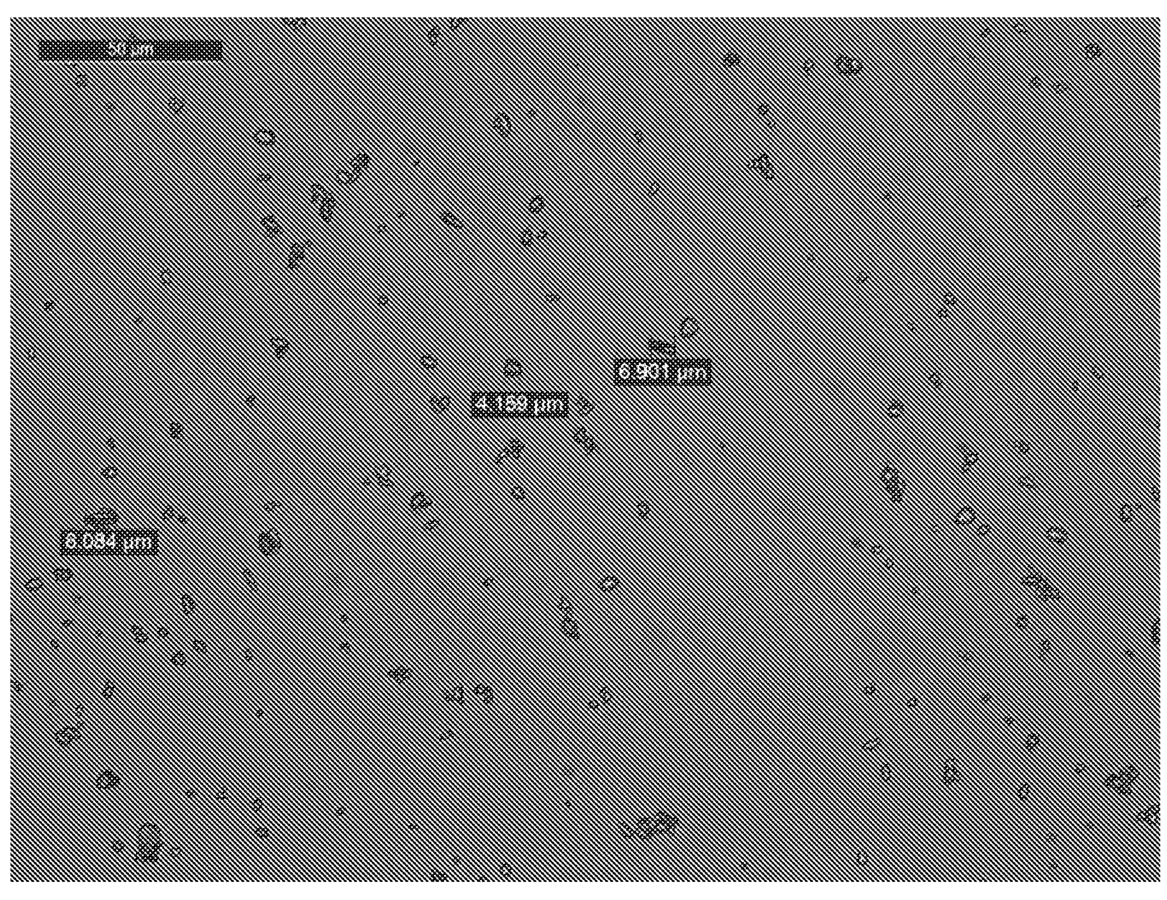
FIG. 2. is a microscopic image of KDR2-2 API after pulverization (400× magnification), batch #CKol20554-02-03P-01-32-01.
Figure 3:
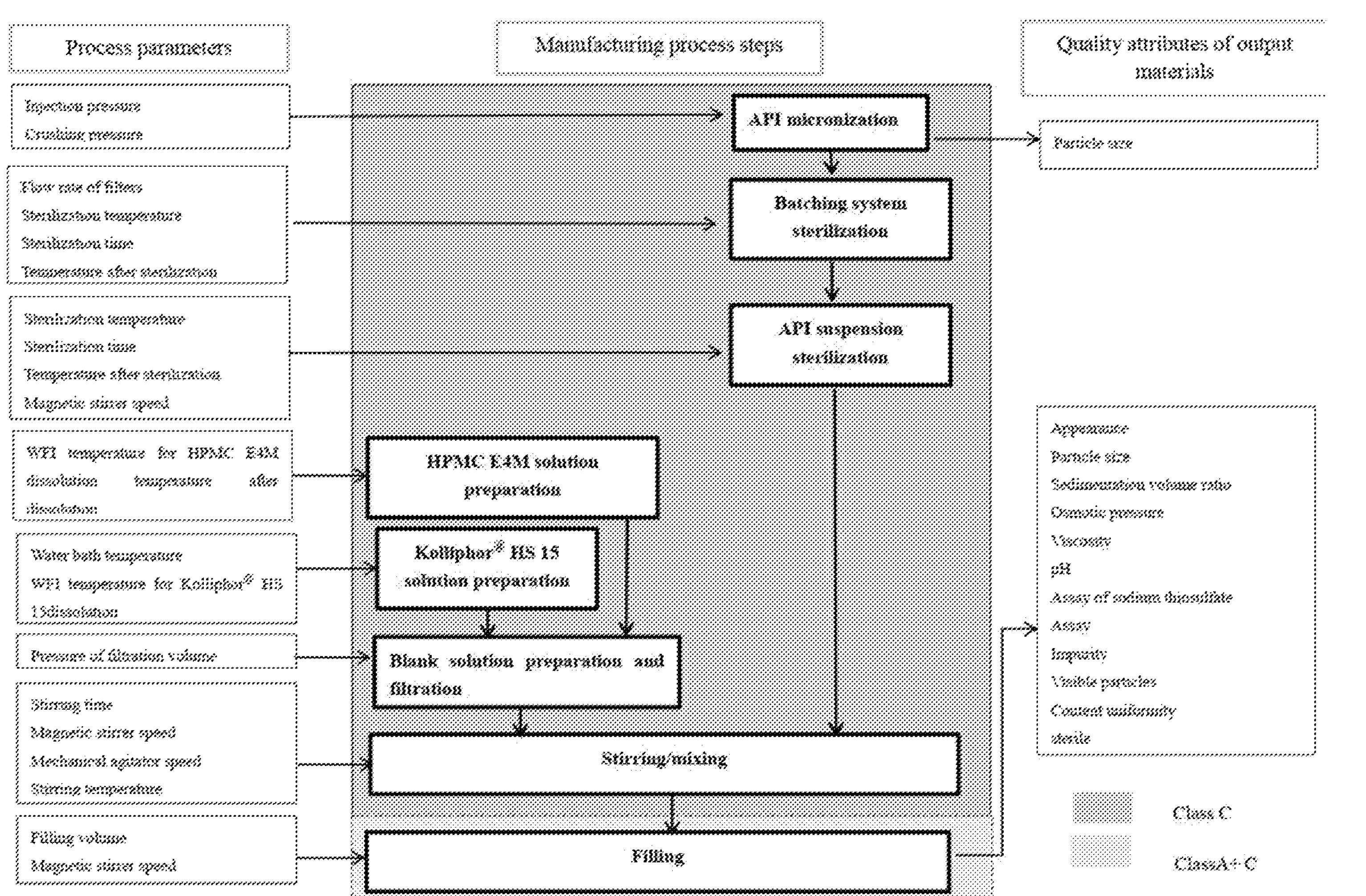
FIG. 3. schematically depicts the manufacturing process for KDR2-2 Suspension EyeDrop, 0.1% w/v.

Provided herein are, for example, compositions for treating and/or preventing an ophthalmic disorder or disease. Also provided herein are, for example, methods of treating and/or preventing an ophthalmic disorder or disease.

I. DEFINITIONS

The abbreviations used herein have their conventional meaning within the chemical and biological arts. The chemical structures and formulae set forth herein are constructed according to the standard rules of chemical valency known in the chemical arts.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are encompassed within the scope of the present invention.

The term "isotopic variant" refers to a compound that contains an unnatural proportion of an isotope at one or more of the atoms that constitute such a compound. In some embodiments, an "isotopic variant" of a compound contains unnatural proportions of one or more isotopes, including, but not limited to, hydrogen ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 (180), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$) iodine-125 ($^{125}I$), iodine-127 ($^{127}I$), iodine-129 ($^{129}I$), and iodine-131 ($^{131}I$). In some embodiments, an "isotopic variant" of a compound is in a stable form, that is, non-radioactive. In some embodiments, an "isotopic variant" of a compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In some embodiments, an "isotopic variant" of a compound is in an unstable form, that is, radioactive. In some embodiments, an "isotopic variant" of a compound contains unnatural proportions of one or more isotopes, including, but not limited to, tritium (3H), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36

($^{36}Cl$), iodine-123 ($^{123}I$) iodine-125 ($^{125}I$), iodine-129 ($^{129}I$), and iodine-131 ($^{131}I$). It will be understood that, in a compound as provided herein, any hydrogen can be $^{2}H$, for example, or any carbon can be $^{13}C$, for example, or any nitrogen can be $^{15}N$, for example, or any oxygen can be $^{18}O$, for example, where feasible according to the judgment of one of skill. In some embodiments, an "isotopic variant" of a compound contains unnatural proportions of deuterium (D).

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein, mean one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

The term "acceptable" with respect to a formulation, composition or ingredient, as used herein, means having no persistent detrimental effect on the general health of the subject being treated.

The term "pharmaceutically acceptable salt" as used herein includes both acid and base addition salts, i.e., including salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts," *Journal of Pharmaceutical Science,* 1977, 66, 1-19). Certain specific compounds of the present invention contain both basic and acidic functionalities that allow the compounds to be converted into either base or acid addition salts, or to exist as Zwitterions.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In some embodiments, compounds of the present invention contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of a compound to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "disease" or "condition" refer to a state of being or health status of a patient or subject capable of being treated with the compounds or methods provided herein. The disease may be an ophthalmic disease.

The terms "treating" or "treatment" refer to any indicia of success in therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof may include prevention of an injury, pathology, condition, or disease. In some embodiments, treating is preventing. In other embodiments, treating does not include preventing.

"Treating," "treatment," "palliating," or "ameliorating" are used interchangeably herein. These terms as used herein (and as well-understood in the art) also broadly include any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment," as used herein, includes any cure, amelioration, or prevention of a disease. Treatment may prevent the disease from occurring; inhibit the disease's spread; relieve the disease's symptoms (e.g., itching, swelling, burning, cough, fever, chest pain, difficulty breathing), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and duration sufficient to treat the patient.

The terms "prevent," "preventing," and "prevention" refer to a decrease in the occurrence of disease symptoms in a patient. The preventing or prevention may be complete (no detectable symptoms) or partial, such that fewer symptoms are observed than would likely occur absent treatment. In some embodiments, prevent refers to slowing the progression of the disease, disorder or condition or inhibiting progression thereof to a harmful or otherwise undesired state.

The terms "patient" or "subject in need thereof" refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals including, but not limited to, fish and birds. In some embodiments, a patient is human.

Treatment, as referred to herein, also refers to the systemic delivery of the compounds disclosed herein to any type of plant, including trees, shrubs, flowering plants, foliage plants, house plants, groundcover and grass, and agronomic plants (including crops of agronomic plants).

As used herein, "hydrates" are compounds that contain either stoichiometric or non-stoichiometric amounts of water, and, in some embodiments, are formed during the process of crystallization with water.

As used herein, the term "agronomic plant" refers to a plant of which a part or all is, or has been, harvested or cultivated on a commercial scale, or serves as an important source of feed, food, fiber, or other chemical compounds.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a compound of Formula (I) or an isotopic variant, tautomer, pharmaceutically acceptable salt, solvate, or hydrate thereof (or, e.g., a metabolite thereof) at a particular time post-administration may be indicative of whether a therapeutically effective amount has been administered.

For any compound described herein, therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means parenteral or enteral administration. Accordingly, as used herein, "administering" refers to administration including, but not limited to, oral administration, administration as a suppository, topical contact, intravenous, intraperitoneal, intramuscular, inhalation, nebulization, intralesional, intrathecal, intracranial, intranasal, subcutaneous administration, or the implantation of a slow-release device, e.g., a mini-osmotic pump, to a subject. Administration is by any route, including transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, by ocular route, by otic route, etc. By "co-administer" it is meant that a composition described herein is administered at the same time, just prior to, or just after the administration of one or more additional therapies. The compound of the invention can be administered alone or can be co-administered to the patient. Co-administration is meant to include simultaneous, approximately simultaneous, or sequential administration of the compound individually or in combination (more than one compound or agent). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

By "co-administer" it is meant that a composition described herein is administered at the same time, just prior to, or just after the administration of one or more additional therapies. The compounds of the invention can be administered alone or can be co-administered to the patient.

Co-administration is meant to include simultaneous or sequential administration of the compounds individually or in combination (more than one compound). The compositions of the present invention can be delivered transdermally, by a topical route, or formulated as applicator sticks, solutions, suspensions, emulsions, gels, creams, ointments, pastes, jellies, paints, powders, and aerosols.

For any compound described herein, therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

"Substantially pure" indicates that a component makes up greater than about 75% of the total content of the composition excluding excipients, and typically greater than about 85% of the total content. More typically, "substantially pure" refers to compositions in which at least 90%, at least 95%, at least 96%, at least 97% or more of the total composition excluding excipients is the component of interest. In some cases, the component of interest will make up greater than about 90%, greater than about 95%, or greater than about 96% of the total content of the composition excluding excipients (percentage in a weight per weight basis). "Substantially pure" indicates that the composition contains less than, up to, or no more than about 25%, 15%, 10%, 5%, or 4% of known or unknown impurities. Impurities do not include excipients (e.g., binders, fillers, diluents, glidants, lubricants, disintegrants, etc.)

"Angiogenesis" as used herein refers to the process through which new blood vessels form from pre-existing vessels. "Neovascularization" refers to the formation of new blood vessels, usually in the form of functional microvascular networks, capable of perfusion by red blood cells, which serve as collateral circulation in response to local poor perfusion or ischemia. Neovascularization is conventionally distinguished from angiogenesis in that angiogenesis is mainly characterized by the protrusion and outgrowth of capillary buds and sprouts from pre-existing blood vessels.

As used herein, the terms "corneal angiogenesis" and "corneal neovascularization" refer to the process of formation of new vessels originate and the corneal vessels extending from the limbus to the adjacent corneal stroma. Because the cornea is avascular, which does not contain any blood vessels, any new blood vessels in the cornea typically arise from the growth of blood vessels from the limbal vascular plexus area of the eye into the cornea.

"Choroidal neovascularization" refers to the formation of new vessels originating in the choroid, and can access the subretinal space through rupture of Bruch's membrane in the retinal pigment epithelium.

"Retinal neovascularization" refers to the formation of new vessels originate Retinal vessel and extending into the vitreous from the retinal surface.

"Iris neovascularization" is a medical condition of the iris of the eye in which new abnormal blood vessels (formed by neovascularization) are found on the surface of the iris. This condition is often associated with diabetes in advanced proliferative diabetic retinopathy. Other conditions causing rubeosis iridis include central retinal vein occlusion, ocular ischemic syndrome, and chronic retinal detachment.

Macular degeneration, also referred to as retinal degeneration, is a disease of the eye that involves deterioration of the macula, the central portion of the retina. Unless specified, the "macular degeneration" of the present disclosure includes all forms of the disease.

"Wet macular degeneration" also known as the neovascular or exudative form of macular degeneration in which new blood vessels form (i.e., neovascularization) to improve the blood supply to retinal tissue, specifically beneath the macula, a portion of the retina that is responsible for our sharp central vision. The new vessels are easily damaged and sometimes rupture, causing bleeding and injury to the surrounding tissue. Wet macular degeneration accounts for approximately 90% of macular degeneration-related blindness. Neovascularization can lead to rapid loss of vision and eventual scarring of the retinal tissues and bleeding in the eye. This scar tissue and blood produces a dark, distorted area in the vision, often rendering the eye legally blind. Wet macular degeneration usually starts with distortion in the central field of vision. Straight lines become wavy. Subjects with wet macular degeneration also report having blurred vision and blank spots (scotoma) in their visual field.

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm3, e.g., Avicel, powdered cellulose), and talc.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes. Many nonionic surfactants are known that are acceptable for topical ophthalmic formulations. Such surfactants include: tyloxapol; polyoxyethylene sorbitan esters, such as polysorbate 80, polysorbate 60, and polysorbate 20; polyethoxylated castor oils, such as Cremophore EL; polyethoxylated hydrogenated castor oils, such as HCO-40; and poloxamers.

The term "carrier," as used herein, refers to relatively nontoxic chemical compounds or agents that facilitate the incorporation of a compound into cells or tissues.

"Carrier materials" include any commonly used excipients in pharmaceutics and should be selected on the basis of compatibility with compounds disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

The compositions of the present invention are formulated to be isotonic, relative to the natural tear fluids. The compositions are therefore formulated to have an osmolality of about 280 to 320 milliosmoles per kilogram water ("mOsm/kg"). If necessary, the compositions may contain ophthalmically acceptable tonicity-adjusting agents, such as sodium chloride, potassium chloride, glycerin, sorbitol or mannitol. In some embodiments, the ophthalmic composition further comprises a tonicity adjusting agent. In some embodiments, the tonicity adjusting agent is selected from sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some embodiments, the composition is stored in a plastic container. In some embodiments, the material of the plastic container comprises low-density polyethylene (LDPE).

In some embodiments, the composition further comprises a pH adjusting agent. In some embodiments, the ophthalmically acceptable carrier further comprises at least one viscosity-enhancing agent. In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, or combinations thereof.

I. COMPOSITIONS

In an aspect, provided herein is a pharmaceutical composition, comprising:

(i) a compound of Formula (I):

(I)

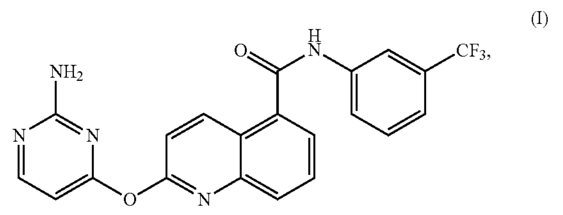 [SMILES: Nc1nccc(Oc2ccc3c(C(=O)Nc4cccc(C(F)(F)F)c4)cccc3n2)n1]

or an isotopic variant, tautomer, pharmaceutically acceptable salt, solvate, or hydrate thereof, and (ii) at least one pharmaceutically acceptable excipient, wherein the pharmaceutical composition is in a dosage form for ophthalmic dosing or administration.

In some embodiments, the dosage form is a suspension comprising fine particles of a compound of Formula (I), or an isotopic variant, tautomer, pharmaceutically acceptable salt, solvate, or hydrate thereof.

In an aspect, provided herein is a pharmaceutical composition, comprising:

(i) fine particles of a compound of Formula (I):

(I)

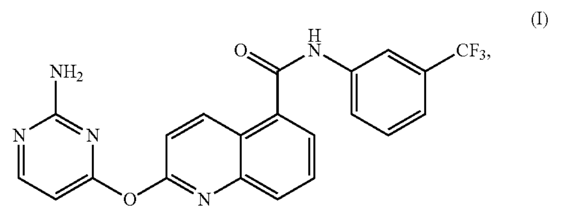 [SMILES: Nc1nccc(Oc2ccc3c(C(=O)Nc4cccc(C(F)(F)F)c4)cccc3n2)n1]

or an isotopic variant, tautomer, pharmaceutically acceptable salt, solvate, or hydrate thereof; and (ii) at least one pharmaceutically acceptable excipient, wherein the pharmaceutical composition is formulated as a suspension, a gel, or an ointment. In some embodiments, the pharmaceutical composition is formulated as a suspension.

In some embodiments, the particles are micronized.

In some embodiments, the particles of the compound of Formula (I), or an isotopic variant, tautomer, pharmaceutically acceptable salt, solvate, or hydrate thereof have a diameter of from about 0.1 μm to about 40 μm. In some embodiments, the particles of the compound of Formula (I), or an isotopic variant, tautomer, pharmaceutically acceptable salt, solvate, or hydrate thereof have a diameter of from about 0.1 μm to about 10 μm. In some embodiments, the particles of the compound of Formula (I), or an isotopic variant, tautomer, pharmaceutically acceptable salt, solvate, or hydrate thereof have a diameter of from about 0.3 μm to about 5 μm.

In some embodiments, at least about 10% of the particles have a diameter of from about 0.1 μm to about 40 μm. In some embodiments, at least about 20% of the particles have a diameter of from about 0.1 μm to about 40 μm. In some embodiments, at least about 30% of the particles have a diameter of from about 0.1 μm to about 40 μm. In some embodiments, at least about 40% of the particles have a diameter of from about 0.1 μm to about 40 μm. In some embodiments, at least about 50% of the particles have a diameter of from about 0.1 μm to about 40 μm. In some embodiments, at least about 60% of the particles have a diameter of from about 0.1 μm to about 40 μm. In some embodiments, at least about 70% of the particles have a diameter of from about 0.1 μm to about 40 μm. In some embodiments, at least about 80% of the particles have a diameter of from about 0.1 μm to about 40 μm. In some embodiments, at least about 90% of the particles have a diameter of from about 0.1 μm to about 40 μm. In some embodiments, at least about 95% of the particles have a diameter of from about 0.1 μm to about 40 μm.

In some embodiments, the particles have a D10 value of less than about 0.5 μm. In some embodiments, the particles have a D10 value of less than about 1 μm. In some embodiments, the particles have a D10 value of less than about 1.5 μm. In some embodiments, the particles have a D10 value of less than about 0.5, about 0.6, about 0.7, about 0.8, about 0.9, about 1.0, about 1.1, about 1.2, about 1.3, about 1.4, or about 1.5 μm.

In some embodiments, the particles have a D50 value of less than about 2.5 μm. In some embodiments, the particles have a D50 value of less than about 5 μm. In some embodiments, the particles have a D50 value of less than about 7.5 μm. In some embodiments, the particles have a D50 value of less than about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5 μm.

In some embodiments, the particles have a D90 value of less than about 5 μm. In some embodiments, the particles have a D90 value of less than about 10 μm. In some embodiments, the particles have a D90 value of less than about 15 μm. In some embodiments, the particles have a D90 value of less than about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0 μm. In some embodiments, the particles have a D90 value of less than about 5, about 6, about 7, about 8, about 9, about 10, about 11, about 12, about 13, about 14, or about 15 μm.

In some embodiments, the compound of Formula (I) or an isotopic variant, tautomer, pharmaceutically acceptable salt, solvate, or hydrate thereof; is crystalline, microcrystalline, amorphous, or lyophilized.

In some embodiments, the dosage form is a modified-release dosage form. In some embodiments, the modified-release dosage form is a delayed-release dosage form, an extended-release (ER) dosage form, or a targeted-release dosage form. In some embodiments, the ER dosage form is a sustained-release (SR) dosage form or controlled-release (CR) dosage form. In some embodiments, the composition comprises from about 0.025% to about 2.0% w/v of a compound of Formula (I), or an isotopic variant, tautomer, pharmaceutically acceptable salt, solvate, or hydrate thereof. In some embodiments, the composition comprises from about 0.05% to about 0.5% w/v of a compound of Formula (I), or an isotopic variant, tautomer, pharmaceutically acceptable salt, solvate, or hydrate thereof. In some embodiments, the composition comprises from about 0.05% to about 0.15% w/v of a compound of Formula (I), or an isotopic variant, tautomer, pharmaceutically acceptable salt, solvate, or hydrate thereof.

In some embodiments, the at least one pharmaceutically acceptable excipient is a diluent, buffering agent, suspending agent, solubilizer, emulsifier, antioxidant, pH adjusting agent, preservative, detackifier, anti-foaming agent, chelating agent, thickening agent, viscomodulator, tonicifier, colorant, opacifier, binder, filler, plasticizer, or any combination thereof. In some embodiments, the at least one pharmaceutically acceptable excipient is a suspending agent, a wetting agent, a pH adjuster, an anti-oxidant, an osmotic pressure regulator, or any combination thereof.

In some embodiments, the suspending agent is a polymer. In some embodiments, the suspending agent is a carbomer homopolymer, carbomer copolymer, carbomer interpolymer, polycarbophil, a cellulose derivative, a polyvinyl alcohol, a povidone, a hyaluronic acid or a salt thereof, chondroitin sulfate, a natural gum, or any combination thereof. In some embodiments, the cellulose derivative is hydroxypropyl methylcellulose, hydroxyethyl cellulose, hydroxypropyl cellulose, or any combination thereof. In some embodiments, the hydroxypropyl methylcellulose (HPMC) is K100, K4M, K15M, K100M, E4M, E10M, or any combination thereof. In some embodiments, the suspending agent is hydroxypropyl methylcellulose (HPMC). In some embodiments, the hypromellose is HPMC E4M.

In some embodiments, the concentration of the suspending agent in the compositions is up to about 1% w/w. In some embodiments, the concentration of the suspending agent in the formulation is up to about 0.5% w/w.

In some embodiments, the solubilizer is Kolliphor® ELP, Kolliphor® HS 15, or a combination thereof. In some embodiments, the solubilizer is Kolliphor® HS 15.

In some embodiments, the concentration of the solubilizer in the composition is up to about 5% w/w.

In some embodiments, the wetting agent is polyoxyl 15-hydroxystearate.

In some embodiments, the pH adjuster is a buffer. In some embodiments, the buffer is a phosphate buffer or a hydrate thereof. In some embodiments, the phosphate buffer is potassium phosphate or a hydrate thereof. In some embodiments, the phosphate buffer is sodium dihydrogen phosphate dihydrate ($NaH_2PO_4 \cdot 2H_2O$), di-sodium hydrogen phosphate dodecahydrate ($Na_2HPO_4 \cdot 12H_2O$), or a combination thereof.

In some embodiments, the osmotic pressure regulator is a salt. In some embodiments, the salt is sodium chloride.

In some embodiments, the concentration of the osmotic pressure regulator in the composition is up to about 0.5% w/w.

In some embodiments, the anti-oxidant is a thiosulfate. In some embodiments, the thiosulfate is sodium thiosulfate.

In some embodiments, the concentration of the anti-oxidant in the composition is up to about 0.2% w/w.

In some embodiments, the composition is stable for up to 24 months at a temperature of from about 20° C. to about 25° C.

In some embodiments, the composition is substantially free of impurities.

In some embodiments, the composition is at least about 90% pure. In some embodiments, the composition is at least about 95% pure. In some embodiments, the composition is at least about 96% pure. In some embodiments, the composition is at least about 97% pure. In some embodiments, the composition is at least about 98% pure. In some embodiments, the composition is at least about 99% pure. In some embodiments, the composition is at least about 99.1%, about 99.2%, about 99.3%, about 99.4%, about 99.5%, about 99.6%, about 99.7%, about 99.8%, about 99.9%, or about 100% pure.

In some embodiments, the composition comprises up to about 2% w/w of total impurities.

In some embodiments, the composition comprises less than about 0.9% w/w, about 0.8% w/w, about 0.7% w/w, about 0.6% w/w, about 0.5% w/w, about 0.4% w/w, about 0.3% w/w, about 0.2% w/w, or about 0.1% w/w of total impurities.

In some embodiments, the impurity is a degradant.

In some embodiments, the impurity comprises the compound of Formula (II):

(II)

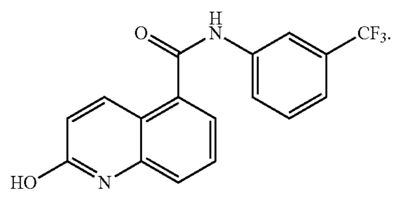

In some embodiments, the composition comprises up to about 2.0% w/w of any individual impurity.

In some embodiments, the composition has a pH of from about 4.0 to about 9.0. In some embodiments, the composition has a pH of from about 5.0 to about 8.0. In some embodiments, the composition has a pH of from about 6.5 to about 8.0. In some embodiments, the composition has a pH of from about 7.0 to about 8.0.

Antimicrobial agents such as antibiotics or anti-fungal agents may be added. Other substances can be added to the compositions to stabilize and/or preserve the compositions. The material can be packaged and stored, for example, at room temperature, or for example, at −20° C. or −80° C. prior to use.

In some aspects, described herein are formulations that do not have a dose-to-dose variation.

In some embodiments, the temperature of the storage condition is between about 20° C. and about 70° C. In some embodiments, the temperature of the storage condition is between about 25° C. and about 65° C., about 30° C. and about 60° C., about 35° C. and about 55° C., or about about 40° C. and about 50° C. In some embodiments, the temperature of the storage condition is about 25° C. In some embodiments, the temperature of the storage condition is about 40° C. In some embodiments, the temperature of the storage condition is about 60° C.

In some embodiments, the relative humidity of the storage condition is between about 50% and about 80%, or between about 60% and about 75%. In some embodiments, the relative humidity of the storage condition is about 60%. In some embodiments, the relative humidity of the storage condition is about 75%.

In some embodiments, the composition has a pH of from about 4.0 to about 9.0. In some embodiments, the composition has a pH of from about 5.0 to about 8.0. In some embodiments, the composition has a pH of from about 6.5 to about 8.0. In some embodiments, the composition has a pH of from about 7.0 to about 8.0.

In some embodiments, the composition has a pH of less than about 9. In some embodiments, the composition has a pH of less than about 8.9. In some embodiments, the composition has a pH of less than about 8.8. In some embodiments, the composition has a pH of less than about 8.7. In some embodiments, the composition has a pH of less than about 8.6. In some embodiments, the composition has a pH of less than about 8.5. In some embodiments, the composition has a pH of less than about 8.4. In some embodiments, the composition has a pH of less than about 8.3. In some embodiments, the composition has a pH of less than about 8.2. In some embodiments, the composition has a pH of less than about 8.1.

In some embodiments, the composition has a pH of less than about 8.0. In some embodiments, the composition has a pH of less than about 7.9. In some embodiments, the composition has a pH of less than about 7.8. In some embodiments, the composition has a pH of less than about 7.7. In some embodiments, the composition has a pH of less than about 7.6. In some embodiments, the composition has a pH of less than about 7.5. In some embodiments, the composition has a pH of less than about 7.4. In some embodiments, the composition has a pH of less than about 7.3. In some embodiments, the composition has a pH of less than about 7.2. In some embodiments, the composition has a pH of less than about 7.1. In some embodiments, the composition has a pH of less than about 7.0. In some embodiments, the composition comprises less than 2.0% of primary degradant based on the concentration of the ophthalmic agent after extended period of time under storage condition. In some embodiments, the composition comprises less than 1.5% of primary degradant based on the concentration of the ophthalmic agent after extended period of time under storage condition. In some embodiments, the composition comprises less than 1.0% of primary degradant based on the concentration of the ophthalmic agent after extended period of time under storage condition. In some embodiments, the composition comprises less than 0.5% of primary degradant based on the concentration of the ophthalmic agent after extended period of time under storage condition. In some embodiments, the composition comprises less than 0.4% of primary degradant based on the concentration of the ophthalmic agent after extended period of time under storage condition. In some embodiments, the composition comprises less than 0.3% of primary degradant based on the concentration of the ophthalmic agent after extended period of time under storage condition. In some embodiments, the composition comprises less than 0.2% of primary degradant based on the concentration of the ophthalmic agent after extended period of time under storage condition. In some embodiments, the composition comprises less than 0.1% of primary degradant based on the concentration of the ophthalmic agent after extended period of time under storage condition.

Aqueous Solution Stability

In some embodiments, the composition described herein comprises a buffer. In some embodiments, a buffer is selected from borates, borate-polyol complexes, phosphate buffering agents, citrate buffering agents, acetate buffering agents, carbonate buffering agents, organic buffering agents, amino acid buffering agents, or combinations thereof.

In some instances, borates include boric acid, salts of boric acid, other pharmaceutically acceptable borates, and combinations thereof. In some cases, borates include boric acid, sodium borate, potassium borate, calcium borate, magnesium borate, manganese borate, and other such borate salts.

As used herein, the term polyol includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. In some instances, examples of polyol include: sugars, sugar alcohols, sugar acids and uronic acids. In some cases, polyols include, but are not limited to: mannitol, glycerin, xylitol and sorbitol.

In some embodiments, phosphate buffering agents include phosphoric acid; alkali metal phosphates such as disodium hydrogen phosphate, sodium dihydrogen phosphate, trisodium phosphate, dipotassium hydrogen phosphate, potassium dihydrogen phosphate, and tripotassium phosphate; alkaline earth metal phosphates such as calcium phosphate, calcium hydrogen phosphate, calcium dihydrogen phosphate, monomagnesium phosphate, dimagnesium phosphate (magnesium hydrogen phosphate), and trimagnesium phosphate; ammonium phosphates such as diammonium hydrogen phosphate and ammonium dihydrogen phosphate; or a combination thereof. In some instances, the phosphate buffering agent is an anhydride. In some instances, the phosphate buffering agent is a hydrate.

In some embodiments, borate-polyol complexes include those described in U.S. Pat. No. 6,503,497. In some instances, the borate-polyol complexes comprise borates in an amount of from about 0.01 to about 2.0% w/v, and one or more polyols in an amount of from about 0.01% to about 5.0% w/v.

In some cases, citrate buffering agents include citric acid and sodium citrate.

In some instances, acetate buffering agents include acetic acid, potassium acetate, and sodium acetate.

In some instances, carbonate buffering agents include sodium bicarbonate and sodium carbonate.

In some cases, organic buffering agents include Good's Buffer, such as for example 2-(N-morpholino)ethanesulfonic acid (MES), N-(2-Acetamido)iminodiacetic acid, N-(Carbamoylmethyl)iminodiacetic acid (ADA), piperazine-N,N'-bis(2-ethanesulfonic acid (PIPES), N-(2-acetamido)-2-aminoethanesulfonic acid (ACES), β-Hydroxy-4-morpholinepropanesulfonic acid, 3-Morpholino-2-hydroxypropanesulfonic acid (MOPSO), cholamine chloride, 3-(N-morpholino)propansulfonic acid (MOPS), N,N-bis(2-hydroxyethyl)-2-aminoethanesulfonic acid (BES), 2-[(2-Hydroxy-1,1-bis(hydroxymethyl)ethyl)amino]ethanesulfonic acid (TES), 4-(2-hydroxyethyl)-1-piperazineethanesulfonic acid (HEPES), 3-(N,N-Bis[2-hydroxyethyl]amino)-2-hydroxypropanesulfonic acid (DIPSO), acetamidoglycine, 3-{[1,3-Dihydroxy-2-(hydroxymethyl)-2-propanyl]amino}-2-hydroxy-1-propanesulfonic acid (TAPSO), piperazine-1,4,-bis(2-hydroxypropanesulphonic acid) (POPSO), 4-(2-hydroxyethyl)piperazine-1-(2-hydroxypropanesulfonic acid) hydrate (HEPPSO), 3-[4-(2-hydroxyethyl)-1-piperazinyl]propanesulfonic acid (HEPPS), tricine, glycinamide, bicine or N-tris(hydroxymethyl)methyl-3-aminopropanesulfonic acid sodium (TAPS); glycine; and diethanolamine (DEA).

In some cases, amino acid buffering agents include taurine, aspartic acid and its salts (e.g., potassium salts, etc), E-aminocaproic acid, and the like.

In some instances, the compositions described herein further comprise a tonicity adjusting agent. Tonicity adjusting agent is an agent introduced into a preparation such as an ophthalmic composition to reduce local irritation by preventing osmotic shock at the site of application. In some instances, buffer solution and/or a pH adjusting agent that broadly maintains the ophthalmic solution at a particular ion concentration and pH are considered as tonicity adjusting agents. In some cases, tonicity adjusting agents include various salts, such as halide salts of a monovalent cation. In some cases, tonicity adjusting agents include mannitol, sorbitol, dextrose, sucrose, urea, and glycerin. In some instances, suitable tonicity adjustors comprise sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some instances, the concentration of the tonicity adjusting agent in a composition described herein is between about 0.5% and about 2.0%. In some instances, the concentration of the tonicity adjusting agent in a composition described herein is between about 0.7% and about 1.8%, about 0.8% and about 1.5%, or about 1% and about 1.3%. In some instances, the concentration of the tonicity adjusting agent is about 0.6%, 0.7%, 0.8%, 0.9%, 1.0%, 1.1%, 1.2%, 1.3%, 1.4%, 1.5%, 1.6%, 1.7%, 1.8%, or 1.9%. In some cases, the percentage is a weight percentage.

In some cases, the composition described herein further comprises a pH adjusting agent. The pH adjusting agent is used which can be acid or base. The base can be oxides, hydroxides, carbonates, bicarbonates and the likes. The oxides can be metal oxides such as calcium oxide, magnesium oxide and the likes; hydroxides can be of alkali metals and alkaline earth metals such as sodium hydroxide, potassium hydroxide, calcium hydroxide and the likes and carbonates can be sodium carbonate, sodium bicarbonates, potassium bicarbonates and the likes. The acid can be mineral acid and organic acids such as hydrochloric acid, nitric acid, phosphoric acid, acetic acid, citric acid, fumaric acid, malic acid tartaric acid and the likes. In some instances, the pH adjusting agent includes, but is not limited to, acetate, bicarbonate, ammonium chloride, citrate, phosphate, pharmaceutically acceptable salts thereof and combinations or mixtures thereof.

As described elsewhere herein, the composition has a pH of from about 4.0 to about 9.0. In some embodiments, the composition has a pH of from about 5.0 to about 8.0. In some embodiments, the composition has a pH of from about 6.5 to about 8.0. In some embodiments, the composition has a pH of from about 7.0 to about 8.0.

In some embodiments, the composition has a pH of more than about 5.0. In some embodiments, the composition has a pH of more than about 4.9. In some embodiments, the composition has a pH of more than about 4.8. In some embodiments, the composition has a pH of more than about 4.7. In some embodiments, the composition has a pH of more than about 4.6. In some embodiments, the composition has a pH of more than about 4.5. In some embodiments, the composition has a pH of more than about 4.4. In some embodiments, the composition has a pH of more than about 4.3. In some embodiments, the composition has a pH of more than about 4.2. In some embodiments, the composition has a pH of more than about 4.1.

In some embodiments, the composition has a pH of more than about 6.0. In some embodiments, the composition has a pH of more than about 5.9. In some embodiments, the composition has a pH of more than about 5.8. In some embodiments, the composition has a pH of more than about 5.7. In some embodiments, the composition has a pH of more than about 5.6. In some embodiments, the composition has a pH of more than about 5.5. In some embodiments, the composition has a pH of more than about 5.4. In some embodiments, the composition has a pH of more than about 5.3. In some embodiments, the composition has a pH of more than about 5.2. In some embodiments, the composition has a pH of more than about 5.1.

In some embodiments, the composition has a pH of more than about 7.0. In some embodiments, the composition has a pH of more than about 6.9. In some embodiments, the composition has a pH of more than about 6.8. In some embodiments, the composition has a pH of more than about 6.7. In some embodiments, the composition has a pH of more than about 6.6. In some embodiments, the composition has a pH of more than about 6.5. In some embodiments, the composition has a pH of more than about 6.4. In some embodiments, the composition has a pH of more than about 6.3. In some embodiments, the composition has a pH of more than about 6.2. In some embodiments, the composition has a pH of more than about 6.1.

In some embodiments, the composition has a pH of less than about 9.0. In some embodiments, the composition has a pH of less than about 8.9. In some embodiments, the composition has a pH of less than about 8.8. In some embodiments, the composition has a pH of less than about 8.7. In some embodiments, the composition has a pH of less than about 8.6. In some embodiments, the composition has a pH of less than about 8.5. In some embodiments, the composition has a pH of less than about 8.4. In some embodiments, the composition has a pH of less than about 8.3. In some embodiments, the composition has a pH of less than about 8.2. In some embodiments, the composition has a pH of less than about 8.1.

In some embodiments, the composition has a pH of less than about 8.0. In some embodiments, the composition has a pH of less than about 7.9. In some embodiments, the composition has a pH of less than about 7.8. In some embodiments, the composition has a pH of less than about 7.7. In some embodiments, the composition has a pH of less than about 7.6. In some embodiments, the composition has a pH of less than about 7.5. In some embodiments, the composition has a pH of less than about 7.4. In some embodiments, the composition has a pH of less than about 7.3. In some embodiments, the composition has a pH of less than about 7.2. In some embodiments, the composition has a pH of less than about 7.1. In some embodiments, the composition has a pH of less than about 7.0.

In some instances, the composition described herein further comprises a disinfecting agent. In some cases, disinfecting agents include polymeric biguanides, polymeric quarternary ammonium compounds, chlorites, bisbiguanides, chlorite compounds (e.g., potassium chlorite, sodium chlorite, calcium chlorite, magnesium chlorite, or mixtures thereof), and a combination thereof.

In some instances, the composition described herein further comprises a preservative. In some cases, a preservative is added at a concentration to a composition described herein to prevent the growth of or to destroy a microorganism introduced into the composition. In some instances, microorganisms refer to bacteria (e.g., *Proteus mirabilis, Serratia marcesens*), virus (e.g., Herpes simplex virus, herpes zoster virus), fungus (e.g. fungi from the genus *Fusarium*), yeast (e.g., *Candida albicans*), parasites (e.g., *Plasmodium* spp., *Gnathostoma* spp.), protozoan (e.g., *Giardia lamblia*), nematodes (e.g., *Onchocercus volvulus*), worm (e.g., *Dirofilaria immitis*), and/or amoeba (e.g., Acanthameoba).

In some instances, the concentration of the preservative is between about 0.0001% and about 1%, about 0.001% and about 0.8%, about 0.004% and about 0.5%, about 0.008% and about 0.1%, and about 0.01% and about 0.08%. In some cases, the concentration of the preservatives is about 0.001%, 0.002%, 0.003%, 0.004%, 0.005%, 0.006%, 0.008%, 0.009%, 0.009%, 0.01%, 0.015%, 0.02%, 0.025%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% or 1.0%.

In some embodiments, the preservative is selected from benzalkonium chloride, cetrimonium, sodium perborate, stabilized oxychloro complex, SofZia (Alcon), polyquaternium-1, chlorobutanol, edetate disodium, and polyhexamethylene biguanide.

In some embodiments, the composition described herein is stored in a plastic container. In some embodiments, the material of the plastic container comprises high density polyethylene (HDPE), low density polyethylene (LDPE), polyethylene terephthalate (PET), polyvinyl chloride (PVC), polyprolyene (PP), polystyrene (PS), fluorine treated HDPE, post consumer resin (PCR), K-resine (SBC), or bioplastic. In some embodiments, the material of the plastic container comprises LDPE.

In some embodiments, the composition described herein is stored in a plastic container.

In some embodiments, the composition stored in a plastic container has a pH of from about 4.0 to about 9.0. In some embodiments, the composition has a pH of from about 5.0 to about 8.0. In some embodiments, the composition stored in a plastic container has a pH of from about 6.5 to about 8.0. In some embodiments, the composition stored in a plastic container has a pH of from about 7.0 to about 8.0.

In some embodiments, the composition stored in a plastic container has a pH of less than about 9.0. In some embodiments, the composition stored in a plastic container has a pH of less than about 8.9. In some embodiments, the composition stored in a plastic container has a pH of less than about 8.8. In some embodiments, the composition stored in a plastic container has a pH of less than about 8.7. In some embodiments, the composition stored in a plastic container has a pH of less than about 8.6. In some embodiments, the composition stored in a plastic container has a pH of less than about 8.5. In some embodiments, the composition stored in a plastic container has a pH of less than about 8.4. In some embodiments, the composition stored in a plastic container has a pH of less than about 8.3. In some embodiments, the composition stored in a plastic container has a pH of less than about 8.2. In some embodiments, the composition stored in a plastic container has a pH of less than about 8.1.

In some embodiments, the composition stored in a plastic container has a pH of less than about 8.0. In some embodiments, the composition stored in a plastic container has a pH of less than about 7.9. In some embodiments, the composition stored in a plastic container has a pH of less than about 7.8. In some embodiments, the composition stored in a plastic container has a pH of less than about 7.7. In some embodiments, the composition stored in a plastic container has a pH of less than about 7.6. In some embodiments, the composition stored in a plastic container has a pH of less than about 7.5. In some embodiments, the composition stored in a plastic container has a pH of less than about 7.4. In some embodiments, the composition stored in a plastic container has a pH of less than about 7.3. In some embodiments, the composition stored in a plastic container has a pH of less than about 7.2. In some embodiments, the composition stored in a plastic container has a pH of less than about 7.1. In some embodiments, the composition has a pH of less than about 7.0.

In some embodiments, the composition stored in a plastic container has a potency of at least 80% after extended period of time under storage condition. In some embodiments, the composition stored in a plastic container has a potency of at least 85% after extended period of time under storage condition. In some embodiments, the composition stored in a plastic container has a potency of at least 90% after extended period of time under storage condition. In some embodiments, the composition stored in a plastic container has a potency of at least 93% after extended period of time under storage condition. In some embodiments, the composition stored in a plastic container has a potency of at least 95% after extended period of time under storage condition. In some embodiments, the composition stored in a plastic container has a potency of at least 97% after extended period of time under storage condition. In some embodiments, the composition stored in a plastic container has a potency of at least 98% after extended period of time under storage condition. In some embodiments, the composition stored in a plastic container has a potency of at least 99% after extended period of time under storage condition. In some instances, the storage condition comprises a temperature of about 25° C., about 40° C., or about 60° C. In some instances, the extended period of time is at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a plastic container has a potency of at least 80% at a temperature of about 25° C., about 40° C., or about 60° C. In some embodiments the composition stored in a plastic container has a potency of at least 85% at a temperature of about 25° C., about 40° C., or about 60° C. In some embodiments, the composition stored in a plastic container has a potency of at least 90% at a temperature of about 25° C., about 40° C., or about 60° C. In some embodiments, the composition stored in a plastic container has a potency of at least 93% at a temperature of about 25° C., about 40° C., or about 60° C. In some embodiments, the composition stored in a plastic container has a potency of at least 95% at a temperature of about 25° C., about 40° C., or about 60° C. In some embodiments, the composition stored in a plastic container has a potency of at least 97% at a temperature of about 25° C., about 40° C., or ab out 60° C. In some embodiments, the composition stored in a plastic container has a potency of at least 98% at a temperature of about 25° C., about 40° C., or about 60° C. In some embodiments, the composition stored in a plastic container has a potency of at least 99% at a temperature of about 25° C., about 40° C., or about 60° C.

In some embodiments, the composition stored in a plastic container has a potency of at least 80% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 85% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 90% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 93% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 95% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 97% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 98% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container has a potency of at least 99% for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a plastic container comprises less than 2.5% of primary degradant based on the concentration of the ophthalmic agent after extended period of time under storage condition. In some embodiments, the composition stored in a plastic container comprises less than 2.0% of primary degradant based on the concentration of the ophthalmic agent after extended period of time under storage condition. In some embodiments, the composition stored in a plastic container comprises less than 1.5% of primary degradant based on the concentration of the ophthalmic agent after extended period of time under storage condition. In some embodiments, the composition stored in a plastic container comprises less than 1.0% of primary degradant based on the concentration of the ophthalmic agent after extended period of time under storage condition. In some embodiments, the composition stored in a plastic container comprises less than 0.5% of primary degradant based on the concentration of the ophthalmic agent after extended period of time under storage condition. In some embodiments, the composition stored in a plastic container comprises less than 0.4% of primary degradant based on the concentration of the ophthalmic agent after extended period of time under storage condition. In some embodiments, the composition stored in a plastic container comprises less than 0.3% of primary degradant based on the concentration of the ophthalmic agent after extended period of time under storage condition. In some embodiments, the composition stored in a plastic container comprises less than 0.2% of primary degradant based on the concentration of the ophthalmic agent after extended period of time under storage condition. In some embodiments, the composition stored in a plastic container comprises less than 0.1% of primary degradant based on the concentration of the ophthalmic agent after extended period of time under storage condition. In some instances, the storage condition comprises a temperature of about 25 ° C., about 40° C., or about 60° C. In some instances, the extended period of time is at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition stored in a plastic container comprises less than 2.5% of primary degradant based on the concentration of the ophthalmic agent at a temperature of about 25° C., about 40° C., or about 60° C. In some embodiments, the composition stored in a plastic container comprises less than 2.0% of primary degradant based on the concentration of the ophthalmic agent at a temperature of about 25° C., about 40° C., or about 60° C. In some embodiments, the composition stored in a plastic container comprises less than 1.5% of primary degradant based on the concentration of the ophthalmic agent at a temperature of about 25° C., about 40° C., or about 60° C. In some embodiments, the composition stored in a plastic container comprises less than 1.0% of primary degradant based on the concentration of the ophthalmic agent at a temperature of about 25° C., about 40° C., or about 60° C. In some embodiments, the composition stored in a plastic container comprises less than 0.5% of primary degradant based on the concentration of the ophthalmic agent at a temperature of about 25° C., about 40° C., or about 60° C. In some embodiments, the composition stored in a plastic container comprises less than 0.4% of primary degradant based on the concentration of the ophthalmic agent at a temperature of about 25° C., about 40° C., or about 60° C. In some embodiments, the composition stored in a plastic container comprises less than 0.3% of primary degradant based on the concentration of the ophthalmic agent at a temperature of about 25° C., about 40° C., or about 60° C. In some embodiments, the composition stored in a plastic container comprises less than 0.2% of primary degradant based on the concentration of the ophthalmic agent at a temperature of about 25° C., about 40° C., or about 60° C. In some embodiments, the composition stored in a plastic container comprises less than 0.1% of primary degradant based on the concentration of the ophthalmic agent at a temperature of about 25° C., about 40° C., or about 60° C.

In some embodiments, the composition stored in a plastic container comprises less than 2.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 2.0% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 1.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 1.0% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.5% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.4% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.3% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.2% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months. In some embodiments, the composition stored in a plastic container comprises less than 0.1% of primary degradant based on the concentration of the ophthalmic agent for a period of at least 1 week, at least 2 weeks, at least 3 weeks, at least 1 month, at least 2 months, at least 3 months, at least 4 months, at least 5 months, at least 6 months, at least 8 months, at least 10 months, at least 12 months, at least 18 months, or at least 24 months.

In some embodiments, the composition described herein is stored in a glass container. In some embodiments, the glass container is a glass vial, such as for example, a type I, type II or type III glass vial. In some embodiments, the glass container is a type I glass vial. In some embodiments, the type I glass vial is a borasilicate glass vial.

In some embodiments, the composition stored in a glass container has a pH of from about 4.0 to about 9.0. In some embodiments, the composition has a pH of from about 5.0 to about 8.0. In some embodiments, the composition stored in a glass container has a pH of from about 6.5 to about 8.0. In some embodiments, the composition stored in a glass container has a pH of from about 7.0 to about 8.0.

In some embodiments, the composition stored in a glass container has a pH of less than about 9. In some embodiments, the composition stored in a glass container has a pH of less than about 8.9. In some embodiments, the composition stored in a glass container has a pH of less than about 8.8. In some embodiments, the composition stored in a glass container has a pH of less than about 8.7. In some embodiments, the composition stored in a glass container has a pH of less than about 8.6. In some embodiments, the composition stored in a glass container has a pH of less than about 8.5. In some embodiments, the composition stored in a glass container has a pH of less than about 8.4. In some embodiments, the composition stored in a glass container has a pH of less than about 8.3. In some embodiments, the composition stored in a glass container has a pH of less than about 8.2. In some embodiments, the composition stored in a glass container has a pH of less than about 8.1.

In some embodiments, the composition stored in a glass container has a pH of less than about 8.0. In some embodiments, the composition stored in a glass container has a pH of less than about 7.9. In some embodiments, the composition stored in a glass container has a pH of less than about 7.8. In some embodiments, the composition stored in a glass container has a pH of less than about 7.7. In some embodiments, the composition stored in a glass container has a pH of less than about 7.6. In some embodiments, the composition stored in a glass container has a pH of less than about 7.5. In some embodiments, the composition stored in a glass container has a pH of less than about 7.4. In some embodiments, the composition stored in a glass container has a pH of less than about 7.3. In some embodiments, the composition stored in a glass container has a pH of less than about 7.2. In some embodiments, the composition stored in a glass container has a pH of less than about 7.1. In some embodiments, the composition has a pH of less than about 7.0.

In some embodiments, the composition described herein is formulated as an aqueous solution. In some embodiments, the aqueous solution is a stable aqueous solution. In some instances, the aqueous solution is stored in a plastic container as described above. In some instances, the aqueous solution is not stored in a glass container. In some instances, the aqueous solution is stored in the dark. In some instances, the aqueous solution is stored in the presence of light. In some instances, the aqueous solution is stable in the presence of light.

Other stabilizers that are useful in the ophthalmically acceptable formulations disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the formulation, improves the mixing of various components in the formulation, controls the moisture level in the formula, or controls the mobility of the phase.

In other embodiments, stabilizers are present in sufficient amounts to inhibit the degradation of the ophthalmic agent. Examples of such stabilizing agents, include, but are not limited to: glycerol, methionine, monothioglycerol, EDTA, ascorbic acid, polysorbate 80, polysorbate 20, arginine, heparin, dextran sulfate, cyclodextrins, pentosan polysulfate and other heparinoids, divalent cations such as magnesium and zinc, or combinations thereof.

Additional useful stabilization agents for ophthalmically acceptable formulations include one or more anti-aggregation additives to enhance stability of ophthalmic formulations by reducing the rate of protein aggregation. The anti-aggregation additive selected depends upon the nature of the conditions to which the ophthalmic agents are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations optionally include one or more ophthalmically acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more ophthalmically acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the ophthalmically acceptable pharmaceutical formulations described herein are stable with respect to compound degradation (e.g. less than 30% degradation, less than 25% degradation, less than 20% degradation, less than 15% degradation, less than 10% degradation, less than 8% degradation, less than 5% degradation, less than 3% degradation, less than 2% degradation, or less than 5% degradation) over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, or at least about 6 months under storage conditions (e.g. room temperature). In other embodiments, the formulations described herein are stable with respect to compound degradation over a period of at least about 1 week. Also described herein are formulations that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof, c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzyl-ammonium chloride.

In a further embodiment, when one or more co-surfactants are utilized in the ophthalmically acceptable formulations of the present disclosure, they are combined, e.g., with a pharmaceutically acceptable vehicle and is present in the final formulation, e.g., in an amount ranging from about 0.1% to about 20%, from about 0.5% to about 10%.

In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

Aqueous Solution Dose-to-Dose Uniformity

Typical ophthalmic aqueous solutions are packaged in eye drop bottles and administered as drops. For example, a single administration (i.e., a single dose) of an ophthalmic aqueous solution may include a single drop, two drops, three drops or more into the eyes of the patient. In some embodiments, one dose of the ophthalmic aqueous solution described herein is one drop of the aqueous solution composition from the eye drop bottle.

In some cases, described herein include ophthalmic aqueous compositions which provide a dose-to-dose uniform concentrations. In some instances, the dose-to-dose uniform concentration does not present significant variations of drug content from one dose to another. In some instances, the dose-to-dose uniform concentration does provide consistant drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

A nonsettling formulation should not require shaking to disperse drug uniformly. A "no-shake" formulation is potentially advantageous over formulations that require shaking for the simple reason that patients' shaking behavior is a major source of variability in the amount of drug dosed. It has been reported that patients often times do not or forget to shake their ophthalmic compositions that requires shaking before administering a dose, despite the instructions to shake that were clearly marked on the label. On the other hand, even for those patients who do shake the product, it is normally not possible to determine whether the shaking is adequate in intensity and/or duration to render the product uniform. In some embodiments, the ophthalmic compositions described herein are "no-shake" formulations that maintained the dose-to-dose uniformity described herein.

To evaluate the dose-to-dose uniformity, drop bottles or tubes containing the ophthalmic (aqueous) compositions are stored upright for a minimum of 12 hours prior to the start of the test. To simulate the recommended dosing of these products, predetermined number of drops or strips are dispensed from each commercial bottles or tubes at predetermined time intervals for an extended period of time or until no product was left in the bottle or tube. All drops and strips are dispensed into tared glass vials, capped, and stored at room temperature until analysis. Aqueous Solution Viscosity In some embodiments, the composition has a Brookfield RVDV viscosity of from about 10 to about 50,000 cps at about 20° C. and sheer rate of 1 $s^{-1}$. In some embodiments, the composition has a Brookfield RVDV viscosity of from about 100 to about 40,000 cps at about 20° C. and sheer rate of 1 $s^{-1}$. In some embodiments, the composition has a Brookfield RVDV viscosity of from about 500 to about 30,000 cps at about 20° C. and sheer rate of 1 $s^{-1}$. In some embodiments, the composition has a Brookfield RVDV viscosity of from about 1000 to about 20,000 cps at about 20° C. and sheer rate of 1 $s^{-1}$. In some embodiments, the composition has a Brookfield RVDV viscosity of from about 2000 to about 10,000 cps at about 20° C. and sheer rate of 1 $s^{-1}$. In some embodiments, the composition has a Brookfield RVDV viscosity of from about 4000 to about 8000 cps at about 20° C. and sheer rate of 1 $s^{-1}$.

In some embodiments, the ophthalmic aqueous formulation contains a viscosity enhancing agent sufficient to provide a viscosity of between about 500 and 50,000 centipoise, between about 750 and 50,000 centipoise; between about 1000 and 50,000 centipoise; between about 1000 and 40,000 centipoise; between about 2000 and 30,000 centipoise;

between about 3000 and 20,000 centipoise; between about 4000 and 10,000 centipoise, or between about 5000 and 8000 centipoise.

pH

In some embodiments, the pH of a composition described herein is adjusted (e.g., by use of a buffer and/or a pH adjusting agent) to an ophthalmically compatible pH range of from about 4.0 to about 9.0. In some embodiments, the ophthalmic composition has a pH of from about 5.0 to about 8.0. In some embodiments, the ophthalmic composition has a pH of from about 6.5 to about 8.0. In some embodiments, the ophthalmic composition has a pH of from about 7.0 to about 8.0.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the formulations is such that the pH of the formulation does not interfere with the body's natural buffering system.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In some embodiments, the ophthalmic composition described herein has a pH of from about 4.0-9.0, from about 5.0 to about 8.0, from about 6.5 to about 8.0, from about 6.5 and about 8.0, or from about 7.0 and about 8.0.

In some embodiment, the ophthalmic composition described herein has a pH of 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 18 months, at least about 24 months, at least about 3 years, at least about 4 years, at least about 5 years, or more. In other embodiments, the formulations described herein are stable with respect to pH over a period of at least about 1 week. In other embodiments, the formulations described herein are stable with respect to pH over a period of at least about 2 weeks. In other embodiments, the formulations described herein are stable with respect to pH over a period of at least about 3 weeks. In other embodiments, the formulations described herein are stable with respect to pH over a period of at least about 1 month. Also described herein are formulations that are stable with respect to pH over a period of at least about 2 months, or more.

Osmolarity

In some embodiments, a composition disclosed herein is formulated in order to not disrupt the ionic balance of the eye. In some embodiments, a composition disclosed herein has an ionic balance that is the same as or substantially the same as the eye. In some embodiments, a composition disclosed herein does not does not disrupt the ionic balance of the eye.

As used herein, "practical osmolarity/osmolality" or "deliverable osmolarity/osmolality" means the osmolarity/osmolality of a composition as determined by measuring the osmolarity/osmolality of the ophthalmic agent and all excipients except the gelling and/or the thickening agent (e.g., polyoxyethylene-polyoxypropylene copolymers, carboxymethylcellulose or the like). The practical osmolarity of a composition disclosed herein is measured by a suitable method, e.g., a freezing point depression method as described in Viegas et. al., Int. J. Pharm., 1998, 160, 157-162. In some instances, the practical osmolarity of a composition disclosed herein is measured by vapor pressure osmometry (e.g., vapor pressure depression method) that allows for determination of the osmolarity of a composition at higher temperatures.

In some embodiments, the osmolarity at a target site of action (e.g., the eye) is about the same as the delivered osmolarity of a composition described herein. In some embodiments, a composition described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an ophthalmic composition disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, suitable tonicity adjusting agents include, but are not limited to any pharmaceutically acceptable sugar, salt or any combinations or mixtures thereof, such as, but not limited to dextrose, glycerin, mannitol, sorbitol, sodium chloride, and other electrolytes. In some instances, the tonicity adjusting agent is selected from sodium chloride, sodium nitrate, sodium sulfate, sodium bisulfate, potassium chloride, calcium chloride, magnesium chloride, zinc chloride, potassium acetate, sodium acetate, sodium bicarbonate, sodium carbonate, sodium thiosulfate, magnesium sulfate, disodium hydrogen phosphate, sodium dihydrogen phosphate, potassium dihydrogen phosphate, dextrose, mannitol, sorbitol, dextrose, sucrose, urea, propylene glycol, glycerin, or a combination thereof.

In some embodiment, the ophthalmic compositions described herein include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Sterility

In some embodiments, the compositions are sterilized. Included within the embodiments disclosed herein are means and processes for sterilization of a pharmaceutical composition disclosed herein for use in humans. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments, a process for the preparation of an ophthalmic formulation comprises subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 μm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C: Health Industry Manufacturers Association, 1981) and involve challenging the membrane filter with a known quantity (ca. $10^7/cm^2$) of unusually small microorganisms, such as *Brevundimonas diminuta* (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 μm filters without destroying their organized structure.

In some embodiments, the methods disclosed herein comprise sterilizing the formulation (or components thereof) by means of filtration sterilization. In ophthalmic gel compositions that includes thermosetting polymers, filtration is carried out below (e.g. about 5° C.) the gel temperature (Tgel) of a formulation described herein and with viscosity that allows for filtration in a reasonable time using a peristaltic pump (e.g. below a theoretical value of 100 cP).

Accordingly, provided herein are methods for sterilization of ophthalmic formulations that prevent degradation of polymeric components (e.g., thermosetting and/or other viscosity enhancing agents) and/or the ophthalmic agent during the process of sterilization. In some embodiments, degradation of the ophthalmic agent is reduced or eliminated through the use of specific pH ranges for buffer components and specific proportions of viscosity enhancing agents in the formulations. In some embodiments, the choice of an appropriate viscosity enhancing agents or thermosetting polymer allows for sterilization of formulations described herein by filtration. In some embodiments, the use of an appropriate thermosetting polymer or other viscosity enhancing agents in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the ophthalmic agent and/or excipients and/or viscosity enhancing agents during the sterilization step and are rendered substantially free of microbes and/or pyrogens.

Radiation Sterilization

One advantage of radiation sterilization is the ability to sterilize many types of products without heat degradation or other damage. The radiation commonly employed is beta radiation or alternatively, gamma radiation from a $^{60}Co$ source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free-radicals. Subsequent chemical reactions, such as rearrangements and cross-linking processes, result in the loss of normal function for these biological macromolecules. The formulations described herein are also optionally sterilized using beta irradiation.

Sterilization by Heat

Many methods are available for sterilization by the application of high heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Microorganisms

In some embodiments, the compositions are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less that 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

An important component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

In certain embodiments, the ophthalmic formulation described herein has less than about 60 colony forming units (CFU), less than about 50 colony forming units, less than about 40 colony forming units, or less than about 30 colony forming units of microbial agents per gram of formulation. In certain embodiments, the ophthalmic formulations described herein are formulated to be isotonic with the eye.

Endotoxins

An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The bioburden (e.g., microbial limit) and/or sterility (e.g., endotoxin level) is expressed in any units as recognized in the art. In certain embodiments, ophthalmic compositions described herein contain lower endotoxin levels (e.g. <4 EU/kg of body weight of a subject) when compared to conventionally acceptable endotoxin levels (e.g., 5 EU/kg of body weight of a subject). In some embodiments, the ophthalmic formulation has less than about 5 EU/kg of body weight of a subject. In other embodiments, the ophthalmic formulation has less than about 4 EU/kg of body weight of a subject. In additional embodiments, the ophthalmic formulation has less than about 3 EU/kg of body weight of a subject. In additional embodiments, the ophthalmic formulation has less than about 2 EU/kg of body weight of a subject.

In some embodiments, the ophthalmic formulation has less than about 5 EU/kg of formulation. In other embodiments, the ophthalmic formulation has less than about 4 EU/kg of formulation. In additional embodiments, the ophthalmic formulation has less than about 3 EU/kg of formulation. In some embodiments, the ophthalmic formulation has less than about 5 EU/kg Product. In other embodiments, the ophthalmic formulation has less than about 1 EU/kg Product. In additional embodiments, the ophthalmic formulation has less than about 0.2 EU/kg Product. In some embodiments, the ophthalmic formulation has less than about 5 EU/g of unit or Product. In other embodiments, the ophthalmic formulation has less than about 4 EU/g of unit or Product. In additional embodiments, the ophthalmic formulation has less than about 3 EU/g of unit or Product. In some embodiments, the ophthalmic formulation has less than about 5 EU/mg of unit or Product. In other embodiments, the ophthalmic formulation has less than about 4 EU/mg of unit or Product. In additional embodiments, the ophthalmic formulation has less than about 3 EU/mg of unit or Product. In certain embodiments, ophthalmic formulations described herein contain from about 1 to about 5 EU/mL of formulation. In certain embodiments, ophthalmic formulations described herein contain from about 2 to about 5 EU/mL of formulation, from about 3 to about 5 EU/mL of formulation, or from about 4 to about 5 EU/mL of formulation.

In certain embodiments, ophthalmic compositions described herein contain lower endotoxin levels (e.g. <0.5 EU/mL of formulation) when compared to conventionally acceptable endotoxin levels (e.g., 0.5 EU/mL of formulation). In some embodiments, the ophthalmic formulation has less than about 0.5 EU/mL of formulation. In other embodiments, the ophthalmic formulation has less than about 0.4 EU/mL of formulation. In additional embodiments, the ophthalmic formulation has less than about 0.2 EU/mL of formulation.

Pyrogen detection, by way of example only, is performed by several methods. Suitable tests for sterility include tests described in United States Pharmacopoeia (USP)<71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, MD, 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the ophthalmic formulation is subject to depyrogenation. In a further embodiment, the process for the manufacture of the ophthalmic formulation comprises testing the formulation for pyrogenicity. In certain embodiments, the formulations described herein are substantially free of pyrogens.

Ophthalmic Gel Composition

Gels have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a non-limiting example of a hydrophobic gel includes a liquid paraffin with polyethylene or fatty oils gelled with colloidal silica, or aluminum or zinc soaps. In contrast, the base of a non-limiting example of a hydrophilic gel includes water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions disclosed herein is pseudo plastic, plastic, thixotropic, or dilatant.

In some embodiments, the ophthalmic composition is an ophthalmic gel, and wherein the ophthalmically acceptable carrier comprises water and at least one viscosity-enhancing agent. In some embodiments, the viscosity-enhancing agent is selected from cellulose-based polymers, polyoxyethylene-polyoxypropylene triblock copolymers, dextran-based polymers, polyvinyl alcohol, dextrin, polyvinylpyrrolidone, polyalkylene glycols, chitosan, collagen, gelatin, hyaluronic acid, or combinations thereof.

In some embodiment, the ophthalmic gel composition described herein is a semi-solid or id in a gelled state before it is topically administered (e.g. at room temperature). For example, suitable viscosity-enhancing agents for such gels include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the ophthalmically acceptable viscosity agent includes hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted ocular site include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the ophthalmic agents disclosed herein acts as a controlled release formulation, restricting the diffusion of the ophthalmic agents from the formulation. Moreover, the combination of carboxymethylated chitosan and alginate is optionally used to assist in increasing the permeability of the ophthalmic agents in the eye.

In some embodiments is an enhanced viscosity formulation, comprising from about 0.1 mM and about 100 mM of an ophthalmic agent, a pharmaceutically acceptable viscosity agent, and water for injection, the concentration of the viscosity agent in the water being sufficient to provide a enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the ophthalmic agent. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of the ophthalmic agent.

In one embodiment, the pharmaceutically acceptable enhanced viscosity ophthalmically acceptable formulation comprises at least one ophthalmic agent and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, the ophthalmic gel composition described herein is an in situ gel formulation. In some instances, the in situ gel formation is based on increased pre-corneal residence time of the ophthalmic composition which improves ocular bioavailability, corneal mucoadhesion, lysosomal interaction and ionic gelation, improved corneal absorption, thermal gelation, or a combination thereof. In some instances, the in situ gel formulation is activated by pH, temperature, ion, UV, or solvent exchange.

In some instances, the ophthalmic gel composition comprises one or more gelling agents. In some instances, the gelling agent includes, but is not limited to, poloxamer (e.g.

Poloxamer 407), tetronics, ethyl (hydroxyethyl) cellulose, cellulose acetate phthalate (CAP), carbopol (e.g. Carbopol 1342P NF, Carbopol 980 NF), alginates (e.g. low acetyl gellan gum (Gelrite®)), gellan, hyaluronic acid, pluronics (e.g. Pluronic F-127), chitosan, polyvinyl alcohol (PVA), polyvinylpyrrolidone (PVP), dextran, hydroxy propyl methyl cellulose (HPMC), hydroxyethylcellulose (HEC), methylcellulose (MC), thiolated xyloglucan, polymethacrilic acid (PMMA), polyethylene glycol (PEG), pseudolatexes, xyloglucans, or combinations thereof.

In some instances, the in situ gel formation further comprises a permeation enhancer. In some instances, the permeation enhancer includes surfactants (e.g. non-ionic surfactants), benzalkonium chloride, EDTA, surface-active heteroglycosides, calcium chelators, hydroxyl propyl beta cyclodextrin (HP beta CD), bile salts, and the like.

In some embodiments, other gel formulations are useful depending upon the particular ophthalmic agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the ophthalmic agent formulations described herein. In some embodiments, ophthalmically acceptable gels include, but are not limited to, alginate hydrogels SAF®-Gel (ConvaTec, Princeton, N.J.), Duoderm® Hydroactive Gel (ConvaTec), Nu-gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in ophthalmically acceptable formulations disclosed and described herein.

In some embodiments, the viscosity-enhancing agent is a cellulose-based polymer selected from cellulose gum, alkylcellulose, hydroxyl-alkyl cellulose, hydroxyl-alkyl alkylcellulose, carboxy-alkyl cellulose, or combinations thereof. In some embodiments, the viscosity-enhancing agent is hydroxyl-alkyl alkylcellulose. In some embodiment, the viscosity-enhancing agent is hydroxypropyl methylcellulose.

In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. Included within the definition of body temperature is the body temperature of a healthy individual, or an unhealthy individual, including an individual with a fever (up to ~42° C.). In some embodiments, the pharmaceutical compositions described herein are liquids at about room temperature and are administered at or about room temperature.

Copolymers polyoxypropylene and polyoxyethylene (e.g. polyoxyethylene-polyoxypropylene triblock copolymers) form thermosetting gels when incorporated into aqueous solutions. These polymers have the ability to change from the liquid state to the gel state at temperatures close to body temperature, therefore allowing useful formulations that are applied to the targeted ocular site. The liquid state-to-gel state phase transition is dependent on the polymer concentration and the ingredients in the solution.

In some embodiments, the amount of thermosetting polymer in any formulation described herein is about 10%, about 15%, about 20%, about 25%, about 30%, about 35% or about 40% of the total weight of the formulation. In some embodiments, the amount of thermosetting polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermosetting polymer (e.g., Poloxamer 407) in any formulation described herein is about 7.5% of the total weight of the formulation. In some embodiments, the amount of thermosetting polymer (e.g., Poloxamer 407) in any formulation described herein is about 10% of the total weight of the formulation. In some embodiments, the amount of thermosetting polymer (e.g., Poloxamer 407) in any formulation described herein is about 11% of the total weight of the formulation. In some embodiments, the amount of thermosetting polymer (e.g., Poloxamer 407) in any formulation described herein is about 12% of the total weight of the formulation. In some embodiments, the amount of thermosetting polymer (e.g., Poloxamer 407) in any formulation described herein is about 13% of the total weight of the formulation. In some embodiments, the amount of thermosetting polymer (e.g., Poloxamer 407) in any formulation described herein is about 14% of the total weight of the formulation. In some embodiments, the amount of thermosetting polymer (e.g., Poloxamer 407) in any formulation described herein is about 15% of the total weight of the formulation. In some embodiments, the amount of thermosetting polymer (e.g., Poloxamer 407) in any formulation described herein is about 16% of the total weight of the formulation. In some embodiments, the amount of thermosetting polymer (e.g., Poloxamer 407) in any formulation described herein is about 17% of the total weight of the formulation. In some embodiments, the amount of thermosetting polymer (e.g., Poloxamer 407) in any formulation described herein is about 18% of the total weight of the formulation. In some embodiments, the amount of thermosetting polymer (e.g., Poloxamer 407) in any formulation described herein is about 19% of the total weight of the formulation. In some embodiments, the amount of thermosetting polymer (e.g., Poloxamer 407) in any formulation described herein is about 20% of the total weight of the formulation. In some embodiments, the amount of thermosetting polymer (e.g., Poloxamer 407) in any formulation described herein is about 21% of the total weight of the formulation. In some embodiments, the amount of thermosetting polymer (e.g., Poloxamer 407) in any formulation described herein is about 23% of the total weight of the formulation. In some embodiments, the amount of thermosetting polymer (e.g., Poloxamer 407) in any formulation described herein is about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting coploymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PLGA copolymer of 50:50 poly(DL-lactide-co-glycolide) and is 10% w/w of PEG and has a molecular weight of about 6000.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly(DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermosetting gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermosetting gel polymer. The ophthalmic agent and various additives such as buffers, salts, and preservatives are subsequently added and dissolved. In some instances the pharmaceutically agent is suspended if it is insoluble in water. The pH is modulated by the addition of appropriate buffering agents.

Ophthalmic Ointment Composition

An ointment is a homogeneous, viscous, semi-solid preparation, most commonly a greasy, thick oil (e.g. oil 80%-water 20%) with a high viscosity, intended for external application to the skin or mucous membranes. Ointments have a Water number that defines the maximum amount of water that it can contain. They are used as emollients or for the application of active ingredients to the skin for protective, therapeutic, or prophylactic purposes and where a degree of occlusion is desired. Ointments are used topically on a variety of body surfaces. These include the skin and the mucous membranes of the eye (an eye ointment), vulva, anus, and nose The vehicle of an ointment is known as the ointment base. The choice of a base depends upon the clinical indication for the ointment. The different types of ointment bases are: hydrocarbon bases, e.g. hard paraffin, soft paraffin, microcrystalline wax and ceresine; absorption bases, e.g. wool fat, beeswax; water soluble bases, e.g. macrogols 200, 300, 400; emulsifying bases, e.g. emulsifying wax, cetrimide; vegetable oils, e.g. olive oil, coconut oil, sesame oil, almond oil and peanut oil.

Ointments are formulated using hydrophobic, hydrophilic, or water-emulsifying bases to provide preparations that are immiscible, miscible, or emulsifiable with skin secretions. They can also be derived from hydrocarbon (fatty), absorption, water-removable, or water-soluble bases. The active agents are dispersed in the base, and later they get divided after the drug penetration into the target sites (e.g. membranes, skins, etc.).

The present disclosure recognizes that it is sometimes difficult to incorporate into the ointment a drug of low concentration with sufficient dose-to-dose uniformity for effectively treating a disorder or disease. In some embodiments, poly(ethylene-glycols), polyethoxylated castor oils (Cremophor®EL), alcohols having 12 to 20 carbon atoms or a mixture of two or more of said components are effective excipients for dispersing and/or dissolving effective amounts of ophthalmic drugs, in particular of ascomycins and staurosporine derivatives, in an ointment base, in particular in an ointment base substantially comprising oleaginous and hydrocarbon components, and that the resulting ointments are excellently tolerated by the skin and by ocular tissue.

The present disclosure further recognizes that ophthalmic drugs, such as a compound of Formula (I), or an isotopic variant, tautomer, pharmaceutically acceptable salt, solvate, or hydrate thereof, incorporated in the ointment compositions describes herein can effectively target the choroid and/or retina in a patient when the compositions are topically administered to the ocular surface, in particular to the sclera of said patient. In some embodiments, an ophthalmic ointment composition includes an ophthalmic drug, an ointment base and an agent for dispersing and/or dissolving said drug in the ointment base, selected from a poly(ethylene-glycol), a polyethoxylated castor oil, an alcohol having 12 to 20 carbon atoms and a mixture of two or more of said components.

In some embodiments, the ointment bases include ophthalmically acceptable oil and fat bases, such as natural wax e.g. white and yellow bees wax, carnauba wax, wool wax (wool fat), purified lanolin, anhydrous lanolin; petroleum wax e.g. hard paraffin, microcrystalline wax; hydrocarbons e.g. liquid paraffin, white and yellow soft paraffin, white petrolatum, yellow petrolatum; or combinations thereof.

The above mentioned oil and fat bases are described in more detail, for instance, in the British Pharmacopoeia, Edition 2001, or the European Pharmacopoeia, 3rd Edition.

The ointment base may be present in amounts of about 50 to about 95, preferably of 70 to 90% by weight based on the total weight of the composition.

A preferred ointment base comprises a combination of one or more of one or more natural waxes like those indicated above, preferably wool wax (wool fat), and one or more hydrocarbons like those indicated above, preferably a soft paraffin or a petrolatum, more preferably in combination with liquid paraffin.

A special embodiment of the aforementioned ointment base comprises e.g. 5 to 17 parts by weight of wool fat, and 50 to 65 parts by weight of white petrolatum as well as 20 to 30 parts by weight of liquid paraffin.

The agent for dispersing and/or dissolving the ophthalmic drug in the ointment base may be selected from a poly (ethylene-glycol), a polyethoxylated castor oil, an alcohol having 12 to 20 carbon atoms and a mixture of two or more of said components. The agent is preferably used in amounts of 1 to 20 percent, more preferably 1 to 10 percent by weight of the entire semisolid ophthalmic composition.

Alcohols having 12 to 20 carbon atoms include particularly stearyl alcohol (C18H37OH), cetyl alcohol ($C_{16}H_{33}OH$) and mixtures thereof. Preferred are so-called cetostearyl alcohols, mixtures of solid alcohols substantially consisting of stearyl and cetyl alcohol and preferably comprising not less than 40 percent by weight of stearyl alcohol and a sum of stearyl alcohol and cetyl alcohol amounting to at least 90 percent by weight, and compositions comprising not less than 80 percent by weight of cetylstearyl alcohol and an emulsifier, in particular sodium cetostearyl sulfate and/or sodium lauryl sulfate, preferably in amounts not less than 7 percent by weight of emulsifier.

Polyethoxylated castor oils are reaction products of natural or hydrogenated castor oils and ethylene glycol. Such products may be obtained in known manner, e.g. by reaction of a natural or hydrogenated castor oil or fractions thereof with ethylene oxide, e.g. in a molar ratio of from about 1:30 to about 1:60, with optional removal of free polyethylene glycol components from the product, e.g. in accordance with the methods disclosed in German Auslegeschriften 1,182, 388 and 1,518,819. Especially suitable and preferred is a product commercially available under the trade name Cremophor®EL having a molecular weight (by steam osmometry)=ca. 1630, a saponification no.=ca. 65-70, an acid no.=ca. 2, an iodine no.=ca. 28-32 and an nD 25=ca.1.471. Also suitable for use in this category is, for instance, Nikkol®HCO-60, a reaction product of hydrogenated castor oil and ethylene oxide exhibiting the following characteristics: acid no.=ca. 0.3; saponification no.=ca. 47.4; hydroxy value=ca. 42.5. pH (5%)=ca. 4.6; Color APHA=ca. 40; m.p.=ca. 36.0° C.; Freezing point=ca. 32.4° C.; H2O content (%, KF)=ca. 0.03.

Poly(ethylene-glycols) are used in some embodiments as the agent for dispersing and/or dissolving the ophthalmic drug in the ointment base according to the present disclosure. Suitable poly(ethylene-glycol)s are typically mixtures of polymeric compounds of the general formula H—(OCH2-CH2)nOH, wherein the index n may typically range from 4 to 230 and the mean molecular weight from about 200 to about 10000. Preferably n is a number from about 6 to about 22 and the mean molecular weight between about 300 and about 1000, more preferably n ranges from about 6 to about 13 and the mean molecular weight from about 300 to about 600, most preferably n has a value of about 8.5 to about 9 and the relative molecular weight is about 400. Suitable poly(ethylene-glycols) are readily available commercially, for example poly(ethylene-glycols) having a mean molecular weight of about 200, 300, 400, 600, 1000, 1500, 2000, 3000, 4000, 6000, 8000 and 10000.

The poly(ethylene-glycols), in particular the preferred types described in the foregoing paragraph, are preferably used in amounts of 1 to 10, more preferably 1 to 5 percent by weight of the entire semisolid ophthalmic composition.

An especially preferred embodiment of the compositions according to the instant disclosure comprises an agent for dispersing and/or dissolving of the drug in the ointment base which is selected from a poly(ethylene-glycol), a polyethoxylated castor oil and preferably a mixture of said components.

Gel/Ointment Viscosity

In some embodiments, the composition has a Brookfield RVDV viscosity of from about 10,000 to about 300,000 cps at about 20° C. and sheer rate of 1 $s^{-1}$. In some embodiments, the composition has a Brookfield RVDV viscosity of from about 15,000 to about 200,000 cps at about 20° C. and sheer rate of 1 $s^{-1}$. In some embodiments, the composition has a Brookfield RVDV viscosity of from about 50,000 to about 150,000 cps at about 20° C. and sheer rate of 1 $s^{-1}$. In some embodiments, the composition has a Brookfield RVDV viscosity of from about 70,000 to about 130,000 cps at about 20° C. and sheer rate of 1 $s^{-1}$. In some embodiments, the composition has a Brookfield RVDV viscosity of from about 90,000 to about 110,000 cps at about 20° C. and sheer rate of 1 $s^{-1}$.

In some embodiments, the ophthalmic gel formulation contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the ophthalmic gel formulation contains a viscosity enhancing agent sufficient to provide a viscosity of between about 50,0000 and 1,000,000 centipoise.

In some embodiments, the compositions described herein are low viscosity compositions at body temperature. In some embodiments, low viscosity compositions contain from about 1% to about 10% of a viscosity enhancing agent (e.g., gelling components such as polyoxyethylene-polyoxypropylene copolymers). In some embodiments, low viscosity compositions contain from about 2% to about 10% of a viscosity enhancing agent (e.g., gelling components such as polyoxyethylene-polyoxypropylene copolymers). In some embodiments, low viscosity compositions contain from about 5% to about 10% of a viscosity enhancing agent (e.g., gelling components such as polyoxyethylene-polyoxypropylene copolymers). In some embodiments, low viscosity compositions are substantially free of a viscosity enhancing agent (e.g., gelling components such as polyoxyethylene-polyoxypropylene copolymers). In some embodiments, a low viscosity ophthalmic agent composition described herein provides an apparent viscosity of from about 100 cP to about 10,000 cP. In some embodiments, a low viscosity ophthalmic agent composition described herein provides an apparent viscosity of from about 500 cP to about 10,000 cP. In some embodiments, a low viscosity ophthalmic agent composition described herein provides an apparent viscosity of from about 1000 cP to about 10,000 cP.

In some embodiments, the compositions described herein are viscous compositions at body temperature. In some embodiments, viscous compositions contain from about 10% to about 25% of a viscosity enhancing agent (e.g., gelling components such as polyoxyethylene-polyoxypropylene copolymers). In some embodiments, the viscous compositions contain from about 14% to about 22% of a viscosity enhancing agent (e.g., gelling components such as polyoxyethylene-polyoxypropylene copolymers). In some embodiments, the viscous compositions contain from about 15% to about 21% of a viscosity enhancing agent (e.g., gelling components such as polyoxyethylene-polyoxypropylene copolymers). In some embodiments, a viscous ophthalmic composition described herein provides an apparent viscosity of from about 100,000 cP to about 1,000,000 cP. In some embodiments, a viscous ophthalmic composition described herein provides an apparent viscosity of from about 150,000 cP to about 500,000 cP. In some embodiments, a viscous ophthalmic composition described herein provides an apparent viscosity of from about 250,000 cP to about 500,000 cP. In some of such embodiments, a viscous ophthalmic composition is a liquid at room temperature and gels at about between room temperature and body temperature (including an individual with a serious fever, e.g., up to about 42° C.). In some embodiments, a viscous ophthalmic composition is administered as monotherapy for treatment of an ophthalmic disease or condition described herein.

In some embodiments, the viscosity of the gel formulations presented herein is measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

Gel/Ointment Dose-To-Dose Uniformity

Typical ophthalmic gels are packaged in eye drop bottles and administered as drops. For example, a single administration (i.e. a single dose) of an ophthalmic gel may include a single drop, two drops, three drops or more into the eyes of the patient. Furthermore, typical ophthalmic ointments are packaged in tubes or other squeezable containers with a dispensing nozzle through which strips of the ointment are delivered. For example, a single administration (i.e. a single dose) of an ophthalmic ointment may include a single strip, or multiple strips into the eyes of the patient. In some embodiments, one dose of the ophthalmic gel described herein is one drop of the gel composition from the eye drop bottle. In some embodiments, one dose of the ophthalmic ointment is one strip of the ointment composition dispensed through the nozzle of a dispersing tube.

In some cases, described herein include ophthalmic gel compositions which provide a dose-to-dose uniform concentrations. In some instances, the dose-to-dose uniform concentration does not present significant variations of drug content from one dose to another. In some instances, the dose-to-dose uniform concentration does provide consistant drug content from one dose to another.

In some cases, described herein include ophthalmic ointment compositions which provide a dose-to-dose uniform concentrations. In some instances, the dose-to-dose uniform concentration does not present significant variations of drug content from one dose to another. In some instances, the dose-to-dose uniform concentration does provide consistant drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

A nonsettling formulation should not require shaking to disperse drug uniformly. A "no-shake" formulation is potentially advantageous over formulations that require shaking for the simple reason that patients' shaking behavior is a major source of variability in the amount of drug dosed. It has been reported that patients often times do not or forget to shake their ophthalmic compositions that requires shaking before administering a dose, despite the instructions to shake that were clearly marked on the label. On the other hand, even for those patients who do shake the product, it is normally not possible to determine whether the shaking is adequate in intensity and/or duration to render the product uniform. In some embodiments, the ophthalmic gel compositions and ophthalmic ointment compositions described herein are "no-shake" formulations that maintained the dose-to-dose uniformity described herein.

To evaluate the dose-to-dose uniformity, drop bottles or tubes containing the ophthalmic aqueous compositions, the ophthalmic gel compositions, or ophthalmic ointment compositions are stored upright for a minimum of 12 hours prior to the start of the test. To simulate the recommended dosing of these products, predetermined number of drops or strips are dispensed from each commercial bottles or tubes at predetermined time intervals for an extended period of time or until no product was left in the bottle or tube. All drops and strips are dispensed into tared glass vials, capped, and stored at room temperature until analysis.

In some embodiments, a milling process is used to reduce the size of a solid material to form particles in the micrometer to nanometer size range. Dry and wet milling processes such as jet milling, cryo-milling, ball milling, media milling, and homogenization are known and can be used in methods described herein. Generally, in a wet milling process, a suspension of the material to be used as the nanoparticle is mixed with milling media with or without excipients to reduce particle size. Dry milling is a process wherein the material to be used as the nanoparticle is mixed with milling media with or without excipients to reduce particle size. In a cryo-milling process, a suspension of the material to be used as the nanoparticle is mixed with milling media with or without excipients under cooled temperatures. Any suitable grinding medium can be used for milling. In some embodiments, a ceramic and/or polymeric material and/or a metal can be used. Examples of suitable materials may include zirconium oxide, silicon carbide, silicon oxide, silicon nitride, zirconium silicate, yttrium oxide, glass, alumina, alpha-alumina, aluminum oxide, polystyrene, poly(methyl methacrylate), titanium, steel. A grinding medium may have any suitable size. For example, the grinding medium may have an average diameter of at least about 0.1 mm, at least about 0.2 mm, at least about 0.5 mm, at least about 0.8 mm, at least about 1 mm, at least about 2 mm, or at least about 5 mm. In some cases, the grinding medium may have an average diameter of less than or equal to about 5 mm, less than or equal to about 2 mm, less than or equal to about 1 mm, less than or equal to about 0.8, less than or equal to about 0.5 mm, or less than or equal to about 0.2 mm. Combinations of the above-referenced ranges are also possible (e.g., an average diameter of at least about 0.5 millimeters and less than or equal to about 1 mm). Other ranges are also possible.

Any suitable solvent may be used for milling. The choice of solvent may depend on factors such as the solid material being milled, the particular type of stabilizer/mucus penetrating agent being used (e.g., one that may render the particle mucus penetrating), the grinding material be used, among other factors. Suitable solvents may be ones that do not substantially dissolve the solid material or the grinding material, but dissolve the stabilizer/mucus penetrating agent to a suitable degree. Non-limiting examples of solvents may include water, buffered solutions, other aqueous solutions, alcohols (e.g., ethanol, methanol, butanol), and mixtures thereof that may optionally include other components such as pharmaceutical excipients, polymers, pharmaceutical agents, salts, preservative agents, viscosity modifiers, tonicity modifier, taste masking agents, antioxidants, pH modifier, and other pharmaceutical excipients. In other embodiments, an organic solvent can be used. A pharmaceutical agent may have any suitable solubility in these or other solvents, such as solubility in one or more of the ranges described above for aqueous solubility or for solubility in a coating solution.

By way of example only, the ophthalmically acceptable viscosity agent includes hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted ocular site include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the ophthalmic agents disclosed herein acts as a controlled release formulation, restricting the diffusion of the ophthalmic agents from the formulation. Moreover, the combination of carboxymethylated chitosan and alginate is optionally used to assist in increasing the permeability of the ophthalmic agents in the eye.

In some embodiments is an enhanced viscosity formulation, comprising from about 0.1 mM and about 100 mM of an ophthalmic agent, a pharmaceutically acceptable viscosity agent, and water for injection, the concentration of the viscosity agent in the water being sufficient to provide a enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the ophthalmic agent. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of the ophthalmic agent.

In one embodiment, the pharmaceutically acceptable enhanced viscosity ophthalmically acceptable formulation comprises at least one ophthalmic agent and at least one gelling agent. Suitable gelling agents for use in preparation of the formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent.

In some instances, the ophthalmic composition comprises one or more gelling agents. In some instances, the gelling agent includes, but is not limited to, poloxamer (e.g. Poloxamer 407), tetronics, ethyl (hydroxyethyl) cellulose, cellulose acetate phthalate (CAP), carbopol (e.g. Carbopol 1342P NF, Carbopol 980 NF), alginates (e.g. low acetyl gellan gum (Gelrite®)), gellan, hyaluronic acid, pluronics (e.g. Pluronic F-127), chitosan, polyvinyl alcohol (PVA), polyvinylpyrrolidone (PVP), dextran, hydroxy propyl methyl cellulose (HPMC), hydroxyethylcellulose (HEC), methylcellulose (MC), thiolated xyloglucan, polymethacrilic acid (PMMA), polyethylene glycol (PEG), pseudolatexes, xyloglucans, or combinations thereof.

In some embodiments, the viscosity-enhancing agent is a cellulose-based polymer selected from cellulose gum, alkylcellulose, hydroxyl-alkyl cellulose, hydroxyl-alkyl alkylcellulose, carboxy-alkyl cellulose, or combinations thereof. In some embodiments, the viscosity-enhancing agent is hydroxyl-alkyl alkylcellulose. In some embodiment, the viscosity-enhancing agent is hydroxypropyl methylcellulose.

Dose-To-Dose Uniformity

Typical ophthalmic formulations are packaged in eye drop bottles and administered as drops. For example, a single administration (i.e., a single dose) of an ophthalmic formulation may include a single drop, two drops, three drops or more into the eyes of the patient. In some embodiments, one dose of the ophthalmic formulation described herein is three drop sszof the composition from the eye drop bottle.

In some cases, described herein are ophthalmic compositions which provide a dose-to-dose uniform concentrations. In some instances, the dose-to-dose uniform concentration does not present significant variations of drug content from one dose to another. In some instances, the dose-to-dose uniform concentration does provide consistant drug content from one dose to another.

In some cases, described herein include ophthalmic ointment compositions which provide a dose-to-dose uniform concentrations. In some instances, the dose-to-dose uniform concentration does not present significant variations of drug content from one dose to another. In some instances, the dose-to-dose uniform concentration does provide consistant drug content from one dose to another.

In some embodiments, the composition has a dose-to-dose ophthalmic agent concentration variation of less than 50%. In some embodiments, the composition has a dose-to-dose ophthalmic agent concentration variation of less than 40%. In some embodiments, the composition has a dose-to-dose ophthalmic agent concentration variation of less than 30%. In some embodiments, the composition has a dose-to-dose ophthalmic agent concentration variation of less than 20%. In some embodiments, the composition has a dose-to-dose ophthalmic agent concentration variation of less than 10%. In some embodiments, the composition has a dose-to-dose ophthalmic agent concentration variation of less than 5%.

In some embodiments, the dose-to-dose ophthalmic agent concentration variation is based on 10 consecutive doses. In some embodiments, the dose-to-dose ophthalmic agent concentration variation is based on 8 consecutive doses. In some embodiments, the dose-to-dose ophthalmic agent concentration variation is based on 5 consecutive doses. In some embodiments, the dose-to-dose ophthalmic agent concentration variation is based on 3 consecutive doses. In some embodiments, the dose-to-dose ophthalmic agent concentration variation is based on 2 consecutive doses.

A nonsettling formulation should not require shaking to disperse drug uniformly. A "no-shake" formulation is potentially advantageous over formulations that require shaking for the simple reason that patients' shaking behavior is a major source of variability in the amount of drug dosed. It has been reported that patients often times do not or forget to shake their ophthalmic compositions that requires shaking before administering a dose, despite the instructions to shake that were clearly marked on the label. On the other hand, even for those patients who do shake the product, it is normally not possible to determine whether the shaking is adequate in intensity and/or duration to render the product uniform. In some embodiments, the ophthalmic compositions described herein are "no-shake" formulations that maintained the dose-to-dose uniformity described herein. To evaluate the dose-to-dose uniformity, drop bottles or tubes containing the ophthalmic compositions are stored upright for a minimum of 12 hours prior to the start of the test. To simulate the recommended dosing of these products, predetermined number of drops or strips are dispensed from each commercial bottles or tubes at predetermined time intervals for an extended period of time or until no product was left in the bottle or tube. All drops and strips are dispensed into tared glass vials, capped, and stored at room temperature until analysis.

II. METHODS OF USE

In an aspect, provided herein is a method of treating or preventing a disorder or disease, comprising administering to a subject in need thereof a therapeutically effective amount of a pharmaceutical composition comprising:

(i) a compound of Formula (I):

(I)

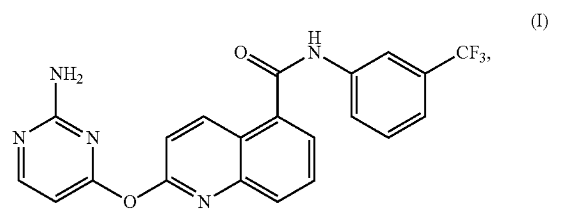 [SMILES: Nc1nccc(Oc2ccc3c(C(=O)Nc4cccc(C(F)(F)F)c4)cccc3n2)n1]

or an isotopic variant, tautomer, pharmaceutically acceptable salt, solvate, or hydrate thereof; and (ii) at least one pharmaceutically acceptable excipient, wherein the pharmaceutical composition is in a dosage form for ophthalmic dosing or administration;

and wherein the disorder or disease is a neovascular disorder or disease, inflammatory disorder or disease, or a cancer.

In an aspect, provided herein is a method of treating or preventing a disorder or disease, comprising administering to a subject in need thereof a therapeutically effective amount of a pharmaceutical composition comprising:

(i) fine particles of a compound of Formula (I):

(I)

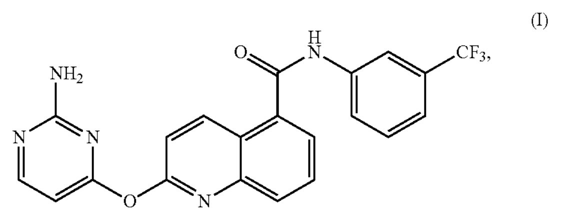 [SMILES: Nc1nccc(Oc2ccc3c(C(=O)Nc4cccc(C(F)(F)F)c4)cccc3n2)n1]

or an isotopic variant, tautomer, pharmaceutically acceptable salt, solvate, or hydrate thereof; and (ii) at least one pharmaceutically acceptable excipient, wherein the pharmaceutical composition is formulated as a suspension;

and wherein the disorder or disease is a neovascular disorder or disease, inflammatory disorder or disease, or a cancer.

In an aspect, provided herein is a method of treating or preventing an ophthalmic disorder or disease, comprising administering to a subject in need thereof a therapeutically effective amount of a pharmaceutical composition comprising:

(i) fine particles of a compound of Formula (I):

(I)

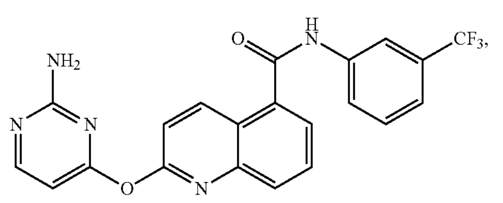

or an isotopic variant, tautomer, pharmaceutically acceptable salt, solvate, or hydrate thereof, and (ii) at least one pharmaceutically acceptable excipient, wherein the pharmaceutical composition is formulated as a suspension.

In an aspect, provided herein is a method of treating or preventing an ophthalmic disorder or disease, comprising administering to a subject in need thereof a therapeutically effective amount of a pharmaceutical composition comprising:

(i) a compound of Formula (I):

(I)

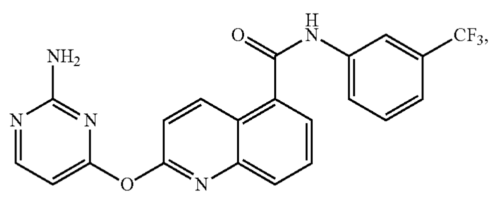

or an isotopic variant, tautomer, pharmaceutically acceptable salt, solvate, or hydrate thereof, and (ii) at least one pharmaceutically acceptable excipient, wherein the pharmaceutical composition is in a dosage form for ophthalmic dosing or administration.

In some embodiments, the ophthalmic disorder or disease affects function, clarity, and/or structure of the lens of the eye. In some embodiments, the ophthalmic disorder or disease is wet macular degeneration, cataracts, presbyopia, nuclear sclerosis of the eye lens, Refsum disease, Smith-Lemli-Opitz syndrome (SLOS), Schnyder crystalline corneal dystrophy (SCCD), abetalipoproteinemia, familial hypobetalipoproteinemia, neovascularization, or cancer. In some embodiments, the neovascularization is corneal neovascularization, iris neovascularization, or choroidal neovascularization. In some embodiments, the ophthalmic disorder or disease is corneal neovascularization. In some embodiments, the subject has undergone a surgical procedure for treatment of the ophthalmic disorder or disease.

In some embodiments, about 0.005 mg/mL to about 5.0 mg/mL of a pharmaceutical composition comprising the compound of Formula (I), or an isotopic variant, tautomer, pharmaceutically acceptable salt, solvate, or hydrate thereof is administered to the eye of the subject. In some embodiments, about 0.01 mg/mL to about 4.0 mg/mL of a pharmaceutical composition comprising the compound of Formula (I), or an isotopic variant, tautomer, pharmaceutically acceptable salt, solvate, or hydrate thereof is administered to the eye of the subject.

In some embodiments, the composition is administered the subject once per day, twice per day, three times per day, or four times per day.

In some embodiments, the composition is administered the subject three times per day. In some embodiments, about 60 μL of a pharmaceutical composition comprising the compound of Formula (I), or an isotopic variant, tautomer, pharmaceutically acceptable salt, solvate, or hydrate thereof is administered to the eye of the subject.

In some embodiments, the composition is administered the subject three times per day. In some embodiments, the composition is administered the subject four times per day.

In some embodiments, the administration is topical or by ophthalmic injection. In some embodiments, the ophthalmic injection is an intravitreous or subconjunctival injection.

In some embodiments of the methods provided herein, the pharmaceutical composition is administered to the subject daily. In some embodiments of the methods provided herein, the pharmaceutical composition is administered to the subject once per day, twice per day, three times per day, or four times per day. In some embodiments of the methods provided herein, the pharmaceutical composition is administered to the subject once per day. In some embodiments of the methods provided herein, the pharmaceutical composition is administered to the subject three times per day.

In some embodiments of the methods provided herein, the pharmaceutical composition is administered to the subject for a period of up to about 12 weeks. In some embodiments of the methods provided herein, the pharmaceutical composition is administered to the subject for a period of at least one week. In some embodiments of the methods provided herein, the pharmaceutical composition is administered to the subject for a period of at least two weeks. In some embodiments of the methods provided herein, the pharmaceutical composition is administered to the subject for a period of up to about 2 weeks. In some embodiments of the methods provided herein, the pharmaceutical composition is administered to the subject for a period of one week, two weeks, 6 weeks, 12 weeks, 24 weeks, 48 weeks, or 52 weeks.

In some embodiments, the ophthalmic aqueous formulations described herein are packaged in eye drop bottles and administered as drops. For example, a single administration (i.e. a single dose) of an ophthalmic aqueous formulation may include a single drop, two drops, three drops or more into the eyes of the patient. In some embodiments, the ophthalmic gel formulations described herein are packaged in eye drop bottles and administered as drops. For example, a single administration (i.e. a single dose) of an ophthalmic gel may include a single drop, two drops, three drops or more into the eyes of the patient. In some embodiments, the ophthalmic ointment formulations described herein are packaged in tubes or other squeezable containers with a dispensing nozzle through which strips of the ointment are delivered. For example, a single administration (i.e. a single dose) of an ophthalmic ointment may include a single strip, or multiple strips into the eyes of the patient. In some embodiments, one dose of the ophthalmic aqueous formulation described herein is one drop of the aqueous composition from the eye drop bottle. In some embodiments, one dose of the ophthalmic gel described herein is one drop of the gel composition from the eye drop bottle. In some embodiments, one dose of the ophthalmic ointment is one strip of the ointment composition dispensed through the nozzle of a dispersing tube.

In some embodiments, the ophthalmic aqueous formulations are administered as follows The lower lid of the eye to be administered was pulled down and a predetermined amount of the aqueous formulation (e.g. 1-3 drops) is applied to the inside of the eyelid. The ophthalmic tip of the dispensing mechanism does not touch any surface to avoid contamination and/or injury.

In some embodiments, the ophthalmic gel formulations are administered as follows The lower lid of the eye to be administered was pulled down and a predetermined amount of gel (e.g. 1-3 drops) is applied to the inside of the eyelid. The ophthalmic tip of the dispensing mechanism does not touch any surface to avoid contamination and/or injury.

In some embodiments, the ophthalmic ointment formulations are administered as follows The lower lid of the eye to be administered was pulled down and a small amount of ointment (approximately 0.25 inches) was applied to the inside of the eyelid. The ophthalmic tip of the dispensing mechanism does not touch any surface to avoid contamination and/or injury.

In some embodiments, the ophthalmic composition is administered at predetermined time intervals over an extended period of time. In some embodiments, the ophthalmic composition is administered three times every day (i.e., three or four doses). In some embodiments, the ophthalmic composition is administered over 1 week, 2 weeks, 1 month, 2 months, 3 months, 6 moths, 1 year, 2 years, 3 years, 4 years, 5 years, 6 years, 7 years, 8 years, 9 years, 10 years, 11 years, or 12-15 years.

In some embodiments, the ophthalmic composition is administered in doses having a dose-to-dose ophthalmic agent concentration variation of less than 50%, less than 40%, less than 30%, less than 20%, less than 10%, or less than 5%.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of an ophthalmic agent may be administered chronically, that is, for an extended period of time, including throughout the duration of the patient's life in order to ameliorate or otherwise control or limit the symptoms of the patient's disease or condition.

In the case wherein the patient's condition does not improve, upon the doctor's discretion the administration of the ophthalmic agent may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the ophthalmic agent may be given continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's ophthalmic conditions has occurred, a maintenance ophthalmic agent dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

The amount of ophthalmic agent that will correspond to such an amount will vary depending upon factors such as the particular compound, disease condition and its severity, according to the particular circumstances surrounding the case, including, e.g., the specific ophthalmic agent being administered, the route of administration, the condition being treated, the target area being treated, and the subject or host being treated. The desired dose is presented in a single dose or as divided doses administered simultaneously (or over a short period of time) or at appropriate intervals.

In some embodiments, the initial administration is a particular ophthalmic agent and the subsequent administration a different formulation or ophthalmic agent.

pH Adjusters

Sodium dihydrogen phosphate dihydrate ($NaH_2PO_4 \cdot 2H_2O$) and di-sodium hydrogen phosphate dodecahydrate ($Na_2HPO_4 \cdot 12H_2O$) are used as pH adjusters. Other alternatives include maleate, citrate etc. Wetting agents include cationic surfactant or anionic surfactant; and suspending agents include HPMC.

Suspensions

Defined as preparations containing finely divided drug particles (the suspensoid) distributed somewhat uniformly throughout a vehicle in which the drug exhibits a minimum degree of solubility. A suspension is the state of a drug when its particles are mixed with but undissolved in a fluid or solid.

Polyoxyl 15-Hydroxystearate (Kolliphor® HS 15)

Polyoxyl 15-Hydroxystearate is a new kind of excipient with high solubilization ability and low histamine release, low hemolytic activity and excellent physiological tolerance, which is approved for injection. Its safety is support by listed products and clinical research data.

HPMC

Hypromellose (HPMC E4M) is widely used as polymer suspending agent for suspension formulation. Other commercial grade products with different viscosities and different degrees of substitution may also be used.

Sodium Thiosulfate

Sodium thiosulfate as an antioxidant, the aqueous solution is neutral or slightly alkaline, precipitation when meeting acid, suitable for alkaline drugs.

Dosing

In some embodiments, the pharmaceutical compositions provided herein are administered administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

In some embodiments, the pharmaceutical compositions provided herein are administered administered daily, every other day, every other day 3 times a week, every 2 weeks, every 3 weeks, every 4 weeks, every 5 weeks, every 3 days, every 4 days, every 5 days, every 6 days, weekly, bi-weekly, 3 times a week, 4 times a week, 5 times a week, 6 times a week, once a month, twice a month, 3 times a month, once every 2 months, once every 3 months, once every 4 months, once every 5 months, or once every 6 months. In some instances, the method for the administration of multiple compounds (e.g., a compound of Formula (I), or an isotopic variant, tautomer, pharmaceutically acceptable salt, solvate, or hydrate thereof and another therapeutic agent) comprises administering compounds within 48 hours or less of each other. In some embodiments administration occurs within 24 hours, 16 hours, 12 hours, 11 hours, 10 hours, 9 hours, 8 hours, 7 hours, 6 hours, 5 hours, 4 hours, 3 hours, 2 hours, 1 hour, 30 minutes, 20 minutes, 15 minutes, or 10 minutes. In some instances, the compounds are administered simultaneously.

Angiogenesis and Neovascularization

Angiogenesis is a process of sprouting into a new vessel from an existing vessel. This process is associated with the migration and proliferation of vascular endothelial cell. Angiogenesis is relative to many serious human diseases, such as malignant tumor. So far, it was found that ocular angiogenesis diseases comprise age-related macular degeneration (AMD), diabetic retinopathy, neovascular glaucoma, and so on. The common characteristic of these diseases lies in the abnormal proliferation of ocular angiogenesis (Xiao Jin, et al., "Research Progress on the Clinical Application and Basic Mechanism of Anti-VEGF Drug," CHINA FOREIGN MEDICAL TREATMENT, 2012).

Angiogenesis and neovascularization are both regulated by a mixture of stimulators and inhibitors that are balanced to ensure the proper construction of blood vessels in the body. Mis-regulated angiogenesis or neovascularization is the underlying cause of numerous diseases and conditions. Inhibition of angiogenesis or neovascularization can be a useful therapy for diseases such as macular degeneration, diabetic nephropathy, rheumatoid arthritis, atherosclerotic plaques, endometriosis, Crohn's disease, uterine fibroids, benign prostatic hyperplasia, psoriasis, corneal neovascularization, iris neovascularization, choroidal neovascularization and cancer.

Multiple molecular mediators of angiogenesis have been identified including basic and acidic fibroblast growth factors (aFGF, bFGF), transforming growth factors alpha and beta (TGFα, TGFβ), platelet-derived growth factor (PDGF), angiogenin, platelet-derived endothelial cell growth factor (PD-ECGF), interleukin-8 (IL-8), and vascular endothelial growth factor (VEGF). Other stimulators implicated in angiogenesis include angiopoietin-1, Del-1, follistatin, granulocyte colony-stimulating factor (G-CSF), hepatocyte growth factor (HGF), leptin, midkine, placental growth factor, pleiotrophin (PTN), progranulin, proliferin, and tumor necrosis factor-alpha (TNF-alpha). In addition, control of angiogenesis is further mediated by a number of negative regulators of angiogenesis produced by the body including angioarrestin, ngiostatin (plasminogen fragment), antiangiogenic antithrombin III, cartilage-derived inhibitor (GDI), CD59 complement fragment, endostatin (collagen XVIII fragment), fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TE-VIPs), 2-methoxyestradiol, placental ribonuclease inhibitor, plasminogen activator inhibitor, platelet factor-4 (PF4), prolactin 16 kD fragment, proliferin-related protein (PRP), retinoids, tetrahydrocortisol-S, thrombospondin-1 (TSP-1), vasculostatin, and vasostatin (calreticulin fragment). Among these angiogenic regulators, VEGF appears to play a key role as a positive regulator of the abnormal angiogenesis accompanying tumor growth (reviewed in Brown et al, (1996) Control of Angiogenesis (Goldberg and Rosen, eds.) Birkhauser, Basel, and Thomas (1996) J. Biol. Chem. 271: 603-606). Furthermore, recently the role of the PDGF-B member of the PDGF family of signaling molecules has been under investigation, since it appears to play a role in the formation, expansion and proper function of perivascular cells, sometimes referred to as mural cells, e.g., vascular smooth muscle, mesangial cells, and pericytes.

Vascular endothelial growth factor receptor 2 (VEGFR2), also called kinase insert Domain receptor (KDR), family members are receptor tyrosine kinases, e.g., VEGFR1, VEGFR2 and so on. These receptors play an important role in the growth and metastasis of malignant tumors as well as in the development process of diseases such as vascular proliferative diseases (e.g., macular degeneration and tumor). EGFR2/KDR/Flk-1 (vascular endothelial growth factor receptor 2) is a transmembrane receptor tyrosine kinase that mediates the angiogenic effects of VEGF-A and VEGF-C. It is expressed primarily on vascular endothelial cells and endothelial cell progenitors. It is also expressed on endometrial epithelium, hematopoietic stem cells, liver sinusoidal endothelial cells, Sertoli cells and Leydig cells, platelets and megakaryocytes, sensory and autonomic neurons, Schwann cells, Muller glial cells, retinal progenitors, and osteoblasts. VEGFR2 can associate with VEGFR1, and a soluble form of VEGFR2 can circulate in the serum.

Platelet-derived growth factor receptors (PDGF-R) family members are receptor tyrosine kinases, e.g., PDGFRα and PDGFRβ, and colony-stimulating factor-1 receptor, stem cell growth factor receptor KIT, and so on. It was found that these kinases are closely associated with the occurrence and development of tumors. The abnormal expression of PDGFR has been found in melanoma, meningeoma, neuroendocrine neoplasm, ovarian cancer, prostate cancer, lung cancer and pancreatic cancer. The abnormal activation of KIT is a direct inducement of the occurrence and development of many tumors.

FGFR (Fibroblast Growth Factor Receptor) family members comprise FGFR1, FGFR2 and so on, which are closely associated with cancers. For example, the abnormal activation of FGFR2 has been found in endometrial cancer, cervical cancer, breast cancer, lung cancer and stomach cancer. SRC kinase family comprises proteins having tyrosine protein kinase activity. SRC kinase family, as an oncegene protein, is initially found in Rous Sarcoma Virus. It has been found that the inhibition of SRC has some treatment and improvement effect on cancers or other diseases. p38 Mitogen-Activated Protein Kinase (MAPK) Pathway is intracellular stress response signal pathway, which is closely associated with inflammatory response.

Macular degeneration is mainly divided into two types, dry and wet, wherein wet macular degeneration (AMD) is characterized by new vessel of choroid entering the retina and the subsequent pathological changes such as bleeding, exudation and edema. Wet macular degeneration will cause a rapid loss of vision, which is more serious than dry macular degeneration. Currently, there is a good progress in the treatment of wet macular degeneration. The early laser-cauterizing hemostasis is replaced by VEGF antagonists, however, the latter is replaced by photodynamic therapy soon due to the poor effect. Although photodynamic therapy has an improved efficacy, it is still unsatisfactory. Recently, a new VEGF antagonist-Lucentis, which is a recombinant of human-derived VEGF subtype monoclonal antibody fragment, is developed and it could reduce angiogenesis. This medicament is approved by U.S. FDA for treating wet macular degeneration in 2006, which has a good efficacy; and meanwhile, it was found that this anti-VEGF drug also has therapeutic effect on diabetic retinopathy and neovascular glaucoma. However, since Lucentis is an antibody drug with an extremely high price, it cannot popularize all over the world. Therefore, it is an intense competition focus in the current international pharmaceutical industry to develop small molecular angiogenesis inhibitor medicament having excellent efficacy and low price.

Kits/Articles of Manufacture

The disclosure also provides kits for treating a disease or disorder associated with the abnormal proliferation of angiogenesis. Such kits generally will comprise one or more of the ophthalmic compositions disclosed herein, and instructions for using the kit. The disclosure also contemplates the use of one or more of the ophthalmic compositions, in the manufacture of medicaments for treating, abating, reducing, or ameliorating the symptoms of a disease, dysfunction, or disorder in a mammal, such as a human that has, is suspected of having, or at risk for developing a disease or disorder associated with the abnormal proliferation of angiogenesis.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, drop bottles, tubes, pumps, bags, vials, containers, syringes, bottles, and any packaging material suitable for a selected formulation and intended mode of administration and treatment. A wide array of ophthalmic compositions provided herein are contemplated as are a variety of treatments for any disease, disorder, or condition that would benefit by controlled release administration of an ophthalmic agent to the eye.

In some embodiments, a kit includes one or more additional containers, each with one or more of various materials (such as rinses, wipes, and/or devices) desirable from a commercial and user standpoint for use of a formulation described herein. Such materials also include labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the ophthalmic compositions are presented in a dispenser device which contains one or more unit dosage forms containing a compound provided herein. In a further embodiment, the dispenser device is accompanied by instructions for administration. In yet a further embodiment, the dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

III. METHODS OF SYNTHESIS

In an aspect, provided herein is a method of preparing a pharmaceutical composition, comprising a compound of Formula (I), or an isotopic variant, tautomer, pharmaceutically acceptable salt, solvate, or hydrate thereof; and at least one pharmaceutically acceptable excipient, wherein the pharmaceutical composition is formulated as a suspension, comprising:

(i) micronizing the compound of Formula (I), or an isotopic variant, tautomer, pharmaceutically acceptable salt, solvate, or hydrate thereof;

(ii) sterilizing the micronized compound of Formula (I), or an isotopic variant, tautomer, pharmaceutically acceptable salt, solvate, or hydrate thereof, and (iii) admixing a therapeutically effective amount of the compound of Formula (I), or an isotopic variant, tautomer, pharmaceutically acceptable salt, solvate, or hydrate thereof with the least one pharmaceutically acceptable excipients.

In an aspect, provided herein is a method of preparing a pharmaceutical composition, comprising fine particles of a compound of Formula (I), or an isotopic variant, tautomer, pharmaceutically acceptable salt, solvate, or hydrate thereof; and at least one pharmaceutically acceptable excipient, wherein the pharmaceutical composition is in a dosage form for ophthalmic dosing or administration, comprising:

(i) micronizing the compound of Formula (I), or an isotopic variant, tautomer, pharmaceutically acceptable salt, solvate, or hydrate thereof;

(ii) sterilizing the micronized compound of Formula (I), or an isotopic variant, tautomer, pharmaceutically acceptable salt, solvate, or hydrate thereof; and (iii) admixing a therapeutically effective amount of the compound of Formula (I), or an isotopic variant, tautomer, pharmaceutically acceptable salt, solvate, or hydrate thereof with the least one pharmaceutically acceptable excipients.

In some embodiments, a suspension comprising particles of the compound of Formula (I), or an isotopic variant, tautomer, pharmaceutically acceptable salt, solvate, or hydrate thereof is formed.

In some embodiments, the sterilization is performed before the admixing. In some embodiments, the sterilization is performed after the admixing.

In some embodiments, the sterilization is performed at a temperature of about 121° C. In some embodiments, the sterilization is performed for a period of from about 20 to about 30 minutes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

IV. EXAMPLES

Examples 1-5 summarize the development of KDR2-2 Suspension Eye Drop, 0.1% w/v, which is indicated for the treatment of corneal neovascularization. Initially, the quality target product profile (QTPP) was defined based on the properties of the drug substance. Our investigation during pharmaceutical development focused on those CQAs that could be impacted by a realistic change to the drug product formulation or manufacturing process. For KDR2-2 Suspension Eye Drop, these CQAs included appearance, particle size, viscosity, osmotic pressure, pH, assay, impurity, visible particles and sterile. The drug substance used for our development and the pivotal batch manufacturing was sourced from Asymchem Life Science (Tianjin) Co., Ltd. (No. 71, 7th Avenue, TEDA Tianjin, 300457, P.R. China). For formulation development, excipient grade selection was based on experience or supplier recommendation, level of the key excipient was optimized. For process development, this includes micronization, sterilization, filtration and mixing steps. Micronization, sterilization, filtration and mixing step were identified as critical process parameters (CPPs) and acceptable ranges were identified. During preparation, an acceptable range for assay and particle size was identified.

Scale-up principles and plans were discussed for scaling up from lab to pilot scale (~50.0 kg common blend). A ~50.0 kg cGMP exhibit batch was manufactured at pilot scale. The operating ranges for identified CPPs at commercial scale were proposed and will be qualified and continually verified during routine commercial manufacture. Finally, a control strategy that process parameters identified as potentially high risk variables was proposed. Our control strategy also includes in-process controls and finished product specifications. The process will be monitored during the lifecycle of the product and additional knowledge gained will be utilized to make adjustments to the control strategy as appropriate.

Example 1: Product Target Quality Profile/Drug Product

Based on the physicochemical characteristics of the KDR2-2 performed during early development stage, a target product profile was established to guide the development of KDR2-2 Suspension Eye Drop.

TABLE 1

Product Target Quality Profile for KDR2-2 Suspension Eye Drop, 0.1% w/v

| Feature | Target | Justification |
|---|---|---|
| Dosage form | Suspension Eye Drop | According to the physicochemical properties of the drug substance and clinical needs |
| Route of administration | Ophthalmic | According to the physicochemical properties of the drug substance and clinical needs |
| Dosage strength | 0.1% | According to the physicochemical properties of the drug substance and clinical needs |
| Stability | At least 24-month shelf-life at room temperature and protected from light | Support a 24 month expiration for the product |
| Drug product quality attributes | Appearance<br>Identification<br>Particle size<br>Sedimentation volume ratio<br>Osmotic pressure<br>Viscosity<br>pH<br>Assay of sodium thiosulfate<br>Assay<br>Impurity<br>Visible particles<br>Content uniformity<br>Sterile<br>Leachables/Extractables | Meeting the applicable quality standards (i.e., identity, assay and purity) |
| Container closure system | Suitable container closure system to achieve the target shelf-life and to ensure suspension eye drop integrity during shipping | Low density polyethylene single dose eye drops bottles, PET/AI/PE packaging and carton packaging are selected based on stability studies during development. |
| Administration/concurrence with labeling | Three times/day, three drops/time | According to the physicochemical properties of the drug substance and clinical needs |
| Alternative methods of administration | None | None |

Table 2 summarizes the quality attributes of KDR2-2 Suspension Eye Drop and indicates which attributes were classified as drug product critical quality attributes (CQAs). For this product, particle size, sedimentation volume ratio, osmotic pressure, viscosity, pH, assay of sodium thiosulfate, content uniformity, assay and impurity are identified as the subset of CQAs that have the potential to be impacted by the formulation and/or process variables.

TABLE 2

| Critical and Non-critical Quality Attributes of KDR2-2 Suspension Eye Drop, 0.1% w/v | |
|---|---|
| Drug Product quality attributes | Target |
| Appearance (color and dispersion) | White suspension; no agglomerate or aggregate, easy to disperse after shaking |
| Particle Size | D90 < 40 μm |
| Sedimentation volume ratio | Sedimentation volume ratio greater than 0.90 |
| Osmotic pressure | Osmotic pressure molar concentration range 260-320 mOsm/kg |
| Viscosity | USP/NF <912>Method 1 |
| pH | 5.5-8.0 |
| Assay of Sodium thiosulfate | Sodium thiosulfate ($Na_2S_2O_3$) in this product range 90.0% to 110.0% of the labeled amount |
| Assay | KDR2-2($C_{21}H_{14}F_3N_5O_2$) in this product range 90.0% to 110.0% of the labeled amount |
| Impurity | Single Impurity* ≤ 0.5%<br>Total Impurity* ≤ 2.0% |
| Visible particles | USP/NF <790> |
| Content Uniformity | USP/NF <905> |
| Sterile | USP/NF <71> |
| Leachables/ Extractables | USP <1663> and <1664> |

Chemical Name:

2-(2-Aminopyrimidin-4-yloxy)-N-(3-(trifluoromethyl)phenyl)quinoline-5-carboxamide Chemical Structure:

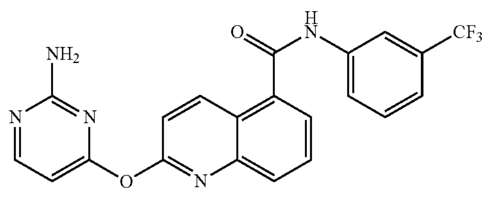 [SMILES: Nc1nccc(Oc2ccc3c(C(=O)Nc4cccc(C(F)(F)F)c4)cccc3n2)n1]

Molecular formula: $C_{21}H_{14}F_3N_5O_2$

Molecular weight: 425.36

Physical description: White solid

Physical-chemical Characteristics of the Drug Substance

Aqueous Solubility:

The solubility of KDR2-2 in different media was measured and is presented in Table 3.

TABLE 3

| Solubility of KDR2-2 in different media | | | |
|---|---|---|---|
| Medium | Solubility | Medium | Solubility |
| Methanol | 6.3 < S < 9.5 | Ethyl acetate | 3.8 < S < 4.6 |
| Ethanol | 2.4 < S < 2.7 | Methyl tert-butyl ether | S < 1.2 |
| Iso-propyl alcohol | S < 1.1 | Tetrahydrofuran | S > 18.0 |
| Acetonitrile | 1.7 < S < 1.9 | Dimethylsulfoxide | S > 28.0 |
| Acetone | 7.7 < S < 11.5 | Chloroform | S < 1.1 |
| Acetone/Water | 7.3 < S < 11.0 | Toluene | S < 0.9 |
| Methyl isobutyl ketone | 1.8 < S < 2.2 | Water | S < 1.1 |

Particle sizes: KDR2-2 is a poorly soluble drug with large particle sizes. The drug substance should be micronized to meet the quality standards of KDR2-2 Suspension Eye Drop. The result of microscopic observation of KDR2-2 (Batch #CK0120554-02-03P-01-32-01) in 1% Kolliphor® HS 15 is shown in FIG. 1, and the particle sizes of KDR2-2 (Batch #CK0120554-02-03P-01-32-01) in 1% Kolliphor® HS 15 were measured by malvern and is presented in Table 4.

TABLE 4

| Particle size results of KDR2-2 API, batch # CK0120554-02-03P-01-32-01 | | | |
|---|---|---|---|
| Sample | D10 (μm) | D50 (μm) | D90 (μm) |
| 1 | 55.9 | 162 | 375 |
| 2 | 33.0 | 105 | 292 |
| 3 | 45.5 | 138 | 353 |

Example 2: Excipient Compatibility Study

The excipients used in KDR2-2 Suspension Eye Drop were selected based on the excipient compatibility studies and the intent to prepare a simple suspension eye drop formulation with acceptable physical/chemical characteristics while providing good manufacturability using our process. A summary of the excipient-drug substance compatibility studies and the selection of each excipient grade are provided in this example.

Referring to the drug stability guiding principle, the pilot samples (Batch #FNB190016-002) and blank excipient solution (Batch #FNB190016-003) were stored at 60° C., 40° C. and illumination (4500 Lx±500 Lx) for 5, 10, and 30 days. Excipient-drug substance compatibility was assessed through the results of appearance, pH, viscosity, osmotic pressure, particle size, assay and impurity, which are summarized in Table 6. Common excipients functioning as polymer suspending agent, solubilizer, pH adjuster, osmotic pressure regulator and antioxidant were evaluated in the excipient compatibility study.

TABLE 5

| Summary of KDR2-2 Suspension EyeDrop Excipients | | | | | |
|---|---|---|---|---|---|
| | Ingredients | | | | |
| Product Name | Polymer Suspending Agent | Wetting Agent | pH Adjuster | Osmotic Pressure Regulator | Antioxidant |
| KDR2-2 Suspension Eye Drop | Hypromellose (HPMC E4M) | Polyoxyl 15-hydroxystearate (Kolliphor ® HS 15) | Sodium Dihydrogen Phosphate Dihydrate ($NaH_2PO_4$•$2H_2O$, di-Sodium Hydrogen Phosphate Dodecahydrate ($Na_2HPO_4$•$12H_2O$) | | |

TABLE 6

Excipient compatibility result for KDR2-2 Suspension EyeDrop, 0.1% w/v, batch # FNB190016-002 and FNB190016-003

| Samples | Conditions | | Appearance | pH | Viscosity (mPa · s) | Osmotic Pressure (mOsm/kg) | Particle Size (D90, μm) | Assay % | Total Impurity* (%) |
|---|---|---|---|---|---|---|---|---|---|
| Specification | | | White suspension; No agglomerate or aggregate, easy to disperse after shaking | 5.0-8.0 | Report Value | 260-320 | D < 40 μm | 90.0% to 110.0% of the labeled amount | ND |
| FNB190016-002 | | 0 day | White suspension; No agglomerate or aggregate, easy to disperse after shaking | 7.28 | 13.8 | 277 | 13.8 | 95.3 | 0.13 |
| | 60° C. | 5 days | White suspension; No agglomerate or aggregate, easy to disperse after shaking | 7.23 | 16.00 | 275 | 23.6 | 95.6 | ND |
| | | 10 days | White flocculent precipitates | 7.23 | 17.32 | 275 | 21.6 | 96.7 | 0.92 |
| | | 30 days | Some samples approached to the clarified liquid | 7.23 | 16.77 | 293 | 16.3 | 95.9 | 0.07 |
| | 40° C. | 5 days | White suspension; No agglomerate or aggregate, easy to disperse after shaking | 7.23 | 13.83 | 279 | 18.8 | 97.4 | ND |
| | | 10 days | White suspension; No agglomerate or aggregate, easy to disperse after shaking | 7.23 | 15.94 | 276 | 18.4 | 95.0 | 0.11 |
| | | 30 days | White suspension; No agglomerate or aggregate, easy to disperse after shaking | 7.28 | 12.48 | 289 | 14.6 | 97.6 | ND |
| | Illumination | 5 days | White suspension; No agglomerate or aggregate, easy to disperse after shaking | 7.25 | 16.13 | 275 | 17.2 | 93.4 | ND |
| | | 10 days | White suspension; No agglomerate or aggregate, easy to disperse after shaking | 7.25 | 17.38 | 274 | 17.0 | 94.5 | ND |

TABLE 6-continued

Excipient compatibility result for KDR2-2 Suspension EyeDrop, 0.1% w/v, batch # FNB190016-002 and FNB190016-003

| Samples | Conditions | Appearance | pH | Viscosity (mPa · s) | Osmotic Pressure (mOsm/kg) | Particle Size (D90, μm) | Assay % | Total Impurity* (%) |
|---|---|---|---|---|---|---|---|---|
| | 30 days | White suspension; No agglomerate or aggregate, easy to disperse after shaking | 7.26 | 11.71 | 290 | 17.1 | 94.5 | 0.06 |

*When the impurity below 0.05%, it is reported as "N.D". Only when the impurity is higher than 0.05%, then it will be calculated as total impurity White flocculent precipitates were appeared in KDR2-2 Suspension Eye Drop after the samples were stored at 60° C. for 10 days, and some samples approached to clarified liquid for 30 days. There is no obvious change in appearance, assay and impurity of KDR2-2 Suspension Eye Drop and the blank solution in 40° C. and illumination for 30 days. Therefore, it is believed that the excipients are compatible with the drug substance. The compatibility of the drug substance with excipients was again confirmed by the stability studies on submission batches. The results of such studies under accelerated conditions (40° C./NMT 25% RH) are summarized below.

Excipient Grade Selection

Based on the results of excipient compatibility studies, hypromellose (HPMC E4M), polyoxyl 15-hydroxystearate (Kolliphor® HS 15), sodium dihydrogen phosphate dehydrate ($NaH_2PO_4 \cdot 2H_2O$), di-sodium hydrogen phosphate dodecahydrate ($Na_2HPO_4 \cdot 12H_2O$), sodium chloride and sodium thiosulfate were selected for the product development. The selection of excipient grade and supplier was based on previous formulation experience and knowledge about excipients that have been used successfully in approved products manufactured. The level of excipients used in the formulation was studied in subsequent formulation development studies.

TABLE 7

Initial selection of excipient type and grade

| Ingredients | Grade | Supplier | Function |
|---|---|---|---|
| Hypromellose (HPMC E4M) | NF | Dow | Polymer suspending agent |
| Polyoxyl 15-Hydroxystearate (Kolliphor ® HS 15) | NF | BASF | Wetting agent |
| Sodium Dihydrogen Phosphate Dihydrate ($NaH_2PO_4 \cdot 2H_2O$) | NF | Merck | pH adjuster |
| di-Sodium Hydrogen Phosphate Dodecahydrate ($Na_2HPO_4 \cdot 12H_2O$) | NF | Merck | pH adjuster |
| Sodium Chloride | NF | Merck | Osmotic pressure regulator |
| Sodium Thiosulfate | NF | Sinopharm | Antioxidant |

Hypromellose (HPMC E4M):

Hypromellose (HPMC E4M) is widely used as polymer suspending agent for Suspension Eye Drop. The product name is METHOCEL™.

Polyoxyl 15-Hydroxystearate (Kolliphor® HS 15):

Polyoxyl 15-Hydroxystearate is a new kind of excipient with high solubilization ability and low histamine release, low hemolytic activity and excellent physiological tolerance, which is approved for injection. Its safety is support by listed products and clinical research data.

Sodium Dihydrogen Phosphate Dihydrate ($NaH_2PO_4 \cdot 2H_2O$):

It is widely used as pH adjuster, the product sourced from Merck with injection grade was selected, which residual solvents and microbial limits should meet the requirements.

Di-Sodium Hydrogen Phosphate Dodecahydrate ($Na_2HPO_4 \cdot 12H_2O$):

It is widely used as pH adjuster, the product sourced from Merck with injection grade was selected, which residual solvents and microbial limits should meet the requirements.

Sodium Chloride:

Sodium chloride is widely used as osmotic pressure regulator, the product sourced from Merck with injection grade was selected, which residual solvents and microbial limits should meet the requirements.

Sodium Thiosulfate:

Sodium thiosulfate as an antioxidant, sourced from Sinopharm Chemical Reagent Co., Ltd. The quality should meet the requirements. The continue production will use Merck brand for clinical use.

Excipient Dosage Selection

Based on the initial formulation development, it is determined that the dosage of excipients meets the Inactive Ingredient Database (IIG) and the conventional dosage of excipients published in the Excipients Database of the National Drug Evaluation Center which is shown in Table 8.

TABLE 8

Excipient dosage of KDR2-2 Suspension Eye Drop, 0.1% w/v

| Ingredients | Per Dose (mg) | Daily Dosage* | IIG Dosage** |
|---|---|---|---|
| Hypromellose (HPMC E4M) | 2.00 | 4 mg/mL | 5 mg/mL |
| Polyoxyl 15-Hydroxystearate (Kolliphor ®) HS 15) | 22.50 | 4.50% w/w | N/A |
| Sodium Dihydrogen Phosphate Dihydrate ($NaH_2PO_4 \cdot 2H_2O$) | 1.04 | 0.21% | 1.15% |
| di-Sodium Hydrogen Phosphate Dodecahydrate ($Na_2HPO_4 \cdot 12H_2O$) | 8.00 | 1.60% | 1.67% |
| Sodium Chloride | 1.50 | 0.30% | 0.68% |
| Sodium Thiosulfate | 0.50 | 0.10% | 0.19% |

*The daily usage is three times a day, three drops each time.

**The dosage of IIG used in the ophthalmic preparation, wherein the IIG of sodium thiosulfate is used in intravenous. The data shows that the content of Kolliphor ® HS 15 in the injection product (Panitol) is 50%.

The dosage of excipients used in this product is lower than the IIG dosage of the ophthalmic preparation or the intravenous preparation provided by the FDA approved drug inactive ingredient database.

Example 3. Drug Product Formulation Development

Initial Formulation Development

The formulation development started with several small R&D batches (FNB180076-048-01 to FNB180076-065-03). The amount of each excipient in the formula was adjusted and optimized in these batches to give our drug product acceptable physical characteristics. All of these adjustments led to prototype formulation FNB180076-065-03, which showed acceptable physical characteristics. Some of the bench scale trials are listed in Table 9. Table 10 provides physical characterizations of the lead bench scale-formulation. The results suggested that the basic composition developed during bench scale trials can produce acceptable physical characteristics. By evaluating the physicals of above trial batches, it is illustrated that the osmotic pressure of the preparation could be affected by di-sodium hydrogen phosphate dodecahydrate, sodium chloride and sodium thiosulfate, the concentration of Hypromellose (HPMC E4M) affected the viscosity of the formulation. In order to reduce the sedimentation of the drug substance, FNB180076-065-03 was selected as lead bench scale formulation.

TABLE 9

Compositions of initial formulation trials, KDR2-2 Suspension Eye Drop, 0.1% w/v, Batch # FNB180076-048-01, 050-02, 050-03, 052-01, 052-03, 058-01, 058-03, 065-01, 065-02 and 065-03

| | KDR2-2 Suspension Eye Drops, 0.1% w/v, Batch # FNB180076- (mg/Vial) | | | | | | | | | |
|---|---|---|---|---|---|---|---|---|---|---|
| Ingredients | 048-01 | 050-02 | 050-03 | 052-01 | 052-03 | 058-01 | 058-03 | 065-01 | 065-02 | 065-03 |
| KDR2-2 | 0.50 | 0.50 | 0.50 | 0.50 | 0.50 | NA | NA | 0.50 | 0.50 | 0.50 |
| Hypromellose (HPMC E4M) | 2.50 | 2.50 | 2.50 | 2.50 | 2.50 | 2.50 | 2.50 | 1.75 | 2.00 | 2.25 |
| Polyoxyl 15-Hydroxystearate (Kolliphor ® HS 15) | 22.50 | 22.50 | 22.50 | 22.50 | 22.50 | 22.50 | 22.50 | 22.50 | 22.50 | 22.50 |
| Sodium Dihydrogen Phosphate Dihydrate ($NaH_2PO_4$•$2H_2O$) | 1.04 | 1.04 | 1.04 | 1.04 | 1.04 | 1.04 | 1.04 | 1.04 | 1.04 | 1.04 |
| di-Sodium Hydrogen Phosphate Dodecahydrate ($Na_2HPO_4$•$12H_2O$) | 8.00 | 8.00 | 8.00 | 6.00 | 9.60 | 8.00 | 8.00 | 8.00 | 8.00 | 8.00 |
| Sodium Chloride | 0.50 | 0.50 | 0.50 | 0.50 | 0.50 | 1.00 | 1.50 | 1.50 | 1.50 | 1.50 |
| Sodium Thiosulfate | 0.50 | 1.00 | 1.50 | 0.50 | 0.50 | 0.50 | 0.50 | 0.50 | 0.50 | 0.50 |
| Add Purified Water to | 0.5 mL | 0.5 mL | 0.5 mL | 0.5 mL | 0.5 mL | 0.5 mL | 0.5 mL | 0.5 mL | 0.5 mL | 0.5 mL |

TABLE 10

Physicals of lead bench scale formulation for KDR2-2 Suspension Eye Drop, 0.1% w/v, Batch # FNB180076-048-01, 050-02, 050-03, 052-01, 052-03, 058-01, 058-03, 065-01, 065-02 and 065-03

| | KDR2-2 Suspension Eye Drop, 0.1% w/v, Batch # FNB180076- (mg/Vial) | | | | | | | | | |
|---|---|---|---|---|---|---|---|---|---|---|
| Ingredients | 048-01 | 050-02 | 050-03 | 052-01 | 052-03 | 058-01 | 058-03 | 065-01 | 065-02 | 065-03 |
| pH | 7.35 | 7.36 | 7.37 | 7.26 | 7.49 | 7.37 | 7.36 | 7.44 | 7.37 | 7.40 |
| Osmotic Pressure (mOsm/kg) | 238 | 254 | 270 | 209 | 261 | 267 | 301 | 297 | 297 | 294 |
| Viscosity (mPa · s) | 33.72 | 32.19 | 36.05 | 38.44 | 42.73 | NA | NA | 12.29 | 16.22 | 20.85 |
| Particle Size (D90, μm) | 66.20 | 88.0 | 15.7 | 69.2 | 56.5 | NA | NA | 5.07 | 4.76 | 4.95 |
| Assay (%) | 94.2 | 99.0 | 99.0 | 95.2 | 97.3 | NA | NA | 100.0 | 100.3 | 99.5 |

Preliminary Stability Study

Further R&D batches (batch #FNB180076-071-01, batch: 2000 vials) which contained the same level of ingredients as FNB180076-065-03 were evaluated to confirm stability under long-term conditions (25° C./65% RH). No pH, viscosity, osmotic pressure, particle size, assay and impurity were observed out of range, so it could be concluded that the formulation was stable and eligible for further development.

TABLE 11

Physicals of KDR2-2 Suspension Eye Drop under Long-term Conditions (25° C./65% RH)

| Physicals | Specification | T0 | 1 M | 2 M | 3 M |
|---|---|---|---|---|---|
| pH | 5.0-8.0 | 7.36 | 7.29 | 7.21 | 7.26 |
| Osmotic Pressure (mOsm/kg) | Report Value | 20.91 | 22.75 | 22.2 | 38.5 |
| Viscosity (mPa · s) | 260-320 | 297 | 304 | 316 | 307 |
| Particle Size (D90, μm) | D90 < 40 μm | 4.82 | 5.63 | 3.98 | 4.92 |
| Assay (%) | 90.0% to 110.0% of the labeled amount | 96.1 | 97.5 | 97.5 | 94.8 |
| Impurity (%) | Total Impurity* ≤ 2.0% | 0.39 | .035 | 0.40 | ND |

*When the impurity below 0.05%, it is reported as "<N.D". Only when the impurity is higher than 0.05%, then it will be calculated as total impurity.

The formulation composition was finalized based on Formulation Development Studies. The level of hypromellose (HPMC E4M), di-sodium hydrogen phosphate dodecahydrate, sodium chloride and sodium thiosulfate were optimized. The finalized formulation for KDR2-2 Suspension Eye Drop, 0.1% w/v, is presented in Table 12.

TABLE 12

| Ingredients | Function | Composition (% w/w) |
|---|---|---|
| KDR2-2 | Active | 0.1 |
| Hypromellose (HPMC E4M) | Polymer suspending agent | 0.4 |
| Polyoxyl 15-Hydroxystearate (Kolliphor ® HS 15) | Wetting agent | 4.5 |
| Sodium Dihydrogen Phosphate Dihydrate ($NaH_2PO_4$•$2H_2O$) | pH adjuster | 0.21 |
| di-Sodium Hydrogen Phosphate Dodecahydrate ($Na_2HPO_4$•$12H_2O$) | pH adjuster | 1.6 |
| Sodium Chloride | Osmotic pressure regulator | 0.3 |
| Sodium Thiosulfate | Antioxidant | 0.1 |

Example 4. Manufacturing Process Development

The process parameters that can potentially impact the finished product quality attributes. The process parameters used at the very first process step determine the quality attributes of the output material (intermediate) produced at this step. Process parameters of the intermediate from this step in the manufacturing process will determine quality attributes of the next intermediate and, eventually, those of the finished drug product. The API Micronization, API suspension sterilization process, hypromellose (HPMC E4M) preparation process, the blank solution filtration and the stirring/mixing process are CPPs of KDR2-2 Suspension Eye Drop, which were investigated and the product quality attributes were evaluated.

Drug Substance Particle Size Selection for Product Development

Figures 4, 5A, 5B:
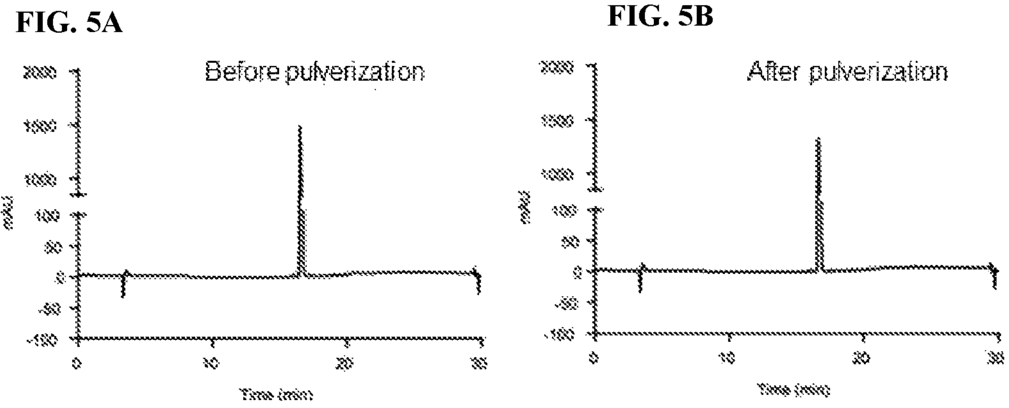
FIG. 4. is a graphic representation comparing the particle size distribution of KDR2-2 API before and after pulverization.
FIGS. 5A-5B. are chromatograms showing the purity of KDR2-2 API before and after pulverization.
Figures 6A, 6B, 6C, 6D, 6E:
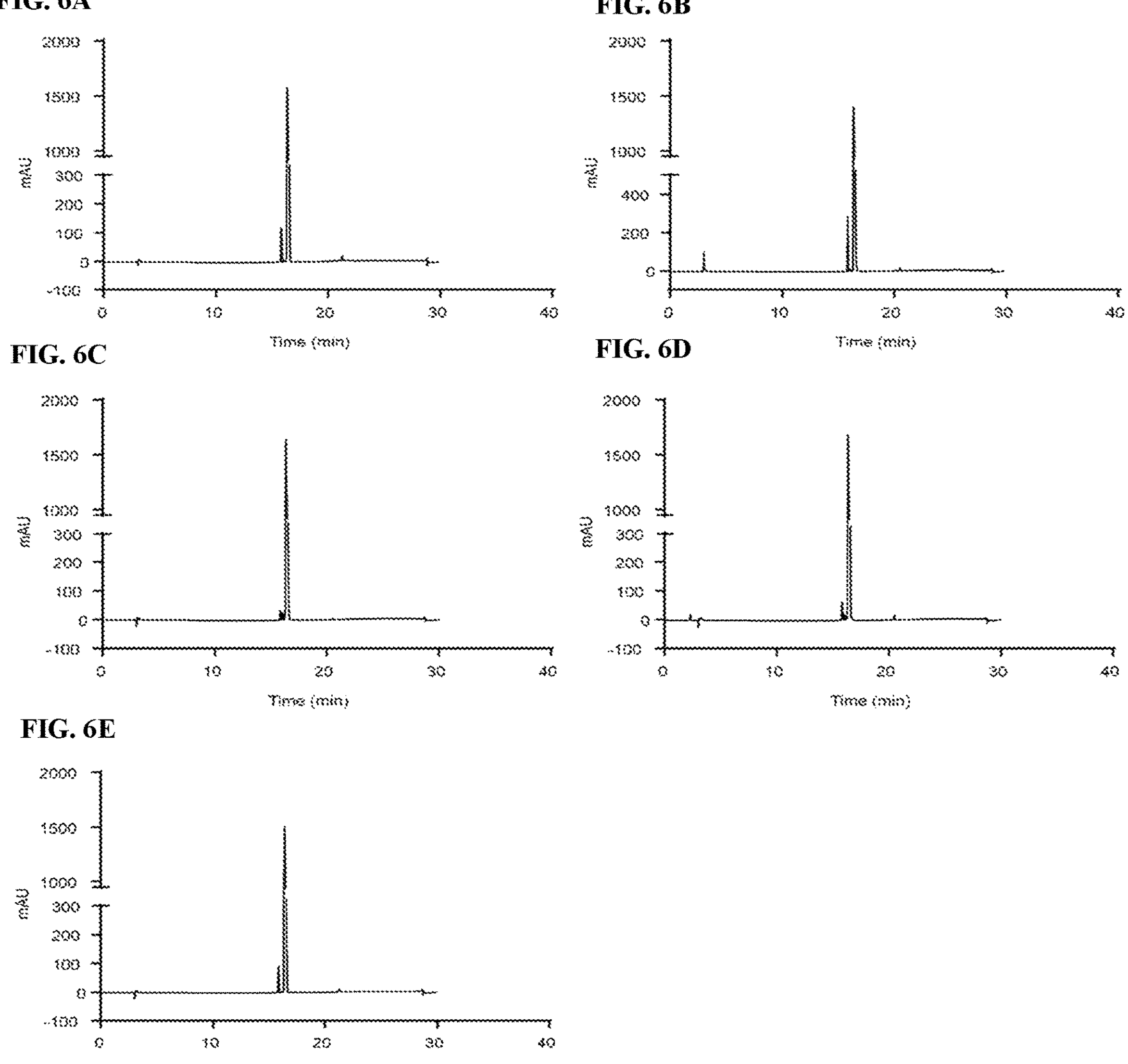
FIGS. 6A-6E. are chromatograms depicting the increase in degradation of KDR2-2 formulation at 40° C. over a three month period.
Figure 7:
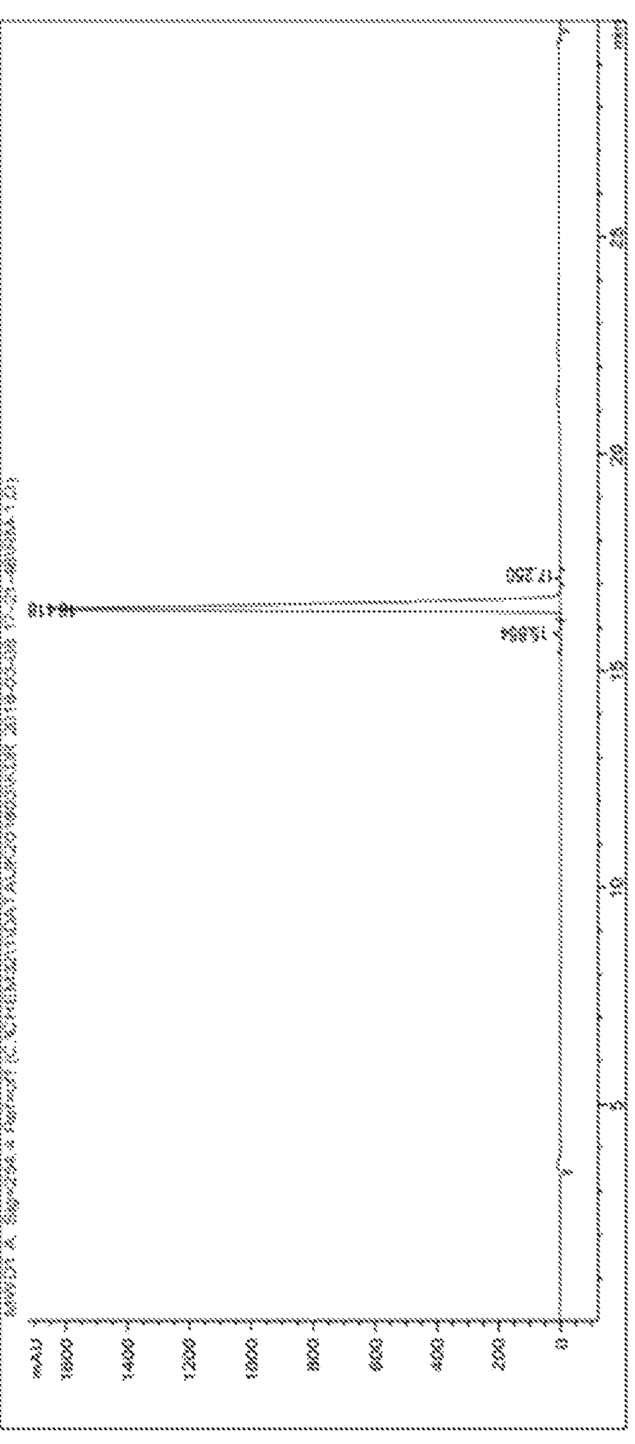
FIG. 7. is a chromatogram depicting the purity of KDR2-2 formulation.

The drug particle size for suspension eye drops should be reduced to level <10 μm in an attempt to avoid excessive lacrimation, the micronization process of drug substance was studied. The micronization process parameters of the jet are: injection pressure is 5 bar; crushing pressure is 3 bar. The particle size and distribution of the KDR2-2 API were measured before and after pulverization, to determine whether the API satisfies the formulation requirements after pulverization. The results are shown in FIGS. 4 and Table 13.

TABLE 13

Particle size results of KDR2-2 API after pulverization, Batch # CKo120554-02-03P-01-32-01

| Sample | D10 (μm) | D50 (μm) | D90 (μm) |
|---|---|---|---|
| 1 | 0.957 | 3.55 | 8.03 |
| 2 | 0.949 | 3.46 | 7.59 |
| 3 | 0.946 | 3.41 | 7.47 |

The API Suspension Sterilization Process Development

The purpose of the moist heat sterilization process is to ensure the API and product are sterile. Three sterilization methods of API were investigated: moist heat sterilization with API, moist heat sterilization with API, 0.1% Kolliphor® HS 15 and HPMC E4M, moist heat sterilization with API and 0.1% Kolliphor® HS 15, the particle size of the product were evaluated and the results are shown in Table 14.

TABLE 14

Effect of the API suspension sterilization process, Batch # FNB180076-130-01, 099-01 and 101

| Samples | Moist Heat Sterilization Process | Particle Size D90 (μm) |
|---|---|---|
| FNB180076-130-01 (batch: 2000 vials) | API only | 17.1 |
| FNB180076-099-01 (batch: 4000 vials) | API, 0.1% Kolliphor ® HS 15 and HPMC E4M | 61.7 |
| FNB180076-101 (batch: 2000 vials) | API and 0.1% Kolliphor ® HS 15 | 34.0 |

From particle size results, the moist heat sterilization with API only is applied for batch production that the particle size of the product was smaller than others.

Hypromellose (HPMC E4M) Preparation Process Development

HPMC E4M Preparation Processes:

(1) HPMC E4M is sterilized after dissolving, and added to the API suspension after cooling which is stirred and dispersed after sterilization with other excipients solution;

(2) HPMC E4M is added to the API suspension after dissolving, which is stirred and dispersed after sterilization with other excipients solution;

(3) HPMC E4M is mixed with other excipients solution and filtered by 0.65 μm and 0.2 μm membranes after dissolving, then added to the API suspension which is not dispersed after sterilization.

TABLE 15

Effect of HPMC E4M Preparation Process, Batch # FNB180076-071-01, 088 and 095

| Samples | HPMC E4M Preparation Processes | Particle Size D90 (μm) | Viscosity (mPa · s) |
|---|---|---|---|
| FNB180076-071-01 (batch: 2000 vials) | Process (1) | 4.82 | 20.91 |
| FNB180076-088 (batch: 25,000 vials) | Process (2) | 4.97 | 27.77 |
| FNB180076-095 (batch: 100,000 vials) | Process (3) | 17.1 | 16.44 |

For process (1), the particle size of the product was less than 10 μm, but the production line of Zhuhai ESSEX Bio-Pharmaceutical CO., Ltd. is only equipped with one sterilizable tank, so the process can't fit the workshop. The HPMC E4M concentration of batch FNB180076-071-01 and FNB180076-088 is 0.45%, the blank solution was difficult to filtrate with viscosity 27.77 mPas of the product, so the HPMC E4M concentration is adjusted to 0.40%. For process (3), the particle size of the product was more than 10 μm, but the particle size did not change significantly after the scale is enlarged, and the blank solution could be smoothly filtered and sterilized. The process (3) of HPMC E4M preparation process is applied for batch production.

The Blank Solution Filtration Process Development

Filtration is the process for removing microorganisms in liquid or gas by physical retention to achieve the quality requirements associated with sterile pharmaceuticals. The effects of filtration on the product should be investigated by filter adsorption experiments and compatibility experiments. PES and PVDF were selected, the blank solution was sterilized by filtration through a 0.2 μm filter, and the adsorption of the antioxidant sodium thiosulfate and impurities were evaluated. The results are shown in Table 16.

TABLE 16

Effect of the blank solution filtration process, Batch # FNB180076-079

| Samples | Assay of Sodium Thiosulfate (%) | Impurity (%) |
|---|---|---|
| FNB180076-079 (before filtration) | 102.5 | ND |
| FNB180076-079A (after filtration by PVDF) | 100.5 | ND |
| FNB180076-079A (Soak for 1 h after filtration) | 101.5 | ND |
| FNB180076-079A (Soak for 2 h after filtration) | 102.3 | ND |
| FNB180076-079 (Soak for 4 h after filtration) | 104.2 | ND |
| FNB180076-079B (after filtration by PES) | 101.5 | ND |
| FNB180076-079B (Soak for 1 h after filtration) | 101.8 | ND |
| FNB180076-079B (Soak for 2 h after filtration) | 102.5 | ND |
| FNB180076-079B (Soak for 4 h after filtration) | 102.5 | ND |

There was no significant change in the content of sodium thiosulfate before and after filtration of the blank solution. After soaking for 4 hours, no relevant substances were detected. It is indicated that the filtration of PES and PVDF did not cause correlation and adsorption The Stirring/Mixing Process Development The purpose of the stirring/mixing process is to obtain a suspension with uniform particle size. The influence of the stirring time on the particle size of the product is mainly investigated. From the particle size results, the longer of stirring time, the smaller of the particle size obtain of the product.

TABLE 17

Effect of Stirring/Mixing Time on the particle size of the product, Batch # FNB180076-130-01

| | | Stirring/Mixing Time | | | |
|---|---|---|---|---|---|
| Samples | Specification | 2 h | 4 h | 6 h | 24 h |
| FNB180076-130-01 (batch: 2000 vials) | Particle Size (D90, μm) | 22.4 | 30.4 | 32.7 | 17.1 |

Example 5. Scale-Up from Lab to Pilot Scale

Process development was conducted on the lab scale (1.0 kg). This section describes the principles used to scale-up the process to the pilot scale (~50.0 kg) in order to manufacture the exhibit batch. Table 18 below summarizes the different process scales.

TABLE 18

| Process scale summary | | | | |
|---|---|---|---|---|
| Product | Lab Scale | Pilot Scale | Major Change | Foundation |
| KDR2-2 Suspension Eye Drop, 0.4 mL:0.4 mg | 2,000 vials | 100,000 vials | Batch increase | From lab scale to pilot scale, there are no changes of the formulation and the equipment principles |

Scale-Up of the KDR2-2 API Micronization Process

The jet which has same mechanize with the one utilized during the drug substance particle size selection for product development studies was used for the pilot scale production. The LOD of pilot batch and scale up batches will be controlled the same range with lab scale. The particle size of API will be evaluated.

Scale-Up of the Batching System Sterilization Process

In order to ensure the quality of the filter, the flow rate of the filter element was tested before production. The first filter is equipped with 0.65 μm polyethersulfone filter and the second filter is equipped with 0.2 μm polyethersulfone filter, then both are connected with initial tank, and vacuum tank. The batching system was subjected to moist heat sterilization at a temperature of 121° C. for 30 minutes. After the sterilization is completed, the vacuum stirring tank was cooled to below 70° C.

Scale-Up of HPMC E4M Solution Preparation Process

The HPMC E4M was added to 60-70° C. water for injection, then stirred to a clear solution at room temperature and cooled to below 30° C.

Scale-Up of Kolliphor® HS 15 Solution Preparation Process

Kolliphor® HS 15 was melted to a liquid state in a 40-50° C. water bath, and accurately weighed after stirring evenly, then added water for injection below 30° C. and stirred.

Scale-Up of the API Suspension Sterilization Process

The API suspension sterilization process scale-up is summarized in Table 19.

TABLE 19

| Scale-up of the API suspension sterilization | | | |
|---|---|---|---|
| Scale | | Lab Scale | Pilot Scale |
| Batch Size | Kg | 1.0 | 50.75 |
| Sterilizer Capacity | L | 80 | 100 |
| Rotation Speed | rpm | 0 | 0 |
| Sterilization | ° C. | 121 | 121 |
| | min | 15 | 151 |
| Cooled after Sterilization | NA | Below 30° C. | Below 30° C. |

Scale-Up of the Blank Solution Preparation and Filtration Process

Sodium dihydrogen phosphate dihydrate, di-sodium hydrogen phosphate dodecahydrate, sodium chloride and sodium thiosulfate were added separately to the Kolliphor® HS 15 solution, and stirred until the material is completely dissolved and transferred to HPMC E4M solution, then the blank solution was mixed. The blank solution was filtrated by 0.65 μm and 0.2 μm filter to the API suspension, then the volume of KDR2-2 suspension was fixed with water for injection below 30° C.

Scale-Up of the Stirring/Mixing Process

The stirring/mixing process scale-up is summarized in Table 20.

TABLE 20

| Scale-up of the Stirring/Mixing | | | |
|---|---|---|---|
| Scale | | Lab Scale | Pilot Scale |
| Batch Size | Kg | 1.0 | 50.75 |
| Sterilizer Capacity | L | NA | 100 |
| Stirring time | rpm | More than 6 h | More than 6 h |
| Magnetic stirrer speed | rpm | 500-1000 | 400 |
| Mechanical agitator speed | NA | NA | 1200-1500 |
| Temperature | ° C. | Room temperature | Below 30° C. |

Scale-Up of the Filling Process

The KDR2-2 suspension was filled by BFS (Blowing Filling and Sealing) integration equipment.

Comparison of Manufacturing Equipment

The manufacturing equipment that will be used to manufacture of the proposed pilot batches is list in the table below.

TABLE 21

| Manufacturing Equipment | |
|---|---|
| Unit Operation | Equipment |
| Micronization | MC DecJet ® 30 |
| Sterilization | Batching System (100 L)/Steam sterilizer (0.6 m3) |
| Filtration | Batching System (100 L) |
| Stirring/Mixing | Batching System (100 L) |
| Filling | BFS integration equipment (9000 vials per hour) |

Exhibit Batch

Based on the development studies and the scale-up principles, Zhuhai ESSEX Bio-Pharmaceutical CO., Ltd. manufactured submission batches for 0.1% w/v (Bostal Batch #FNB190016-002), 0.1% w/v (ESSEX Batch #STH101-20190401) and 0.1% w/v (ESSEX Batch #STH101-20190402).

In the case, the KDR2-2 API micronization and sterilization, the preparation and filtration of blank solution, and stirring/mixing process were success and formulations were proven to process as expected according to the instructions in the batch records. Upon evaluation, the tables showed acceptable physiochemical and stability properties.

The submission batches were analyzed, evaluated and released as per the respective protocols and specifications. The purpose of these evaluations was to demonstrate that the formula and the manufacturing processes used in the production of KDR2-2 Suspension Eye Drop produced finished products that were within the pre-specified criteria. The results indicated that the physicochemical attributes of the new product were acceptable and in accordance to preset specifications in the corresponding evaluation protocols.

Batch Formula for Pivotal Batch

TABLE 22

Batch Formula for KDR2-2 Suspension Eye Drop, 0.1% w/v, Pivotal Batch # FNB190016-002, STH101-20190401 and STH101-20190402

| Ingredients | Function | Composition (% w/w) | Mg/vial |
|---|---|---|---|
| KDR2-2 | Active | 0.1 | 0.50 |
| Hypromellose (HPMC E4M) | Polymer suspending agent | 0.4 | 2.00 |
| Polyoxyl 15-Hydroxystearate (Kolliphor ® HS 15) | Wetting agent | 4.5 | 22.50 |
| Sodium Dihydrogen Phosphate Dihydrate ($NaH_2PO_4 \cdot 2H_2O$) | pH adjuster | 0.21 | 1.04 |
| di-Sodium Hydrogen Phosphate Dodecahydrate ($Na_2HPO_4 \cdot 12H_2O$) | pH adjuster | 1.6 | 8.00 |
| Sodium Chloride | Osmotic pressure regulator | 0.3 | 1.50 |
| Sodium Thiosulfate | Antioxidant | 0.1 | 0.50 |
| Water for Injection | | NA | Add to 0.50 mL |

Critical Process Parameters and in Process Controls

TABLE 23

Critical Process Parameters for Pivotal Batch for KDR2-2 Suspension Eye Drop, 0.1% w/v, Pivotal 0.1% w/v, Pivotal Batch # FNB190016-002, STH101-20190401 and STH101-20190402

| Critical Process | Equipment | Operation parameters | |
|---|---|---|---|
| Micronization | MC DecJet ® 30 | Injection pressure | 5 bar |
| | | Crushing pressure | 3 bar |
| Batching System Sterilization | Batching system | Sterilization temperature | 121° C. |
| | | Sterilization time | 30 minutes |
| | | Temperature after sterilization | Below 70° C. |
| HPMC E4M Solution Preparation | NA | WFI temperature | 60-70° C. |
| | | Temperature after dissolution | Below 30° C. |
| Kolliphor ® HS 15 Solution Preparation | NA | Water bath temperature | 40-50° C. |
| | | WFI temperature for dissolution | Below 30° C. |
| API Suspension Sterilization | Batching system | Sterilization temperature | 121° C. |
| | | Sterilization time | 15 minutes |
| | | Magnetic stirrer speed | 0 rpm |
| | | Temperature after sterilization | Below 30° C. |
| Filtration | Batching system | Flow of filter | NMT 23 mL/min |
| | | Pressure | 0.10-0.15 mPa |
| | | Volume to | 50.75 kg |
| Stirring/Mixing | Batching system | Stirring time | More than 6 hours |
| | | Magnetic stirrer speed | 400 rpm |
| | | Mechanical agitator speed | 1200-1500 rpm |
| | | Stirring temperature | Below 30° C. |
| Filling | BFS integration equipment | Filling volume | 0.5 mL |

Pivotal Batch Testing Results

The following section details evaluation of the Pivotal batch of the manufacturing.

Physical Characterizations Study

TABLE A

| Tests | Method of Analysis |
|---|---|
| pH | USP/NF <791> |
| Particle Size | General Notice of Ch. P Part four<0982>Method I |
| Osmotic Pressure | USP/NF<785> |
| Assay | B1839ACUID |
| Content Uniformity | USP/NF <905> B1839ACUID |
| Impurity | B1839I |
| Assay of Sodium thiosulfate | B1839A-ST |

The testing results are summarized as below.

TABLE 24

Physicals of KDR2-2 Suspension Eye Drop, 0.1% w/v of pH, particle size and Osmotic Pressure; Batch # FNB190016-002, STH101-20190401 and STH101-20190402

| | Batch # | | |
|---|---|---|---|
| Physicals | FNB190016-002 | STH101-20190401 | STH101-20190402 |
| pH | 7.32 | 7.38 | 7.34 |
| Particle Size (D90, μm) | 16.3 | 16.6 | 18.8 |
| Osmotic pressure (mOsm/kg) | 306.5 | 306.0 | 303.0 |

TABLE 25

Physicals of KDR2-2 Suspension Eye Drop, 0.1% w/v of Assay, Content Uniformity and Impurity; Batch # FNB190016-002, STH101-20190401 and STH101-20190402

| | | Batch # | | |
|---|---|---|---|---|
| Physicals | | FNB190016-002 | STH101-20190401 | STH101-20190402 |
| Assay (%) | | 94.9 | 99.2 | 95.0 |
| Content Uniformity (%) | | Meets requirements | Meets requirements | Meets requirements |
| Impurity (%) | Single Impurity | 0.06 | 0.05 | 0.05 |
| | Total Impurities | 0.11 | 0.05 | 0.05 |

TABLE 26

Assay of Sodium Thiosulfate of KDR2-2 Suspension Eye Drop, 0.1% w/v; Batch # FNB190016-002, STH101-20190401 and STH101-20190402

| | Batch # | | |
|---|---|---|---|
| Physicals | FNB190016-002 | STH101-20190401 | STH101-20190402 |
| Assay of Sodium Thiosulfate (%) | 95.2 | 97.7 | 99.0 |

TABLE 27

Finished Product Testing Results for KDR2-2 Suspension Eye Drop, 0.1% w/v; Batch # FNB190016-002

| Test | Method | Specification | Results |
|---|---|---|---|
| Appearance | G0001 Shake | White suspension; no agglomerate or aggregate, easy to disperse after shaking | White suspension; no agglomerate or aggregate, easy to disperse after shaking |
| Identification A | B1839ACUID | The retention time of the main peak of KDR2-2 in the sample solution chromatography should be consistent with that of the main peak in the reference solution chromatography | The retention time of the main peak of KDR2-2 in the sample solution chromatography was consistent with that of the main peak in the reference solution chromatography |
| Identification B | B1839ACUID | The UV chromatogram of the main peak of KDR2-2 in the sample solution should be consistent with the UV chromatogram of the main peak of the reference solution. | The UV chromatogram of the main peak of KDR2-2 in the sample solution was consistent with the UV chromatogram of the main peak of the reference solution |
| Particle Size | B1839PSD | D90 < 40 μm | 16.3 μm |
| Sedimentation volume ratio | G0007 | Sedimentation volume ratio greater than 0.90 | 0.99 |
| Osmotic pressure | USP/NF<785> | Osmotic pressure molar concentration range 260-320 mOsm/kg | 306.5 mOsm/kg |
| Viscosity | USP/NF <912>Method 1 | Report value | 17.00 mPa · s |
| pH | USP/NF <791> | 5.5-8.0 | 7.32 |
| Assay of Sodium thiosulfate | B1839A-ST | Sodium thiosulfate ($Na_2S_2O_3$) in this product range 90.0% to 110.0% of the labeled amount | 95.2% |
| Assay | B1839ACUID | KDR2-2 ($C_{21}H_{14}F_3N_5O_2$) in this product range 90.0% to 110.0% of the labeled amount | 94.9% |
| Impurity | B1839I | Single Impurity* ≤ 0.5%<br>Total Impurity* ≤ 2.0% | 0.06%<br>0.11% |
| Visible particles | USP/NF <790> | Meets requirements | Meets requirements |

TABLE 27-continued

| Finished Product Testing Results for KDR2-2 Suspension Eye Drop, 0.1% w/v; Batch # FNB190016-002 | | | |
|---|---|---|---|
| Test | Method | Specification | Results |
| Content Uniformity | USP/NF <905> B1839ACUID | Meets requirements | Meets requirements |
| Sterile | USP/NF <71> | Meets requirements | Meets requirements |

TABLE 28

| Finished Product Testing Results for KDR2-2 Suspension Eye Drop, 0.1% w/v; Batch # Suspension Eye Drop, 0.1% w/v; Batch #STH101-20190401 | | | |
|---|---|---|---|
| Test | Method | Specification | Results |
| Appearance | G0001 Shake | White suspension; no agglomerate or aggregate, easy to disperse after shaking | White suspension; no agglomerate or aggregate, easy to disperse after shaking |
| Identification A | B1839ACUID | The retention time of the main peak of KDR2-2 in the sample solution chromatography should be consistent with that of the main peak in the reference solution chromatography | The retention time of the main peak of KDR2-2 in the sample solution chromatography was consistent with that of the main peak in the reference solution chromatography |
| Identification B | B1839ACUID | The UV chromatogram of the main peak of KDR2-2 in the sample solution should be consistent with the UV chromatogram of the main peak of the reference solution | The UV chromatogram of the main peak of KDR2-2 in the sample solution was consistent with the UV chromatogram of the main peak of the reference solution |
| Particle Size | B1839PSD | D90 < 40 μm | 16.6 μm |
| Sedimentation volume ratio | G0007 | Sedimentation volume ratio greater than 0.90 | 0.98 |
| Osmotic pressure | USP/NF<785> | Osmotic pressure molar concentration range 260-320 mOsm/kg | 306.0 mOsm/kg |
| Viscosity | USP/NF <912>Method 1 | Report value | 17.62 mPa · s |
| pH | USP/NF <791> | 5.5-8.0 | 7.38 |
| Assay of Sodium thiosulfate | B1839A-ST | Sodium thiosulfate ($Na_2S_2O_3$) in this product range 90.0% to 110.0% of the labeled amount | 97.7% |
| Assay | B1839ACUID | KDR2-2($C_{21}H_{14}F_3N_5O_2$) in this product range 90.0% to 110.0% of the labeled amount | 99.0% |
| Impurity | B1839I | Single Impurity* ≤ 0.5%<br>Total Impurity* ≤ 2.0% | 0.05%<br>0.05% |
| Visible particles | USP/NF <790> | Meets requirements | Meets requirements |
| Content Uniformity | USP/NF <905> B1839ACUID | Meets requirements | Meets requirements |
| Sterile | USP/NF <71> | Meets requirements | Meets requirements |

TABLE 29

| Finished Product Testing Results for KDR2-2 Suspension Eye Drop, 0.1% w/v; Batch # Suspension Eye Drop, 0.1% w/v; Batch #STH101-20190402 | | | |
|---|---|---|---|
| Test | Method | Specification | Results |
| Appearance | G0001 Shake | White suspension; no agglomerate or aggregate, easy to disperse after shaking | White suspension; no agglomerate or aggregate, easy to disperse after shaking |
| Identification A | B1839ACUID | The retention time of the main peak of KDR2-2 in the sample solution chromatography should be | The retention time of the main peak of KDR2-2 in the sample solution chromatography was |

TABLE 29-continued

Finished Product Testing Results for KDR2-2 Suspension Eye Drop, 0.1% w/v; Batch # Suspension Eye Drop, 0.1% w/v; Batch #STH101-20190402

| Test | Method | Specification | Results |
|---|---|---|---|
| | | consistent with that of the main peak in the reference solution chromatography | consistent with that of the main peak in the reference solution chromatography |
| Identification B | B1839ACUID | The UV chromatogram of the main peak of KDR2-2 in the sample solution should be consistent with the UV chromatogram of the main peak of the reference solution. | The UV chromatogram of the main peak of KDR2-2 in the sample solution was consistent with the UV chromatogram of the main peak of the reference solution |
| Particle Size | B1839PSD | D90 < 40 μm | 18.8 μm |
| Sedimentation volume ratio | G0007 | Sedimentation volume ratio greater than 0.90 | 1.00 |
| Osmotic pressure | USP/NF<785> | Osmotic pressure molar concentration range 260-320 mOsm/kg | 303.0 mOsm/kg |
| Viscosity | USP/NF <912>Method 1 | Report value | 17.15 mPa · s |
| pH | USP/NF <791> | 5.5-8.0 | 7.34 |
| Assay of Sodium thiosulfate | B1839A-ST | Sodium thiosulfate ($Na_2S_2O_3$) in this product range 90.0% to 110.0% of the labeled amount | 99.0% |
| Assay | B1839ACUID | KDR2-2 ($C_{21}H_{14}F_3N_5O_2$) in this product range 90.0% to 110.0% of the labeled amount | 95.0% |
| Impurity | B1839I | Single Impurity* ≤ 0.5%<br>Total Impurity* ≤ 2.0% | 0.05%<br>0.05% |
| Visible particles | USP/NF <790> | Meets requirements | Meets requirements |
| Content Uniformity | USP/NF <905> B1839ACUID | Meets requirements | Meets requirements |
| Sterile | USP/NF <71> | Meets requirements | Meets requirements |

Container Closure System

The KDR2-2 Suspension Eye Drop, 0.10% w/v is packed in the following container closure systems.

TABLE 30

Packaging Configurations for KDR2-2 Suspension Eye Drop, 0.1% w/v, batch # FNB190016-002, STH101-20190401 and STH101-20190402

| | | | |
|---|---|---|---|
| Dosage | 0.1% w/v | 0.1% w/v | 0.1% w/v |
| Batch Number | FNB190016-002 | STH101-20190401 | STH101-20190402 |
| Batch Size | 100,000 vials | 100,000 vials | 100,000 vials |
| Packaging Size | 5 vials/blister, 4 blisters/pack, 2 packs/box | 5 vials/blister, 4 blisters/pack, 2 packs/box | 5 vials/blister, 4 blisters/pack, 2 packs/box |
| Low Density Polyethylene Single Dose Eye Drops Bottle Sizes | 1.0 mL/vial; 5 vials/blister | 1.0 mL/vial; 5 vials/blister | 1.0 mL/vial; 5 vials/blister |
| PET/AL/PE | 170*190 mm | 170*190 mm | 170*190 mm |
| Carton | 150*80*40 mm | 170*190 mm | 170*190 mm |

The proposed container/closure used for packaging our drug product complies with the applicable USP <661>, <671> requirements.

Microbiological Attributes

Materials and Methods

Thioglycolate fluid medium, tryptic soy mash liquid medium, tryptic soy agar medium, pH 7.0 sterile sodium chloride-peptone buffer, 1% polysorbate 80-pH 7.0 sterile chlorine Sodium-peptone buffer, 0.9% sterile sodium chloride solution, and so on.

Instruments and Appliances

HTY-601 type bacteria collection instrument, KAPY330 type bacteria culture incubator, sterile filter membrane (pore diameter not more than 0.45 m, diameter is 50 mm) and membrane filter, suction filter bottle, biochemical incubator and so on.

Sterile test tubes, sterile graduated straws, electronic turbidimeters or Maier's turbidimeters, sterile pipettes, scissors, inoculating rings, etc.

Preparation of Test Solution

KDR2-2 Suspension Eye Drop 60 samples squeeze into 600 mL of 1% polysorbate 80-pH 7.0 sterile sodium chloride-peptone buffer, shake until completely dissolved and clarified.

Assay

Using a KAPY330 triple colony incubator, aspirate a membrane with a pH 7.0 sterile sodium chloride-peptone buffer at a speed of 150-200 rpm, then pump KDR2-2 solution into the incubator for filtration, 300 mL each time, need 2 times. After the washing, 100 mL of thioglycolate fluid medium was pumped into each of the two incubators. The other incubator was pumped with 100 mL of tryptic soy mash liquid medium. Thioglycolate fluid medium—with less than 100 cfu/mL of *Staphylococcus aureus* 1 mL, was added as positive control bacteria, and 1% polysorbate 80 at pH 7.0 sterile sodium chloride-peptone buffer 100 mL. Instead of the test sample, the same operation as a negative control is performed. The thioglycolate fluid medium is cultured at 30 to 35° C., and the pancreatic soy meal liquid medium is cultured at 20 to 25° C.

TABLE 31

| The content of related ingredients in the packaging materials and preparations | | |
|---|---|---|
| Package material | Materials | Formulation |
| 5 antioxidants (3114, 1010, 330, 1076, 168) | not detected | not detected |
| 2- Mercaptobenzothiazole (2-MBT) | not detected | not detected |
| Methyl palmitate (μg/g) | 40.7 | not detected |
| Methyl stearate (μg/g) | 13.8 | not detected |
| DBB (μg/g) | 0.08 | not detected |
| DBP (μg/g) | 5.89 | not detected |
| DBHBA (μg/g) | 0.09 | not detected |

TABLE 32

| Determination of the content of each element in the packaging materiaL | | | | | | | | | |
|---|---|---|---|---|---|---|---|---|---|
| Element | Li | V | Cr | Mn | Fe | Co | Ni | Cu | Zn |
| Content (μg/g) | ND* | 0.1420 | 0.2423 | 0.2916 | 6.1306 | ND | ND | 3.4242 | 5.9545 |
| Element | As | Se | Mo | Ru | Rh | Pd | Ag | Cd | Sn |
| Content (μg/g) | ND | ND | 0.3629 | ND | ND | 0.1401 | 0.4193 | ND | 0.1037 |
| Element | Sb | Ba | Os | Ir | Pt | Au | Tl | Pb | Hg |
| Content (μg/g) | 46.3034 | 4.3197 | 0.1935 | 0.4664 | 2.2238 | 0.3799 | ND | 0.1425 | ND |

*ND indicates detected value less than 0.5 μg/L

The culture of the collection culture incubator should be observed day by day, not less than 14 days.

Cultivation and Observation

The incubator should be observed day by day during the culture and recorded for bacterial growth. If it is clarified within the time of the culture inspection, or if it is turbid, but it is confirmed that there is no microbial growth, it is judged that the test KDR2-2 formulation meets the requirements. If the medium is turbid during the cultivation process, after 14 days of culture, the presence or absence of microbial growth cannot be judged from the appearance. The medium can be transferred to the same fresh medium for 3 days if the medium is turbid again, or it can be taken the original culture solution, smeared, stained, and examined microscopically to determine whether there are bacteria.

Results

The positive control bacteria should grow well, and the negative control should not have bacteria growth. Otherwise, the experiment is invalid. If the KDR2-2 formulation medium is clarified, or although it is turbid, but confirmed to be aseptic growth, judge that the test product meets the requirements; the culture medium in any of the culture materials is turbid and confirms the growth of the bacteria, and the test sample is not It is in compliance with the regulations, unless it is sufficient to prove that the test results are invalid, that is, the growing microorganisms are not included in the test sample.

Compatibility

This product is a suspension eye drop. The results of the package compatibility study are shown in Tables 31 and 32.

The five antioxidants (3114, 1010, 330, 1076, 168) and 2-mercaptobenzothiazole (2-MBT) were not detected in the packaging materials and preparations. Contents of the lubricant methyl palmitate and methyl stearate in the packaging materials were 40.7 μg/g and 13.8 μg/g, respectively, were not detected in the preparations. The contents of the volatiles DBB, DBP, and DBHBA in the packaging materials were 0.08 μg/g, 5.89 μg/g, and 0.09 μg/g, respectively, were not detected in the preparation. The content of inorganic elements in the packaging material meets the requirements of the European Pharmacopoeia. Therefore, the selected single-dose eye drop bottle has good compatibility with the preparation and can be used as an inner package of KDR2-2 Suspension Eye Drop.

Control Strategy

The control strategy is the combination input material controls, process controls and monitoring, design spaces around individual or multiple unit operations, and final product specifications used to ensure consistent quality. For this product the control strategy for the proposed pilot scale process is listed in table below. In this table, the different elements of the control strategy are indicated in the third column. Operating ranges for the critical process parameters are contingent on scale up and validation. Specification and in-process controls are regulatory commitments for the proposed commercial process.

TABLE 33

Control strategy for Generic KDR2-2 Suspension Eye Drop, 0.1% w/v

| Factor | Attributes or Parameters | Range studied (lab scale) | Actual data for the exhibit batch (pilot scale) | Purpose of control |
|---|---|---|---|---|
| KDR2-2 API Micronization Process | | | | |
| Injection pressure | bar | 5 | 5 | To ensure the particle size of the product |
| Crushing pressure | bar | 3 | 3 | |
| KDR2-2 particle size | D90 | NMT 10 μm | NMT 10 μm | |
| Batching System Sterilization Parameters | | | | |
| 0.65 μm polyethersulfone filter | Flow rate | NA | NMT 23.0 mL/min | To ensure the integrity of the filter element |
| 0.2 μm polyethersulfone filter | Flow rate | NA | NMT 23.0 mL/min | |
| Batching system | Sterilization temperature | NA | 121° C. | To ensure the sterility of the equipment |
| | Sterilization time | NA | 30 minutes | |
| | Temperature after sterilization | NA | Below 70° C. | |
| HPMC E4M Preparation Parameters | | | | |
| WFI temperature | ° C. | 60 to 70° C. | 60 to 70° C. | To ensure that HPMC is completely soluble and the stability of the blank solution |
| Temperature after dissolution | ° C. | Below 30° C. | Below 30° C. | |
| Kolliphor ® HS 15 Solution Preparation Parameters | | | | |
| Water bath temperature | ° C. | 40 to 50° C. | 40 to 50° C. | To ensure the uniformity of excipient and the stability of the blank solution |
| WFI temperature for dissolution | ° C. | Below 30° C. | Below 30° C. | |
| API Suspension Sterilization Parameters | | | | |
| Sterilization temperature | ° C. | 121 | 121 | To ensure the sterility of the API and the product |
| Sterilization time | minutes | 15 | 15 | |
| Temperature after sterilization | ° C. | Below 30° C. | Below 30° C. | |
| Magnetic stirrer speed | rpm | 0 | 0 | |
| Filtration Parameters | | | | |
| Pressure | MPa | NA | 0.10 to 0.15 MPa | To ensure the sterility of the blank solution |
| Volume to | kg | NA | 50.75 | |
| Stirring/Mixing Parameters | | | | |
| Stirring time | hours | More than 6 hours | More than 6 hours | To ensure the particle size distribution of the product |
| Magnetic stirrer speed | rpm | 500 to 1000 | 400 | |
| Mechanical Agitator speed | rpm | NA | 1200 to 1500 | |
| Stirring temperature | ° C. | Room temperature | Below 30° C. | |
| Filling Parameters | | | | |
| Filling volume | mL | NA | 0.5 | To ensure the content uniformity of the product |

TABLE 34

| KDR2-2 Suspension Eye Drops, 0.1% w/v Release Specification | | |
|---|---|---|
| Test | Method | Specification |
| Appearance | G0001 Shake | White suspension; no agglomerate or aggregate, easy to disperse after shaking |
| Identification A | B1839ACUID | The retention time of the main peak of KDR2-2 in the sample solution chromatography should be consistent with that of the main peak in the reference solution chromatography |
| Identification B | B1839ACUID | The UV chromatogram of the main peak of KDR2-2 in the sample solution should be consistent with the UV chromatogram of the main peak of the reference solution. |
| Particle Size | B1839PSD | D90 < 40 μm |
| Sedimentation volume ratio | G0007 | Sedimentation volume ratio greater than 0.90 |
| Osmotic pressure | USP/NF<785> | Osmotic pressure molar concentration range 260-320 mOsm/kg |
| Viscosity | USP/NF <912>Method 1 | Report value |
| pH | USP/NF <791> | 5.5-8.0 |
| Assay of Sodium thiosulfate | B1839A-ST | Sodium thiosulfate ($Na_2S_2O_3$) in this product range 90.0% to 110.0% of the labeled amount |
| Assay | B1839ACUID | KDR2-2($C_{21}H_{14}F_3N_5O_2$) in this product range 90.0% to 110.0% of the labeled amount |
| Impurity | B1839I | Single Impurity* ≤ 0.5%<br>Total Impurity* ≤ 2.0% |
| Visible particles | USP/NF <790> | Meets requirements |
| Content Uniformity | USP/NF <905> B1839ACUID | Meets requirements |
| Sterile | USP/NF <71> | Meets requirements |

KDR2-2 API Micronization

The particle size of KDR2-2 API will be controlled by the pressure of injection and crushing.

Batching System Sterilization

The control strategy for batching system sterilization is to maintain the sterilization temperature and time.

HPMC E4M Preparation

The control strategy for HPMC E4M preparation is control the temperature of WFI when the HPMC E4M is added.

Kolliphor® HS 15 Solution Preparation

The control strategy for Kolliphor® HS 15 solution preparation is to keep the temperature when the Kolliphor® HS 15 is melting. The temperature of WFI should be controlled to avoid the formation of micelle.

API Suspension Sterilization

The control strategy for API Suspension Sterilization is to maintain the sterilization temperature, sterilization time and the temperature after sterilization.

Filtration

The time of blank solution filtration will be controlled by the pressure filtration.

Filling

The time of filling will be controlled by the filling volume.

Example 6. Study of the Stability of KDR2-2 Suspension Using Sodium Sulfite or Sodium Thiosulfate as Antioxidant Materials

- HPMC K15M
- Kolliphor® ELP (polyoxyl-35-castor oil), BASF
- KDR2-2 API
- Other reagents are commercially available analytical grade.

Instrument

- Laser diffraction particle size analyzer, Mastersizer 3000, Malvern, Birtain
- Osmometer, Osmomat 030, Gonotec, Germany
- PH Monitor, S20P, Mettler Toledo, Switzerland
- Balance, BSA124S, Sartorius, Germany
- UPLC, Agilent, USA Experimental Method KDR2-2 Suspension Formulation Stability Test Prepare the HPMC Solution (8 g/900 g)

8 g HPMC E4M was added into blue cap bottle, added water to 900 g, 60-70° C. water bath heat for dissolved. then stirred to a clear solution at room temperature and cooled to below 30° C., before the final preparation need 121° C. for 30 min or filter sterilization.

HPMC: K15M/E4M

Prepare the Wetting Reagent Solution

Kolliphor® HS 15 was melted to a liquid state in a 40-50° C. water bath, and accurately weighed after stirring evenly, then added water and phosphate buffer for, osmotic pressure regulator and antioxidant, then filter for sterilization by 0.22 μm membrane.

Wetting Reagent/Non-Ionic Solubilizer: Kolliphor® ELP/HS15

TABLE 35

| | Salt solution | |
|---|---|---|
| | Sodium sulfite | sodium thiosulfate |
| $NaH_2PO_4$•$2H_2O$ | 0.4860 g | 0.4846 g |
| $Na_2HPO_4$•$12H_2O$ | 4.4830 g | 4.4820 g |
| NaCl | 0.3851 g | 0.3850 g |
| ELP/HS 15 | 10.5 g | 10.5 g |
| Antioxidant (Sodium sulfite or sodium thiosulfate ) | 0.4677 g | 0.7047 g |
| Add water to | 70 g | 70 g |

Preparation of Suspension

Add 30 mL water and KDR2-2 micronization powder to blue cap bottle, 121° C. 30 min for sterilization. The temperature was cooled to below 70° C. then 60 g salt solution was added, stirred until the material is completely dissolved. Accelerated experiments and influential factor experiments were performed to determine potential, osmotic pressure, particle size, pH, content, and purity.

TABLE 36

| | Theoretical dosage | Concentration |
|---|---|---|
| KDR2-2 | 200 mg | 0.1% |
| $NaH_2PO_4$•$2H_2O$ | 0.416 g | 0.208% |
| $Na_2HPO_4$•$12H_2O$ | 3.84 g | 1.92% |
| HPMC solution (8 g/900 g) | 90 g | 0.4% |
| NaCl | 0.33 g | 0.165% |
| ELP (30 g/200 g) | 9 g | 4.5% |
| (Sodium sulfite or | Sodium sulfite: 0.4 g | 0.2% |
| sodium thiosulfate) | sodium thiosulfate: 0.6 g | 0.3% |
| Add water to | 200 g | 200 g |

| Ingredient | Function | Quality | % w/v |
|---|---|---|---|
| KDR2-2 | Active | 1.00 g | 0.10 |
| Hypromellose (HPMC E4M) | Polymer Suspending Agent | 4.00 g | 0.40 |
| Polyoxyl 15-Hydroxystearate (Kolliphor ® HS 15) | Solubilizer | 45.00 g | 4.50 |
| Sodium Dihydrogen Phosphate Dihydrate ($NaH_2PO_4$•$2H_2O$) | pH Adjuster | 2.10 g | 0.21 |
| Di-Sodium Hydrogen Phosphate Dodecahydrate ($Na_2HPO_4$•$12H_2O$) | pH Adjuster | 16.00 | 1.60 |
| Sodium Chloride | Osmotic Pressure Regulator | 3.00 g | 0.30 |
| Sodium Thiosulfate | Antioxidant | 1.00 g | 0.10 |
| Water | NA | Adjust to 1000 ml | NA |

Results and Discussion

Stability of Suspensions Containing Sodium Sulfite 1.1. The 0 Day Test Result standard curve: Y=70925X+466.51, $R^2$=0.9994, Percentage of average labeled amount (%)=100.19%, SD=0.69%

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| particle size (μm) | | 3.06 | | | 3.18 | | | 3.74 | |
| Osmotic pressure | | 254 | | | 258 | | | 251 | |
| pH | | 7.35 | | | 7.34 | | | 7.34 | |
| Percentage of labeled amount (%) | 99.9 | 101.1 | 101.1 | 100.5 | 100.6 | 100.5 | 99.2 | 99.4 | 99.5 |

-continued

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Percentage of average labeled amount of each group (%) | | 100.7 SD = 0.56% | | | 100.53 SD = 0.05% | | | 99.35 SD = 0.15% | |
| purity (%) | 98.967 | 99.710 | 99.732 | 99.723 | 99.730 | 99.753 | 99.744 | 99.708 | 99.700 |
| Appearance | No agglomerate or aggregate, easy to disperse after shaking. | | | | | | | | |

1.2. KDR2-2 Suspension Under Light (5000 Lux/90 Uw/Cm2) Test Result on Day 5

Percentage of average labeled amount (%)=102.17%, SD=2.13%

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Percentage of average labeled amount (%) | 101.8 | 104.7 | 104.2 | 104.3 | 102.3 | 102.3 | 99.1 | 98.8 | |
| Percentage of average labeled amount of each group (%) | | 103.54 SD = 1.26% | | | 102.96 SD = 0.95% | | | 98.92% SD = 0.16% | |
| purity (%) | 99.507 | 99.496 | 99.519 | 99.558 | 99.544 | 99.587 | 99.510 | 99.534 | |
| Appearance | No agglomerate or aggregate, easy to disperse after shaking. | | | | | | | | |

1.3. KDR2-2 Suspension Under High Temperature Test Result on Day 5

Percentage of average labeled amount (%)=86.42%, SD=0.50%

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Percentage of average labeled amount (%) | 85.6 | 85.5 | 86.5 | 86.8 | 87.0 | 86.8 | 86.8 | 86.3 | 86.6 |
| Percentage of average labeled amount of each group (%) | | 85.86 SD = 0.42% | | | 86.87 SD = 0.10% | | | 86.54 SD = 0.21% | |
| purity (%) | 93.946 | 93.941 | 93.908 | 93.75 | 93.472 | 93.754 | 94.284 | 94.278 | 94.266 |
| Appearance | Micelle | | | | | | | | |

2. Stability of Sodium Thiosulfate-Containing Suspensions 2.1 the 0 Day Test Result standard curve: 70925X+466.51, $R^2$=0.9994, Percentage of average labeled amount (%)=101.65%, SD=2.38%

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Particle size (μm) | | 3.55 | | | 3.71 | | | 4.15 | |
| Osmotic pressure (mOSMOL/KG) | | 272 | | | 274 | | | 275 | |
| pH | | 7.30 | | | 7.29 | | | 7.26 | |
| Percentage of labeled amount (%) | 102.4 | 107.0 | 102.5 | 97.4 | 100.6 | 101.1 | 101.3 | 100.8 | 101.8 |
| Percentage of average labeled amount of each group (%) | | 103.99 SD = 2.14% | | | 99.66 SD = 1.64% | | | 101.30 SD = 0.38 | |
| purity (%) | 99.779 | 99.600 | 99.732 | 99.787 | 99.768 | 99.796 | 99.677 | 99.791 | 99.772 |
| Appearance | No agglomerate or aggregate, easy to disperse after shaking. | | | | | | | | |
| Potential (mV) | 0.288 | | | | | | | | |

2.2. KDR2-2 Suspension Under Light (5000 Lux/90 Uw/Cm2) Test Result on Day 5

Percentage of average labeled amount (%)=102.75%, SD=2.23%

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Particle size (μm) | | 7.16 | | | 7.53 | | | 13.1 | |
| Osmotic pressure (mOSMOL/KG) | | 286 | | | 280 | | | 278 | |
| pH | | 7.28 | | | 7.31 | | | 7.34 | |
| Percentage of labeled amount (%) | 102.7 | 103.7 | 100.9 | 103.8 | 104.7 | 107.3 | 100.1 | 100.2 | 101.4 |
| Percentage of average labeled amount of each group (%) | | 102.44<br>SD = 1.14% | | | 105.25<br>SD = 1.46% | | | 100.57<br>SD = 0.60% | |
| Purity (%) | 99.722 | 99.717 | 99.725 | 99.687 | 99.640 | 99.676 | 99.720 | 99.734 | 99.737 |
| Appearance | No agglomerate or aggregate, easy to disperse after shaking. | | | | | | | | |
| Potential (mV) | | −0.0505 | | | 0.0381 | | | 0.128 | |

2.3. KDR2-2 Suspension Under High Temperature Test Result on Day 5

Percentage of average labeled amount (%)=100.67%, SD=0.69%

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Particle size (μm) | | 21.54 | | | 17.57 | | | 18.61 | |
| Osmotic pressure (mOSMOL/KG) | | 287 | | | 289 | | | 283 | |
| pH | | 7.17 | | | 7.17 | | | 7.18 | |
| Percentage of labeled amount (%) | 101.1 | 101.2 | 101.4 | 100.1 | 101.1 | 101.5 | 99.8 | 99.5 | 100.3 |
| Percentage of average labeled amount of each group (%) | | 101.21<br>SD=0.13% | | | 100.90<br>SD=0.61% | | | 99.90<br>SD=0.34% | |
| Purity (%) | 98.899 | 98.882 | 98.892 | 98.796 | 98.788 | 98.825 | 98.851 | 98.860 | 98.859 |
| Appearance | Micelle | | | | | | | | |
| Potential (mV) | | −0.0534 | | | −0.221 | | | 0.185 | |

2.4. KDR2-2 Suspension Under Light (5000 Lux/90 Uw/Cm2) Test Result on Day 10

Percentage of average labeled amount (%)=101.28%, SD=1.48%

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Particle size (μm) | | 8.18 | | | 6.06 | | | 5.45 | |
| Osmotic pressure (mOSMOL/KG) | | 275 | | | 273 | | | 276 | |
| pH | | 7.31 | | | 7.32 | | | 7.32 | |
| Percentage of labeled amount (%) | 99.8 | 100.7 | 100.1 | 99.8 | 100.2 | 101.1 | 103.2 | 103.4 | 103.3 |
| Percentage of average labeled amount of each group (%) | | 100.17<br>SD = 0.36% | | | 100.37<br>SD = 0.52% | | | 103.30<br>SD = 0.07% | |
| Purity (%) | 99.606 | 99.624 | 99.621 | 99.645 | 99.646 | 99.644 | 99.565 | 99.446 | 99.639 |
| Appearance | No agglomerate or aggregate, easy to disperse after shaking. | | | | | | | | |
| Potential (mV) | | 0.145 | | | −0.404 | | | −0.134 | |

2.5. KDR2-2 Suspension Under High Temperature Test Result on Day 10

Percentage of average labeled amount (%)=100.92%, SD=1.42%

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Particle size (μm) | | 16.48 | | | 18.11 | | | 16.13 | |
| Osmotic pressure (mOSMOL/KG) | | 289 | | | 298 | | | 297 | |
| pH | | 7.06 | | | 7.10 | | | 7.09 | |
| Percentage of labeled amount (%) | 100.1 | 100.1 | 100.0 | 102.1 | 103.9 | 102.5 | 100.0 | 100.0 | 99.6 |
| Percentage of average labeled amount of each group (%) | | 100.08 SD = 0.08% | | | 102.81 SD = 0.78% | | | 99.86 SD = 0.20% | |
| Purity (%) | 97.834 | 97.719 | 97.838 | 97.796 | 97.755 | 97.785 | 97.818 | 97.896 | 97.907 |
| Appearance | | | | | Micelle | | | | |
| Potential (mV) | | -0.211 | | | -0.646 | | | -0.0721 | |

3.1 Anti-Oxidant-Free Suspension Results in Accelerated Test in 3 Month

| | Sample 1 | | | Sample 2 | | | Sample 3 | | |
|---|---|---|---|---|---|---|---|---|---|
| | 1 | 2 | 3 | 1 | 2 | 3 | 1 | 2 | 3 |
| Particle size (μm) | | 3.83 | | | 5.27 | | | 3.89 | |
| Osmotic pressure (mOSMOL/KG) | | 296 | | | 292 | | | 290 | |
| pH | | 7.06 | | | 7.07 | | | 7.07 | |
| Percentage of labeled amount (%) | 89.31 | 88.73 | 89.00 | 87.44 | 87.16 | 87.13 | 89.04 | 89.13 | 91.57 |
| Percentage of average labeled amount of each group (%) | | 89.01 SD = 0.24% | | | 87.24 SD = 0.14% | | | 89.91 SD = 1.17% | |
| Purity (%) | 92.438 | 92.438 | 92.383 | 92.207 | 92.214 | 92.263 | 92.573 | 92.524 | 92.502 |
| Appearance | No agglomerate or aggregate, easy to disperse after shaking. | | | | | | | | |

Example 7. Micronization of Drug Substance

The drug substance should be micronized to meet the quality standards of KDR2-2 suspension formulation. Based on the results of excipient compatibility studies, hypromellose (HPMC E4M), polyoxyl 15-hydroxystearate (Kolliphor® HS 15), sodium dihydrogen phosphate dihydrate ($NaH_2PO_4{\cdot}2H_2O$), di-sodium hydrogen phosphate dodecahydrate ($NaH_2PO_412H_2O$), sodium chloride and sodium thiosulfate were selected for the product development. The selection of excipient grade and supplier was based on previous formulation experience and knowledge about excipients that have been used successfully in approved products manufactured. The level of excipients used in the formulation was studied in subsequent formulation development studies.

Critical Process Parameters (CPPs)

Particle Sizes: Micronization of Raw Materials

The drug particle size for suspension eye drops should be reduced to level <10 μm in an attempt to avoid excessive lacrimation, the micronization process of drug substance was studied. Certain amount of KDR2-2 API was taken and fed into a jet mill. The micronization process parameters of the jet are: injection pressure is 5 bar; crushing pressure is 3 bar; the media for micronization is air. The particle size and distribution of the KDR2-2 API was measured before and after pulverization using the dry method (Mastersizer 3000, Malvern), to determine whether the API satisfies the formulation requirements after pulverization. The results are as follows and in FIG. 4:

| Item | | Before micronization | After micronization |
|---|---|---|---|
| Particle size | Dv (10) | 2.33 μm | 0.304 μm |
| | Dv (50) | 10.5 μm | 1.75 μm |
| | Dv (90) | 472 μm | 3.83 μm |

API content was determined by liquid chromatography, Diamonsil® plus-C18 column (4.6×150 mm, 5 m), mobile phase: acetonitrile (with 0.2‰ trifluoroacetic acid):water (with 0.2‰ trifluoroacetic acid), acetonitrile gradient 5-95%, time: 17 min, column temperature 20° C., detection wavelength 254 nm. The results are shown as follows and in FIGS. 5A-5B:

| Item | | Before micronization | After micronization |
|---|---|---|---|
| HPLC peak (percentage | Impurity 1 | 15.969 min Peak area % = 0.08% | 16 min Peak area % = 0.085% |

-continued

| Item | | Before micronization | After micronization |
|---|---|---|---|
| of peak area) | KDR2-2 | 16.512 min Peak area % = 99.820% | 16.603 min Peak area % = 99.839% |
| | Impurity 2 | 17.28 min Peak area % = 0.101% | 17.406 min Peak area % = 0.075% |

Impurity 1 and Impurity 2 correspond to Intermediate A and Intermediate B as shown in Scheme 1 of Example 8.

Hypromellose Preparation Process Development: Screening of Suspending Agents, Using Suitable Medicinal Polymer Excipients as Suspending Agents Accurately weigh out 0.15 g of hypromellose (HPMC E4M), add 30 mL water (WFI, 60-70° C.), and then stir at room temperature to get a clear solution. Cool to below 30° C. for next usage. Then transfer solution to a 10 mL stoppered cylinder, mix upside down 3 times. Observe and take pictures at the time on 0, 3 h, 8 h, 12 h, 24 h.

| | 0.1% HPMC | 0.2% HPMC | 0.3% HPMC | 0.4% HPMC | 0.5% HPMC |
|---|---|---|---|---|---|
| HPMC K15M (0.15 g/30 mL) | 2 mL | 4 mL | 6 mL | 8 mL | 10 mL |
| KDR2-2 | 10 mg | 10 mg | 10 mg | 10 mg | 10 mg |
| Pure water | 8 mL | 6 mL | 4 mL | 2 mL | 0 mL |

The results show that sedimentation volume ratio of each group met the requirements of the Pharmacopoeia (>0.9). After 24 hours of preparation, the sedimentation volume ratios of the 0.4% and 0.5% concentration groups were same. Considering the safe dosage of HPMC K15M (≤0.5%), 0.4% was tentatively selected.

Wetting Reagent/Non-Ionic Solubilizer: Kolliphor® ELP/HS15

0.9 g HPMC was added into blue cap bottle, added water to 150 mL, 60-70° C. water bath heat for dissolved. Accurately weigh out 4.5 g of Kolliphor® HS15 add 30 mL water (WFI, 60-70° C.), and then stir at room temperature to get a clear solution. Cool to below 30° C. for next usage. Then transfer solution to a 10 mL stoppered cylinder, mix upside down 3 times. Observe and take pictures at the time on 0, 3 h, 12 h, 24 h.

| | prescription | | | | |
|---|---|---|---|---|---|
| component | 1% HS15 | 2% HS15 | 3% HS15 | 4% HS15 | 5% HS15 |
| HPMC (0.3 g/50 mL) | 10 mL | 10 mL | 10 mL | 10 mL | 10 mL |
| Kollophor ® HS 15 (2.25 g/15 mL) | 1 mL | 2 mL | 3 mL | 4 mL | 5 mL |
| KDR2-2 | 15 mg | 15 mg | 15 mg | 15 mg | 15 mg |
| $H_2O$ | 4 mL | 3 mL | 2 mL | 1 mL | 0 mL |

Osmotic Pressure Regulator and pH Adjuster

Sodium Dihydrogen Phosphate Dihydrate ($NaH_2PO_4{\cdot}2H_2O$): it is widely used as pH adjuster, the product sourced from Merck with injection grade was selected, which residual solvents and microbial limits should meet the requirements.

Di-Sodium Hydrogen Phosphate Dodecahydrate ($Na_2HPO_4{\cdot}12H_2O$): it is widely used as pH adjuster, the product sourced from Merck with injection grade was selected, which residual solvents and microbial limits should meet the requirements.

Sodium Chloride: sodium chloride is widely used as osmotic pressure regulator, the product sourced from Merck with injection grade was selected, which residual solvents and microbial limits should meet the requirements.

Sterilization Process

A. KDR2-2 drug substance was micronized, added into a brown vial and sealed and subsequently sterilized by steam sterilization at 121° C. for 30 minutes. At the same time dispersion medium solution (excipient solution) was prepared as prescribed, excipient solution by filtration through a 0.2 μm polyethersulfone (PES) microporous filter, then After the sterilization was completed, mix the KDR2-2 drug substance and the dispersion medium solution (excipient solution) under sterile conditions.

B. KDR2-2 drug substance was micronized, add all of the excipient substance except the HS 15 into a brown vial (total quality solution is 50 g) and sealed and subsequently sterilized by steam sterilization at 121° C. for 30 minutes, add the HS 15 which is by filtration through a 0.2 μm polyethersulfone.

C. KDR2-2 drug substance was micronized, HS 15 was prepared as prescribed (dissolve in water, total quality is 50 g), add them into a beaker. After by stirring, add the remaining prescription ingredients and sealed, sterilized by steam sterilization at 121° C. for 20 minutes.

Description of Production Process 1:

1. HPMC was added into 60-70° C. water (WFI) 1 L for swelling, then stirring to a clear solution at room temperature add more 2 L WFI.
2. HPMC sterilized by steam sterilization at 121° C. for 30 minutes. Cool to room temperature with stirring, marked as solution A.
3. Accurately weigh out 0.15 g of Kolliphor® HS15, add WFI then stir at room temperature to get a clear solution, marked as solution B.
4. Accurately weigh of $NaH_2PO_4{\cdot}2H_2O$, $Na_2HPO_4{\cdot}12H_2O$, sodium chloride, sodium thiosulfate as prescription, add WFI 1 L then stir at room temperature to get a clear solution, marked as solution C.
5. Mixed solution B and solution C, filtration through a 0.2 μm polyethersulfone (PES) microporous filter, marked as solution D.
6. Accurately weigh of KDR2-2 add WFI 1 L, sterilized by steam sterilization at 121° C. for 30 minutes, marked as API solution E.
7. Add solution D to the solution E, stirring to a clear solution, add solution A, then add WFI to the 10 L.
8. Sampling to detect pH, osmotic pressure, particle size and distribution, microbial limit, drug content, sedimentation ratio, viscosity, etc.
9. Preform filling using filling machine. The filling volume is 0.4 mL per bottle.

Description of Production Process 2:

1. HPMC was added into 60-70° C. water (WFI) 1 L for swelling, then stirring to a clear solution at room temperature add more 2 L WFI, marked as solution A.

2. Accurately weigh as the prescription request of Kolliphor® HS15, add WFI 2 L then stir at room temperature to get a clear solution, marked as solution B.
3. Accurately weigh of $NaH_2PO_4 \cdot 2H_2O$, $Na_2HPO_4 \cdot 12H_2O$, Sodium Chloride, Sodium Thiosulfate as prescription, add WFI 1 L then stir at room temperature to get a clear solution, marked as solution C.
4. Mixed solution A and solution B and solution C, filtration through a 0.2 μm polyethersulfone (PES) microporous filter, marked as solution D.
5. Accurately weigh of KDR2-2 add WFI 1 L, sterilized by steam sterilization at 121° C. for 30 minutes, marked as API solution E.
6. Add solution D to the solution E, stirring to a clear solution, add solution A, then add WFI to the 10 L.
7. Sampling to detect pH, osmotic pressure, particle size and distribution, microbial limit, drug content, sedimentation ratio, viscosity, etc.
8. Preform filling using filling machine. The filling volume is 0.4 mL per bottle.

Describe Production Process 3: Preparation of Micelles

1. HPMC was added into 60-70° C. water (WFI) 1 L for swelling, then stirring to a clear solution at room temperature add more 2 L WFI, marked as solution A.
2. Accurately weigh as the prescription request of Kolliphor® HS15, add WFI 2 L, then stir at room temperature to get a clear solution, marked as solution B.
3. Accurately weigh of $NaH_2PO_4 \cdot 2H_2O$, $Na_2HPO_4 \cdot 12H_2O$, Sodium Chloride, Sodium Thiosulfate as prescription, add WFI 1 L then stir at room temperature to get a clear solution, marked as solution C.
4. Mixed solution A and solution B and solution C, filter through a 0.2 μm polyethersulfone (PES) microporous filter, marked as solution D.
5. Accurately weigh of KDR2-2 add WFI 1 L, sterilized by steam sterilization at 121° C. for 30 minutes, marked as API solution E.
6. Add solution D to the solution E, stirring to a clear solution, add solution A, then add WFI to the 10 L.
7. Sampling to detect pH, osmotic pressure, particle size and distribution, microbial limit, drug content, sedimentation ratio, viscosity, etc.
8. Preform filling using filling machine. The filling volume is 0.4 mL per bottle.

Qualitative and Quantitative Formulation Composition of KDR2-2 Suspension Formulation

| Ingredient | Function | Quality | (%) w/v |
|---|---|---|---|
| KDR2-2 | Active | 1.00 g | 0.10 |
| Hypromellose (HPMC E4M) | Polymer Suspending Agent | 4.00 g | 0.40 |
| Polyoxyl 15-Hydroxystearate (Kolliphor ® HS 15) | Solubilizer | 45.00 g | 4.50 |
| Sodium Dihydrogen Phosphate Dihydrate ($NaH_2PO_4 \cdot 2H_2O$) | pH Adjuster | 2.10 g | 0.21 |
| Di-Sodium Hydrogen Phosphate Dodecahydrate ($Na_2HPO_4 \cdot 12H_2O$) | pH Adjuster | 16.00 | 1.60 |
| Sodium Chloride | Osmotic Pressure Regulator | 3.00 g | 0.30 |
| Sodium Thiosulfate | Antioxidant | 1.00 g | 0.10 |
| Water | NA | Adjust to 1000 ml | NA |

Example 8. Stability Study of Formulation

From the chromatograms in FIGS. 6A-6E and FIG. 7, it can be seen that the KDR2-2 formulations are unstable at 40° C. Initially, the main chromatograms have a small degradation peak, however, the KDR2-2 content changes from 99.7% to nearly 97% after the first month, and 93% or 94% after the second month. At the 3 month time point at 40° C., KDR2-2 purity (%) average value is 97.93%, which suggests the formulations of KDR2-2 have degradation occurring at nearly 2%.

By high-throughput analysis, it was confirmed that the KDR2-2 formulations (solution or suspension) are unstable at 40° C. The degradation products are Intermediate A (impurity 1) and Intermediate B (impurity 2) shown in Scheme 1.

Scheme 1

Scheme 1

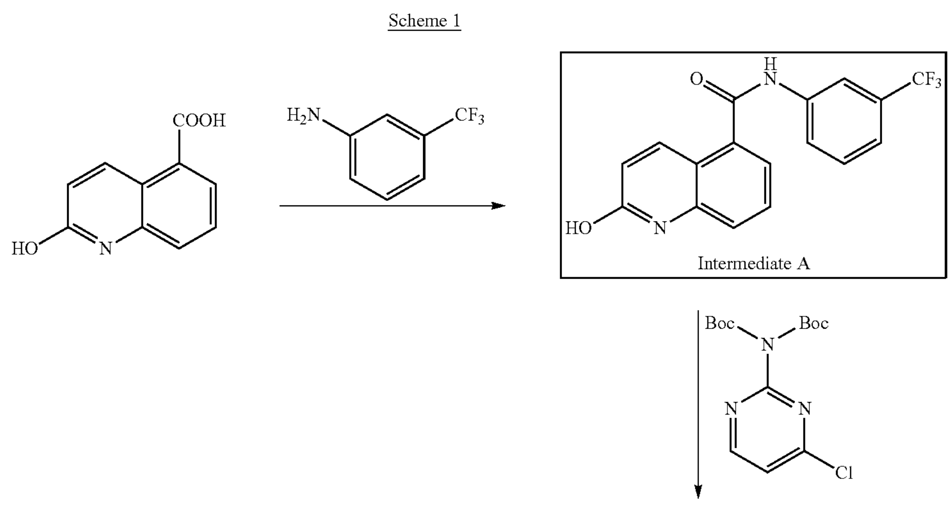

Intermediate A

-continued

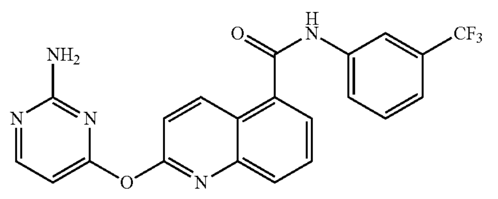

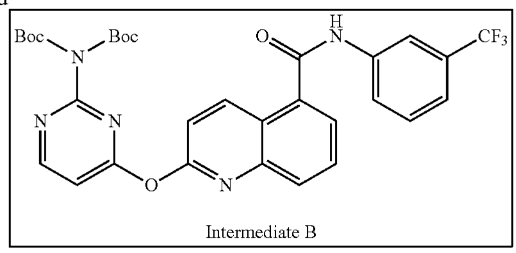

Intermediate B

According to eye drops preparation requests or formulation quality requirements, normal function of the eyes can endure osmotic pressure values of from about 200 to about 500 mOsmol/kg (with approximately 300 mOsmol/kg as an optimal value.) With the regard to the hemolysis test, 300 µl RD171207 formulation add 300 µL 1*PBS, total volume is 600 µL, the value of osmotic is 350 mOsmol/kg, pH value is 7.65; and 400 µL RD171207 formulation add 200 µL $ddH_2O$, the value of osmotic is 560 mOsmol/kg, the pH value is 7.77.

Figure 8:
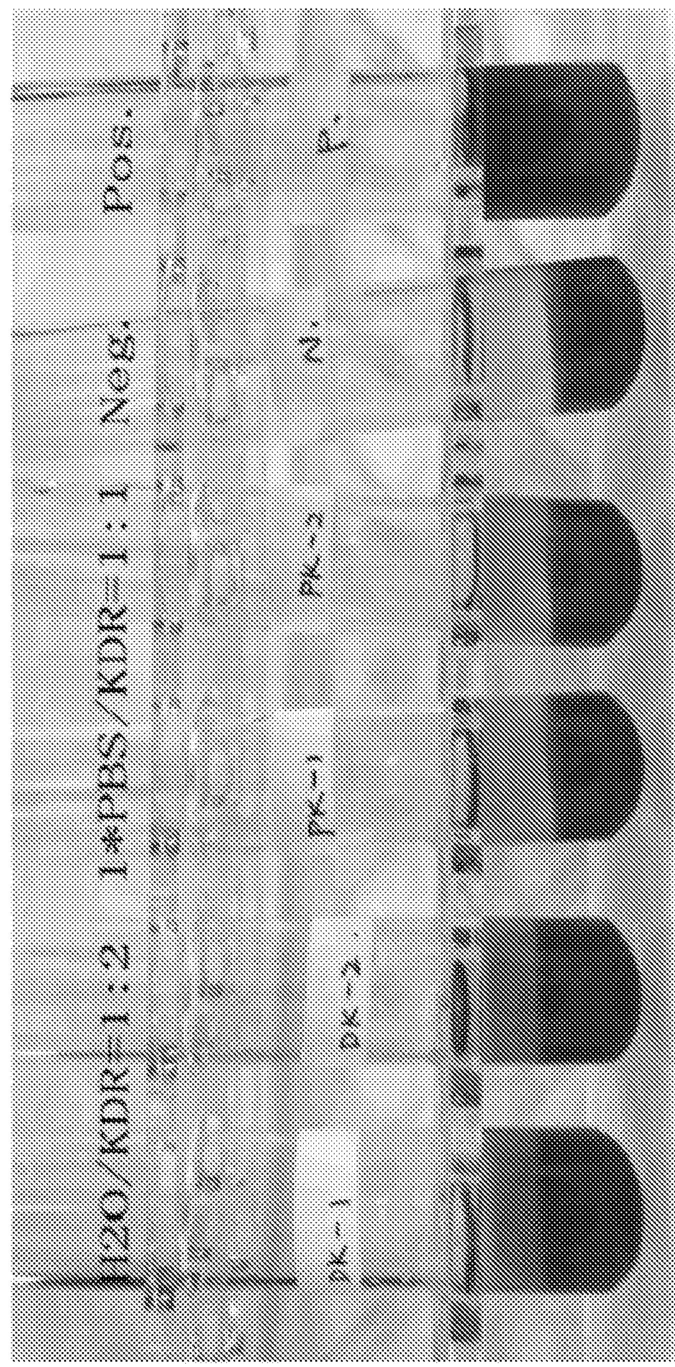
FIG. 8. Show the results of RBC cells hemolysis.

From the RBC cells hemolysis test, dilution with water or PBS can lower the osmotic value compared to RD171207 formulations, leading to the reduction of erythrocyte hemolysis (FIG. 8).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A pharmaceutical composition, comprising:

(i) particles of a compound of Formula (I):

(I)

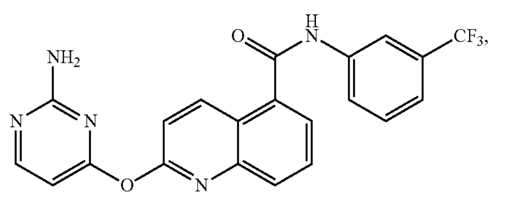

or an isotopic variant, tautomer, pharmaceutically acceptable salt, solvate, or hydrate thereof, wherein the particles of the compound of Formula (I), or an isotopic variant, tautomer, pharmaceutically acceptable salt, solvate, or hydrate thereof are micronized and at least about 90% of the particles have a diameter of from 0.1 µm to 40 µm; and (ii) pharmaceutically acceptable excipients, wherein the pharmaceutically acceptable excipients comprise a suspending agent, a wetting agent, a solubilizer, a pH adjuster, an anti-oxidant, and an osmotic pressure regulator;

the suspending agent is hydroxypropyl methylcellulose, the concentration of the suspending agent in the composition is up to 1% w/w;

the wetting agent is polyoxyl 15-hydroxystearate, the solubilizer is polyoxyl-35-castor oil, polyoxyl 15-hydroxystearate, or a combination thereof, the concentration of the solubilizer in the composition is up to 5% w/w;

the pH adjuster is a phosphate buffer or a hydrate thereof;

the anti-oxidant is a thiosulfate, the concentration of the anti-oxidant in the composition is up to 0.2% w/w; and the osmotic pressure regulator is a salt, the concentration of the osmotic pressure regulator in the composition is up to 0.5% w/w;

(iii) up to 2% w/w of total impurities and up to 0.5% w/w of any individual impurity, wherein the impurity comprises the compound of Formula (II):

(II)

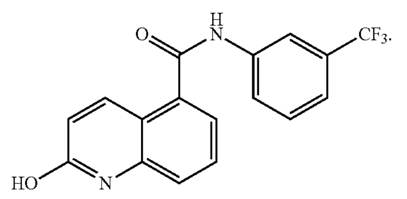

wherein the pharmaceutical composition is in a dosage form for ophthalmic dosing or administration and is formulated as a suspension, and wherein the composition comprises from 0.1% w/v-2.0% w/v of a compound of Formula (I), or an isotopic variant, tautomer, pharmaceutically acceptable salt, solvate, or hydrate thereof.

2. The composition of claim 1, wherein the particles of the compound of Formula (I), or an isotopic variant, tautomer, pharmaceutically acceptable salt, solvate, or hydrate thereof have a diameter of from about 0.1 µm to about 10 µm, or from about 0.3 µm to about 5 µm.

3. The composition of claim 1, wherein at least about 95% of the particles have a diameter of from about 0.1 µm to about 40 µm.

4. The composition of claim 1, wherein the particles have a D50 value of less than about 5 µm.

5. The composition of claim 1, wherein the dosage form is a modified-release dosage form.

6. The composition claim 1, wherein the buffer is a phosphate buffer selected from potassium phosphate, sodium dihydrogen phosphate dihydrate ($NaH_2PO_4 \cdot 2H_2O$), di-sodium hydrogen phosphate dodecahydrate ($Na_2HPO_4 \cdot 12H_2O$), or a combination thereof, or a hydrate thereof.

7. The composition of claim 1, wherein the osmotic pressure regulator is sodium chloride.

8. The composition of claim 1, wherein the thiosulfate is sodium thiosulfate.

9. The composition of claim 1, wherein the composition is stable for up to 24 months at a temperature of from about 20° C. to about 25° C.

10. The composition of claim 1, wherein the composition comprises less than about 0.9% w/w, about 0.8% w/w, about 0.7% w/w, about 0.6% w/w, about 0.5% w/w, about 0.4% w/w, about 0.3% w/w, about 0.2% w/w, or about 0.1% w/w of total impurities.

11. The composition of claim 1, wherein the composition has a pH of from about 4.0 to about 9.0, or about 5.0 to about 8.0, or about 6.5 to about 8.0, or about 7.0 to about 8.0.

12. A method of preparing the composition of claim 1, comprising:

(i) micronizing the compound of Formula (I), or an isotopic variant, tautomer, pharmaceutically acceptable salt, solvate, or hydrate thereof;

(ii) sterilizing the micronized compound of Formula (I), or an isotopic variant, tautomer, pharmaceutically acceptable salt, solvate, or hydrate thereof; and (iii) admixing a therapeutically effective amount of the compound of Formula (I), or an isotopic variant, tautomer, pharmaceutically acceptable salt, solvate, or hydrate thereof with the pharmaceutically acceptable excipients.

13. The method of claim 12, wherein a suspension comprising particles of the compound of Formula (I), or an isotopic variant, tautomer, pharmaceutically acceptable salt, solvate, or hydrate thereof is formed.

14. The method of claim 12, wherein the sterilization is performed at a temperature of about 121° C.

15. The method of claim 12, wherein the sterilization is performed for a period of from about 20 to about 30 minutes.

16. A method for treating a disease or disorder associated with the abnormal proliferation of angiogenesis, comprising administering to a subject in need thereof a therapeutically effective amount of the pharmaceutical composition of claim 1.

17. The method of claim 16, wherein the disease or disorder associated with the abnormal proliferation of angiogenesis is caused by an abnormity of VEGFR2.

18. The method of claim 16, wherein the abnormal proliferation of angiogenesis is ocular angiogenesis.

19. The method of claim 16, wherein the abnormal proliferation of angiogenesis is choroidal angiogenesis.

20. The method according to claim 16, wherein the disease or disorder associated with the abnormal proliferation of angiogenesis is wet macular degeneration, diabetic retinopathy or neovascular glaucoma.

* * * * *